US007348339B2

(12) United States Patent
Bailey et al.

(10) Patent No.: US 7,348,339 B2
(45) Date of Patent: Mar. 25, 2008

(54) IMIDAZOPYRIDINE DERIVATIVES AS KINASE INHIBITORS

(75) Inventors: Nicholas Bailey, Harlow (GB); Mark James Bamford, Harlow (GB); Haifeng Cui, King of Prussia, PA (US); Stephen Garland, Harlow (GB); Krista B Goodman, King of Prussia, PA (US); Mark A Hilfiker, King of Prussia, PA (US); Dennis Lee, King of Prussia, PA (US); Terence Aaron Panchal, Harlow (GB); Robert A Stavenger, King of Prussia, PA (US); David Matthew Wilson, Harlow (GB); Jason Witherington, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 435 days.

(21) Appl. No.: 10/508,760

(22) PCT Filed: Mar. 21, 2003

(86) PCT No.: PCT/GB03/01205

§ 371 (c)(1),
(2), (4) Date: Sep. 22, 2004

(87) PCT Pub. No.: WO03/080610

PCT Pub. Date: Oct. 2, 2003

(65) Prior Publication Data

US 2005/0197328 A1 Sep. 8, 2005

(30) Foreign Application Priority Data

Mar. 22, 2002 (GB) ................................ 0206860.9

(51) Int. Cl.
*A61K 31/44* (2006.01)
*A01N 43/42* (2006.01)
*C07D 265/30* (2006.01)
*C07D 295/00* (2006.01)
*C07D 498/02* (2006.01)

(52) U.S. Cl. ..................... 514/303; 546/118; 546/141; 544/127; 514/234.2; 514/307

(58) Field of Classification Search ................ 546/118, 546/141; 514/303, 307, 234.2; 544/127
See application file for complete search history.

(56) References Cited

U.S. PATENT DOCUMENTS

2007/0004771 A1* 1/2007 Lee et al. .................. 514/303

FOREIGN PATENT DOCUMENTS

DE 37 22 992 A 1/1989

(Continued)

OTHER PUBLICATIONS

Weber et al., Pharmacology, 2001, vol. 63, pp. 129-133.*

(Continued)

*Primary Examiner*—Margaret D. Seaman
*Assistant Examiner*—Niloofar Rahmani
(74) *Attorney, Agent, or Firm*—Wayne J. Dustman; Stephen Venetianer; Charles M. Kinzig

(57) ABSTRACT

A compound of the formula (I)

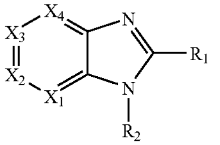

and physiologically acceptable salts and or N-oxides thereof wherein,
$X_1$ is N or $CR_3$; $X_2$ is N or $CR_4$; $X_3$ is N or $CR_5$; $X_4$ is N or $CR_6$.
with the proviso that at least one but not more than two of $X_1$, $X_2$, $X_3$ and $X_4$ represents N.
$R_1$ is a 5-, or 6-membered heterocyclic group selected from group a, b, c or d (a)

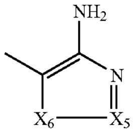

(b)

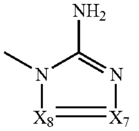

(c)

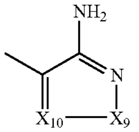

(d)

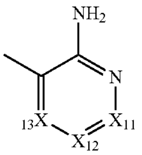

wherein $X_5$ is a group selected from N or $CR_7$ and $X_6$ is a group selected from O, S or $NR_8$; $X_7$ and $X_8$ which may be the same or different is a group selected from N or $CR_9$; $X_9$ is a group selected from O, S or $NR_8$ and $X_{10}$ is N or $CR_{10}$; $X_{11}$, $X_{12}$ and $X_{13}$ may be the same or different and selected from a group N or $CR_{11}$; processes for their preparation, pharmaceutical compositions containing them and their use in medicine.

11 Claims, No Drawings

FOREIGN PATENT DOCUMENTS

| | | | |
|---|---|---|---|
| DE | 3722992 | * | 1/1989 |
| EP | 1 034 793 A | | 9/2000 |
| WO | 01 57018 A | | 8/2001 |

OTHER PUBLICATIONS

Persidsky et al., Journal of Neuroimmunology, 2001, vol. 114, pp. 57-68.*

Nawwar, Galal A.M., et al: "Studies on 2-substituted methylazoles: the preparation and reactions of 2-cyanomethylimidazo'4,5bipyridine" Anles de Quimica (1993), 89(3), 375-8, XP009012073, compound 9.

Kumar, Shiv et al: "Adenine photodimerization in deoxyadenylate sequences: elucidation of th mechanism through structural studies of a major d(ApA) photoproduct" Nucleic Acids Research (1991), 19(11), 2841-7, XP001147581, compound 4.

* cited by examiner

IMIDAZOPYRIDINE DERIVATIVES AS KINASE INHIBITORS

The present invention relates to novel imidazopyridine derivatives, to processes for their preparation, to pharmaceutical compositions containing them and to their use in medicine. More particularly the present invention relates to novel imidazopyridine derivatives which are inhibitors, of kinases and in particular of mitogen and stress activated protein kinase-1 (herein after referred to as Msk-1) and or Rho-kinase 1 and or 2 (herein after referred to as ROCK 1 and 2).

An important mechanism by which cells sense and respond to extracellular stimuli is the activation and modulation of intracellular signal transduction pathways. One of the major signal transduction systems utilized by cells is the MAPK signalling pathways. These pathways share a common architecture, consisting of a cascade of protein kinases that are sequentially phosphorylated and activated, resulting in the activation of a MAP kinase (MAPK). Three MAP kinase pathways have been widely characterised: the Erk pathway, which responds to mitogenic stimuli and results in activation of Erk, and the JNK and p38 pathways, which are commonly associated with transducing cellular stress signals and result in activation of JNK and p38 MAPK.

Mitogen and stress-activated protein kinases 1 (Msk1) and 2 (Msk2, also named RSKB or RLPK) constitute a family of kinases that can be phosphorylated and activated by either p38 or Erk. Msks are reported to be localized exclusively to the nucleus, and are responsible for the phosphorylation and activation of the transcription factor CREB in response to certain stress stimuli. In macrophage and monocyte cells, Msk1 is involved in CREB-mediated transcriptional regulation of IL-1β and Cox2 in response to bacterial lipopolysaccharide. In addition, Msk1 can also phosphorylate the nucleosomal proteins histone H3 and HMG14, and thus may have a critical role in linking cellular signalling pathways to chromatin modification and modulation of transcription factor complexes. Inhibitors of kinases in the Erk MAPK cascade have been suggested for use in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth. Since Msks are activated by Erk MAPK, Msk inhibitors could serve a similar use. Although Msks are only one of a number of Erk substrates, CREB is involved in many different transcriptional activities, and Msk-mediated CREB phosphorylation could play a role in some cancers. In addition, through modulation of production of pro-inflammatory cytokines such as IL-1β and prostaglandins, inhibitors of Msks could be of use in treatments for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease and asthma.

Another of the major signal transduction systems utilized by cells is the RhoA-signalling pathways. RhoA is a small GTP binding protein that can be activated by several extracellular stimuli such as growth factor, hormones, mechanic stress, osmotic change as well as high concentration of metabolite like glucose. RhoA activation involves GTP binding, conformation alteration, post-translational modification (geranylgeranyllization and farnesylation) and activation of its intrinsic GTPase activity. Activated RhoA is capable of interacting with several effector proteins including ROCKs and transmit signals into cellular cytoplasm and nucleus.

ROCK1 and 2 constitute a family of kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of theses substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates b-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of myosin-actin bundle, leading to smooth muscle contraction. This phenomena is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

Inhibitors of ROCKs have been suggested for use in the treatments of a variety of diseases. They include cardiovascular diseases such as hypertension, chronic and congestive heart failure, cardiac hypertrophy, restenosis, chronic renal failure and atherosclerosis. In addition, because of its muscle relaxing properties, it is also suitable for asthma, male erectile dysfunctions, female sexual dysfunction and overactive bladder syndrome. ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, inflammatory bowel disease. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinsons disease, Alzheimers disease and other neurodegenerative disorders. Since ROCK inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes.

WO 97/12615 teaches novel 2-heteroaryl benzimidazole derivatives, which are inhibitors of the specific lipoxygenase enzyme 15-LO.

We have now identified a group of novel imidazopyridine derivatives which are potent inhibitors of the protein kinase Msk-1 and or Rho-associated kinase 1 and or 2.

The present invention thus provides compounds of the general formula (I)

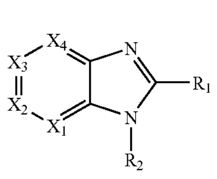

(I)

and physiologically acceptable salts and or N-oxides thereof wherein, $X_1$ is N or $CR_3$; $X_2$ is N or $CR_4$; $X_3$ is N or CRC; $X_4$ is N or $CR_6$.

with the proviso that at least one but not more than two of $X_1$, $X_2$, $X_3$ and $X_4$ represents N.

$R_1$ is a 5-, or 6-membered heterocyclic group selected from group a, b, c or d

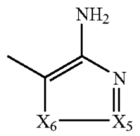

(a)

wherein $X_5$ is a group selected from N or $CR_7$ and $X_6$ is a group selected from O, S or $NR_8$;

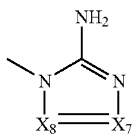

(b)

wherein $X_7$ and $X_8$ which may be the same or different is a group selected from N or $CR_9$;

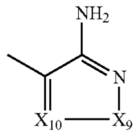

(c)

wherein $X_9$ is a group selected from O, S or $NR_8$ and $X_9$ is N or $CR_{10}$;

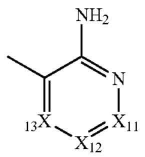

(d)

wherein $X_{11}$, $X_{12}$ and $X_{13}$ may be the same or different and selected from a group N or $CR_{11}$;

$R_2$ and $R_8$ independently represents hydrogen, hydroxy, aryl, heteroaryl, $C_{3-7}$cycloalkyl, heterocyclyl, a group $YR_{12}$, $N{=}R_{13}$, $CONR_{14}R_{15}$, $COCH_2NR_{19}R_{20}$, $NR_{14}COR_{16}$, $SO_2NR_{14}R_{15}$ or $C_{1-6}$alkyl [optionally substituted by a group selected from optionally substituted phenyl, $C_{3-7}$cycloalkyl, heteroaryl, heterocyclyl, acylamino, $NH_2$, $R_{19}NH$, $R_{19}R_{20}N$, $SO_2NR_{14}R_{15}$, $CONR_{14}R_{15}$, $NR_{14}COR_{16}$, $OalkNR_{19}R_{20}$, $SalkNR_{19}R_{20}$ or $NR_{17}SO_2R_{18}$ group];

$R_3$, $R_4$, $R_5$, $R_6$, $R_7$, $R_9$, $R_{10}$ and $R_{11}$ independently represent a group selected from hydrogen, halogen, hydroxy, $R_{19}O$, $R_{19}S(O)_n$, $NH_2$, $R_{19}NH$, $R_{19}R_{20}N$, nitro, formyl, $C_{1-4}$alkanoyl, alkenyl (optionally substituted by optionally substituted phenyl, heterocyclyl, or heteoaryl), carboxy, optionally substituted phenyl, heteroaryl, cycloalkyl, cycloalkylalkyl, aryloxy, heteroaryloxy, heterocyclyl, $CONR_{14}R_{15}$, $NR_{14}COR_{16}$, $SO_2NR_{14}R_{15}$, $NR_{17}SO_2R_{18}$ or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$, acylamino, hydroxy, $CONR_{14}R_{16}$, $NR_{14}COR_{16}$, $SO_2NR_{14}R_{15}$, $NR_{17}SO_2R_{18}$, $OalkNR_{19}R_{20}$, or $SalkNR_{19}R_{20}$ group]; $R_{19}$ and $R_{20}$ independently represent a group selected from $C_{1-6}$ alkyl, $C_{3-7}$cycloalkyl, $C_{3-7}$cycloalkylalkyl, aryl, aralkyl, heteroaryl, heteroarylalkyl, heterocyclyl or heterocyclylalkyl;

Y represents O, NH, $NR_{12}$ or $S(O)_n$;

$R_{12}$ represents aryl, heteroaryl, cycloalkyl, heterocyclyl or $C_{1-6}$alkyl [optionally substituted by a group selected from optionally substituted phenyl, $C_{3-7}$Cycloalkyl, heteroaryl, heterocyclyl, $NH_2$, $R_{19}NH$, $R_{19}R_{20}N$, acylamino, hydroxy, $CONR_{14}R_{15}$, $NR_{14}COR_{16}$, $SO_2NR_{14}R_{15}$, $NR_{17}SO_2R_{18}$ $OalkNR_{19}R_{20}$, or $SalkNR_{19}R_{20}$ group];

$R_{13}$ represents an alkylidene group which may be substituted by an aryl, heteroaryl, heterocyclyl or cycloalkyl group or $R_{13}$ represents a cycloalkylidene or heterocycloalkylidene group.

$R_{14}$ and $R_{15}$ independently represent hydrogen, aryl, heteroaryl, cycloalkyl or $C_{1-6}$-alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$, or acylamino group] or $R_{14}$ and $R_{15}$ together with the nitrogen atom to which they are attached form a 4-7 heterocyclic ring which may be saturated or unsaturated and optionally contains another heteroatom selected from O, N or $S(O)_n$;

$R_{16}$ and $R_{18}$ independently represent, aryl, heteroaryl, heterocyclyl, cycloalkyl or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$, or acylamino group] or the group $NR_{14}R_{15}$ wherein $R_{14}$ and $R_{15}$ have the meanings defined above;

$R_{17}$ represents hydrogen, aryl, heteroaryl, heterocyclyl, cycloalkyl or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$, or acylamino group];

Alk is a $C_{2-4}$ straight or branched alkylene chain n is zero, 1 or 2.

It will be appreciated that any of the substituents $R_1$ to $R_{20}$ as defined in formula (I) above may contain at least one asymmetric center and it is to be understood that the invention includes all possible enantiomers arising therefrom and mixtures thereof including racemates.

The term alkyl as a group or part of a group e.g. alkoxy, alkylthio, alkylamino, dialkylamino, optionally substituted alkyl e.g. aminoalkyl, cycloalkylalkyl, aralkyl, heteroarylalkyl or heterocyclylalkyl refers to a $C_{1-6}$ straight or branched chain alkyl group.

The term halogen includes fluorine, chlorine, bromine or iodine.

The term aryl as a group or part of a group e.g. aryloxy, aralkyl or arylamino refers to an optionally substituted phenyl or fused bicyclic aryl group e.g. naphthyl.

The terms aryl, optionally substituted phenyl, heteroaryl, $C_{3-7}$ cycloalkyl as a group or part of a group and 4-7 membered heterocyclyl as a group or part of a group includes such groups which are optionally substituted with 1 to 3 substituents which may be the same or different and selected from halogen, aryl, heteroaryl, heterocyclylalkyl, hydroxy, alkyl, alkoxy, trifluoroalkyl, amino, alkylamino, dialkylamino, arylamino, heteroarylamino, heterocyclylamino, acylamino, aminoalkyl, alkylaminoalkyl, dialkylaminoalkyl, acylaminoalkyl, arylaminoalkyl, heteroarylaminoalkyl, cycloalkylaminoalkyl, heteroclylaminoalkyl, hydroxyalkyl, $CONR_{14}R_{15}$, $CH2CONR_{14}R_{15}$ carboxy, carboxamido, alkoxycarbonyl, aminoalkoxy, dialkylaminoalkoxy, acylaminoalkoxy, sulphonamido, aminosulphonyl, cyano, formyl, nitro, $R_{21}O$ or $R_{21}S(O)_n$ wherein $R_{21}$ is a group selected from alkyl, aryl, heteroaryl or heterocyclylalkoxy and n is zero, one or two, or each of the said groups form part of a fused bicyclic ring system containing up to 10 ring members and which is at least partially saturated.

The term heteroaryl as a group or part of a group e.g. heteroaryloxy refers to a 5, or 6 membered ring or a fused 5,6 or 6,6 bicyclic ring system.

When heteroaryl represents a 5 membered group it contains a heteroatom selected from O, N or S and may optionally contain a further 1 to 3 nitrogen atoms. Examples of such groups include furanyl, thienyl, isoxazolyl, oxazolyl or imidazolyl.

When heteroaryl represents a 6-membered group it contains from 1 to 3 nitrogen atoms. Examples of such groups include pyridyl, pyrimidinyl, or triazinyl.

The term 5,6 fused bicyclic heteroaryl group refers to a group in which the 5-membered ring contains an oxygen, sulphur or NH group and the 6 membered ring optionally contains from 1 to 3 nitrogen atoms. Examples of such groups include benzofuranyl, benzothienyl or indolyl.

The term 6,6-fused bicyclic heteroaryl group refers to a bicyclic heteroaryl group which contains at least one nitrogen atom in one of the rings and may contain up to 3 nitrogen atoms in each ring. Examples of such groups include quinolinyl, isoquinolinyl or naphthyridinyl also the term 6,6 fused bicyclic heteroaryl group refers to a 6-membered heteroaryl group which is fused to a partially saturated carbocyclic group. Examples of such a group includes tetrahydroquinolinyl or tetrahydroisoquinolinyl.

The term heterocyclyl as a group or part of a group e.g. heterocyclylalkyl or heterocyclylalkylidene refers to a bridged heterocyclic group or a 4-7 membered heterocyclyl group which is linked to the rest of the compound of formula (I) via a carbon or nitrogen atom in that group and which contains one or two hetero atoms selected from N, O or $S(O)_n$, and when the heterocyclyl group contains a ring member NH or the heterocyclyl group is substituted by a primary or secondary amino group then the term also includes N-alkyl, N-optionally substituted phenyl, N-benzyl or, N-acyl derivatives thereof. The term heterocyclic also includes bridged heterocyclic. Examples of such heterocyclic groups include optionally substituted pyrrolidine, piperidine, piperazine homopiperazine, morpholine, thiomorpholine and (8-methyl-8-aza-bicyclo[3.2.1]oct-3-yl)-amine.

The term cycloalkyl as a group or part of a group e.g. cycloalkylalkyl or cycloalkylidene refers to a 3-7 membered carbocyclic group.

The term fused bicyclic ring system containing up to 11 ring members and which is at least partially saturated includes carbocyclic and heterocyclic 6,5,6,6 and 6,7 bicyclic ring systems. Examples of such 6,5 and 6,6 carbocyclic ring systems include those wherein the bicyclic ring comprises a benzene ring fused to a 5-, 6- or -membered carbocyclic ring which is at least partially saturated e.g. tetrahydronaphthyl, indanyl or indenyl. Examples of such 6,5, 6,6 or 6,7 heterocyclic rings include those wherein one ring is benzene which is fused to a 5, 6 or 7 membered ring containing one or two hetero atoms selected from O, S or N e.g. indolinyl, isoindolinyl, 2,3-dihydro-1H-isoindol-5-yl, dihydrobenzofuranyl, dihydrobenzothienyl, 1,3-benzodioxolyl, benzopyrrolyl, 1,3-benozodithiolyl, 1,4-benzodioxanyl, chromanyl, chromenyl or 2,3,4,5-tetrahydro-1H-benzo[c]azepin-8-yl.

The term acyl as a group or part of the acylamino group referes to an alkanoyl, aroyl, aralkanoyl, alkoxycarbonyl, aryloxycaronyl or aralkoxycarbonyl group.

The compounds of formula (I) form salts with inorganic and organic acids and the invention includes such salts formed with physiologically acceptable inorganic and organic acids.

The compounds of formula (I), form N-oxides. Thus, the compound of formula (I) wherein $X_3$ is N or $X_2$ is N forms an N oxide and the invention includes such compounds.

A preferred class of compounds of formula (I) are those wherein only one of $X_1$, $X_2$, $X_3$ or $X_4$ represents N. Within this class conveniently $X_2$ or $X_3$ represent N or more particularly $X_3$ represents N.

A further preferred class of compounds are those wherein $X_1$ and $X_3$ each represents N.

A further preferred class of compounds of formula (I) are those wherein $R_1$ is a group selected from (c) or (d).

A prefered group of compounds according to the invention are those of formula (I) wherein $X_3$ is N, $X_1$ is $CR_3$; $X_2$ is $CR_4$ and $X_4$ is $CR_6$.

$R_1$ is a group c wherein $X_9$ is O and $X_{10}$ is N; Within this group a preferred class are those wherein $R_2$ is hydrogen, optionally substituted alkyl, aryl, heteroaryl, C3-7cycloalkyl or heterocyclyl, $R_3$ represent a group selected from hydrogen, halogen, $R_{19}O$, $R_{19}S(O)_n$, $R_{19}NH$, $R_{19}R_{20}N$, carboxyl,)$CONR_{14}R_{15}$, $SO_2NR_{14}R_{15}$, optionally substituted phenyl, heteroaryl, $C_{1-6}$alkyl, or methyl [substituted by a group selected from optionally substituted phenyl, $R_{19}NH$, $R_{19}R_{20}N$, $CONR_{14}R_{15}$, $SO_2NR_{14}R_{15}R_{19}O$ or $R_{19}S(O)_n$ $R_4$ represents hydrogen, halogen, optionally substituted $C_{1-4}$alkyl, $R_{19}O$, $R_{19}S(O)_n$, $R_{19}NH$ or $R_{19}R_{20}N$; $R_6$ represents hydrogen, halogen, optionally substituted $C_{1-6}$-alkyl, optionally substituted phenyl, $R_{19}NH$, $R_{19}R_{20}N$, $R_{19}O$ or $R_{19}S(O)_n$ or methyl substituted by optionally substituted phenyl.

When $R_1$ is the group (c) this is conveniently a group wherein $X_9$ is oxygen and $X_{10}$ is nitrogen or $X_9$ is $NR_8$ wherein $R_8$ is hydrogen or methyl and $X_9$ is CH.

When $R_1$ is the group (d) this is conveniently a group wherein $X_1$, and $X_{12}$ each represent CH and $X_{13}$ is the group CH or N.

The group $R_1$ is preferably a group (c) wherein $X_9$ is oxygen and $X_{10}$ is nitrogen.

Examples of suitable $R_2$ groups include hydrogen, $C_{1-6}$alkyl such as methyl, ethyl, isopropyl, sec butyl and 2-ethylbutyl, $C_{3-7}$ cycloalkyl e.g. cyclopropyl, cyclobutyl, cyclopentyl, cyclohexyl, cycloheptyl, $C_{3-7}$cycloalkylalkyl e.g. $C_{3-7}$ cycloalkylmethyl such as cyclopropylmethyl or cyclohexylmethyl, optionally substituted phenyl such as phenyl or phenyl substituted by [amino eg 4-aminophenyl, dialkylamino, eg dimethylamino, dialkylaminoalkylamino (eg dimethylaminoethylamino, N-methyl, dimethylaminoethylamino, N,N-bis(2-dimethylaminoethyl)amino), alkyl eg ethyl, alkanoyl eg acetyl, alkoxy (eg methoxy or 3-methylbutoxy)halo, (eg chlorine or bromine, hydroxy, aminoalkyl eg aminomethyl, hydroxalkoxy (eg 2-hydroxyethoxy or 3-hydroxypropoxy), aminoalkoxy eg 2-aminoethoxy, alkylaminoalkoxy eg 2-methylaminoethoxy, dialkylaminoethoxy (eg 2-dimethylaminoethoxy, 2 diethylaminoethoxy, 2 diethylamino-1-methylethoxy, 2-disopropylamino-1-methylethoxy), N-aralkyl-Nalkylaminoalkoxy eg N-benzyl N-methylaminoethoxy, aminocarbonylalkoxy eg (aminocarbonylmethoxy, aminocarbonyl-2-methylethoxy, aminocarbonylethoxy), alkylaminocarbonylalkoxy eg methylaminocarbonylmethoxy, dialkylaminocarbonylalkoxy, eg dimethylaminocarboxymethoxy, ureidoalkoxy eg ureidomethoxy, alkylureido eg 3-methylureido, dialkylaminoacetamido eg dimethylaminoacetamido, alky(thioalkoxy eg methylthiomethoxy, phenylthioalkoxy eg phenylthiomethoxy, alkisulphinylalkoxy eg methylsulphinylmethoxy, phenylsulphinylalkoxy eg phenylsulphinylmethoxy, alkylsulphonylalkoxy eg methylsulphonylmethoxy, phenylsulphonylalkoxy eg phenylsulphonylmethoxy, cyanoalkoxy eg cyanomethoxy or 2-cyanoethoxy, acylaminoethoxy eg (t-butoxycarbonylaminoethoxy, isoxazolylaminoethoxy, isonicotinylaminoethoxy, alkylsuphonylamino-alkoxy eg methylsulphonylaminoethoxy, phenylsulphonylaminoalkoxy eg phenylsulphonylaminoethoxy, alkoxycarbonylalkoxy eg 2-methoxycarbonyl 1-methylethoxy, heterocyclylalkoxy eg (morpholinoethoxy, piperidinoethoxy, 1-pyrroldino-2-ylmethoxy, heterocyclyloxy e.g. 1-methyl-piperidino-4-yloxy, heterocyclyl eg 3-pyrrolidinyl,], alkyl (substituted by hydroxy e.g. 2-hydroxy-1-methyl-ethyl), alkyl substituted by [amino eg (3-aminopropyl, 4-aminobutyl, 5 aminopentyl), acylamino e.g. 4-butyloxycarbonylamino-butyl, $R_{19}$NH or $R_{19}R_{20}$N e.g. (2-dimethylamino-1-methylethyl, 4-diethylamino-1-methyl-butyl or 3-dimethylaminopropyl)], alkyl e.g. methyl or ethyl substituted by a 4-7-membered heterocyclyl group e.g. 4-methylpiperazin-1-ethyl, 2-piperazin-yl-ethyl, piperidine 4-yl methyl or piperidine 3-yl methyl, a 4-7 membered heterocyclyl group such as piperidinyl e.g. piperidin-4-yl or piperidin-3-yl or pyrrolidinyl e.g. pyrrolidin-3-yl, a 5,6 fused bicyclic hetroaryl group such as indazolyl e.g. 5-indazolyl or 6-indazolyl, or 6,6 fused bicyclicheterocyclic e.g. tetrahydroisoquinolin-5-yl, 2-methyl tetrahydroisoquinolin-7-yl, 2-methanesulphonyl-tetrahydroisoquinolin-7-yl or tetrahydroisoquinolin-7-yl, 3,4 dihydro-2H-isoquinolin-1-one-7-yl, a 6,5 fused heterocyclic group e.g. 2,3-dihydro-1H-isoindol-5-yl, or benzo{1,3]dioxol-5-yl or a 6,7 fused heterocyclic e.g. 2,3,4,5-tetrahydro-1H-benzo[c]azepin-8-yl.

When $X_2$ is $CR_4$ then the group $R_4$ is conveniently hydrogen, methyl or alkoxy e.g, methoxy, alkylthio e.g. methylthio, phenylamino or phenoxy optionally substituted by halogen e.g. fluoro or acetamido.

When $X_3$ is $CR_5$ then $R_5$ is coveniently hydrogen, alkyl e.g. methyl or alkoxy e.g. methoxy or optionally substituted phenoxy e.g. phenoxy.

Wherein $X_4$ is $CR_6$ the group $R_6$ is conveniently hydrogen, halogen e.g. chlorine, hydroxyalkyl e.g hydroxymethyl, alkyl e.g, methyl, alkoxy e.g. methoxy, optionally substituted phenyl e.g. phenyl or a 4-7 membered heterocyclyl group e.g. 1-pyrrolidinyl or 1-pyrazolyl.

Wherein $X_1$ is the group $CR_3$ then $R_3$ is conveniently hydrogen, halogen e.g. bromine, hydroxy, carboxyl, optionally substituted phenyl e.g. phenyl or phenyl (substituted by one or two groups selected from alkoxy e.g. methoxy or ethoxy, hydroxy, hydroxymethyl, trifluoromethyl, trifluoromethoxy, amino, acetamido, aminoalkyl, e.g. aminomethyl, or aminoethyl, alkyl e.g. methyl or ethyl, carboxyl carboxamido, N,N-dimethylcarboxamido, cyano, formyl, aryloxy e.g. phenoxy $CH_3S(O)_n$ wherein n is zero, 1 or 2, $CH_3SO_2NH$, or halogen e.g. fluorine), or heterocyclyl e.g. 5-methyl-1,2,4-oxadiazol-3-yl, an heteroaryl group e.g thienyl (optionally substituted by formyl, alkyl eg methyl or phenyl) such as 2-thienyl, 4-methylthienl, 5-phenylthienyl, 5-formylthienyl, or 3-thienyl, 2-furanyl, pyridyl such as 3-pyridyl or 4-pyridyl, 3,5-dimethylisoxazol-4-yl, indolyl or 8-quinolinyl, benzothienyl, a 6,5-fused bicycloheterocyclyl e.g 5-benzo[1,3]dioxolylor $R_3$ is optionally substituted phenyl such as phenyl or halophenyl e.g. fluorophenyl substituted by the group $CH_2NR_{19}R_{20}$ wherein $R_{19}$ is alkyl e.g. methyl or ethyl, phenyl or a heterocyclic group such as a 4-7 heterocyclic group and $R_{20}$ is hydrogen or methyl, or $NR_{19}R_{20}$ is a 4-7 heterocyclic group. Examples of suitable $NR_{19}R_{20}$ groups include ethylamino, dimethylamino, 4-morpholino, pyrrolidino, piperidino, piperidin-4-yl-amino or 1-t-butoxycarbonyl-piperdin-4-yl-amino, or $R_3$ is alkyl substituted by a 4-7 membered heterocyclyl group or a group $NR_{19}R_{20}$ wherein $R_{19}$ is hydroxylalkyl, optionally substituted benzyl, $C_{3-7}$ cycloalkyl, a heterocyclic group e.g. bridge heterocycle, or a 4-7 membered heterocyclyl, 4-7 membered heterocycylalkyl or $C_{3-7}$ cycloalkylalkyl Conveniently the 4-7 membered heterocyclyl group or moiety is selected from a 5-7 membered group containing one or 2 ring members selected from nitrogen or oxyen e.g. pyrrolidinyl, piperidinyl, morpholinyl piperazinyl or homo-piperazinyl. $R_{20}$ is hydrogen, methyl or acetyl. Examples of such $R_3$ groups include 3-hydroxypropylamino, 4-bromobenzylamino, 4-methoxybenzylamino, 4-piperidinylaminomethyl, N4-piperidinyl-N-methylaminomethyl, 1-t-butyoxycarbonyl-piperidinyl-aminomethyl 4-aminopiperidinomethyl, 1,4-diazepan-1-ylmethyl, piperazinomethyl, 4-methylpiperazinomethyl, 4-acetylpiperizin-1-ylmethyl, 4-ethylpiperazinomethyl 4-morpholinomethyl, piperidinomethyl, 4-(methylamino)piperidinomethyl, 4-cyclopropylaminopiperidinomethyl, pyrrolidinomethyl, 3-dimethylaminopyrrolidinomethyl, 2-hydroxymethylpyrrolidinomethyl, 4-ethylpiperazinomethyl, 3-pyrrolidin-1-yl-propylaminomethyl, 4-(4-fluorophenyl)piperazinomethyl, 3-piperidinyl-1-yl-propylaminomethyl, 3-morpholin-4-yl-propylaminomethyl, 3-(4-methylpiperazin-yl propylaminomethyl, 1-methyl piperidin-4-yl-aminomethyl, 4-pyrrolidinocarbonylmethyl-piperazinomethyl, 2-pyrrolidin-1-ylmethylpyrrolidinomethyl, 2-pyrrolidin-1-yl-ethylaminomethyl, 3-dimethylaminopyrrolidinomethyl, 1-methyl-piperidin-4- ylaminomethyl, 1-isopropyl-piperidin-4-ylaminomethyl, 3-dimethylaminopyrrolidinomethyl, 2-(morpholin-yl-methyl)-pyrrolidinomethyl, 3-piperidin-1-yl-propylaminomethyl, 3-morpholin-4-yl-propylaminomethyl, 3-(4-methylpiperazin-1-ylpropylaminomethyl, piperidin-1-ylmethylpyrrolidinomethyl, 3,5-dimethylpiperazinomethyl, pyrrolidin-1-ylpiperidinomethyl, pyrrolidino-3-ylaminomethyl, pyrrolidin-2-ylmethylaminomethyl, 4-aminomethylcyclohexymethylaminomethyl, 4-aminocyclohexylaminomethyl, 2-piperazin-1-ylethylamoinomethyl, 3-amino-pyrrolidinomethyl, pyrrolidino-2-ylmethylaminomethyl, piperidin-4-ylmethylaminomethyl, 4-aminomethylpiperdininomethyl, 4-(cyclopropylaminopiperidinomethyl, 3-(piperazino-1-yl)propylaminomethyl, 2-(morpholin-4-ylmethyl)pyrrolidinomethyl 2-(piperidin-1-ylmethyl)pyrrolidinomethyl, 2-(piperazin-1-ylmethyl)pyrrolidinomethyl, piperidin-4-ylmethyl, N-piperidin-4-yl-acetamidomethyl, or $R_3$ is 4-heterocyclyoxy e.g. piperidin-4-yloxy, or heterocyclylalkyloxy e.g. piperidin-4-ylmethyloxy, or $R_3$ is vinyl optionally substituted by optionally substituted phenyl e.g. 4-methyloxystyryl or $R_3$ is the group $CONR_{14}R_{15}$ wherein $R_{15}$ is hydrogen, $R_{14}$ is benzyl, phenethyl, aminoalkyl e.g. 3-aminopropyl 4-aminobutyl or 6-aminohexyl or is a 4-7 membered heterocyclyl group. Conveniently the heterocyclyl group is a 5-6 membered group in which one ring member is nitrogen which may be sustitute by an aminoalkylcarbonyl group. Suitable examples include piperidinyl e.g. 3 or 4-piperidinyl 1-aminomethylcarbonyl-piperidin-4-yl, or pyrrolidinyl e.g. 3-pyrroldinyl or $R_{14}$ is a 4-7 membered heterocyclylalkyl group. Conveniently the heterocyclic moiety is a 5-7 membered group containing a nitrogen atom and another hetero member selected from oxygen or nitrogen. Suitable examples of such heterocyclylalkyl groups include piperidinylmethyl e.g. piperidin-2-ylmethyl or piperidin-4-ylmethyl, morpholinylmethyl e.g. morpholin-2-ylmethyl or piperazinoethyl, or $R_{14}$ and $R_{15}$ together with the nitrogen atom to which they are attached represent a 4-7 membered heterocyclyl group. Conveniently the heterocyclyl group is a 5-7 membered group which may contain an additional hetero member selected from oxygen, nitrogen or substituted nitrogen Examples of such groups include piperazino, 1-methylpiperazino, 4-(2-aminoethyl) piperazino, 4-(t-butoxycarbonylaminoethyl)piperazino, 4-aminoalkylcarbonylpiperazino, e.g. 4-aminomethylcarbonylpiperazino, 4-aminoethylcarbonylpiperazino, 4-1-(aminoethylcarbonylpiperazino, 4-(1-methylaminoethylylcarbonylpiperazino, 4-pyrrolidin-2-yl-carbonylpiperazino, pyrrolidino, 3-aminopyrrolidino, 2-methoxycarbonylpyrrolidino, morpholino, 2-(pyrrolidin-1-yl)methyl pyrrolidino or $R_3$ is a group $R_{19}S(O)_n$ wherein n is zero, 1 or 2 and $R_{19}$ is optionally substitued phenyl eg phenyl optionally substituted by methoxy or heteroaryl and conveniently n is zero, or $R_3$ is a group $R_{19}NH$ and $R_{19}$ is optionally substitued phenyl or heteroaryl e.g. phenyl, 4-morpholinophenyl or 3-aminopyridyl. Examples of suitable compounds according to the invention include those whose preparation is specifically described in examples 1 to 316.

Specific preferred compounds according to the invention include:

2-(4-amino-furazan-3-yl)-1-ethyl-N-[(2R)-2-morpholinyl-methyl]-1H-imidazo[4,5-c]pyridine-7-carboxamide 2-(4-amino-furazan-3-yl)-1-ethyl-N-[(2S)-2-morpholinylmethyl]-1H-imidazo[4,5-c]pyridine-7-carboxamide 4-{6-[(4-fluorophenyl)oxy]-1-[4-(methyloxy)phenyl]-1H-imidazo[4,5-c]pyridin-2-yl}-furazan-3-ylamine hydrochloride 4-{1-(4-{[2-(dimethylamino)ethyl]oxy}phenyl)-6-[(4-fluorophenyl)oxy]-1H-imidazo[4,5-c]pyridin-2-yl}-furazan-3-ylamine hydrochloride 2-(4-amino-furazan-3-yl)-1-(cyclopropylmethyl)-N-(2-morpholinylmethyl)-1H-imidazo[4,5-c]pyridine-7-carboxamide hydrochloride 4-[1-ethyl-6-(methyloxy)-1H-imidazo[4,5-c]pyridin-2-yl]-furazan-3-ylamine 4-[1-ethyl-6-(methylthio)-1H-imidazo[4,5-c]pyridin-2-yl]-furazan-3-ylamine 4-[1-ethyl-6-(phenyloxy)-1H-imidazo[4,5-c]pyridin-2-yl]-furazan-3-ylamine 4-{1-ethyl-6-[(4-fluorophenyl)oxy]-1H-imidazo[4,5-c]pyridin-2-yl}-furazan-3-ylamine N-(3-{[2-(4-amino-furazan-3-yl)-1-ethyl-1H-imidazo[4,5c]pyridin-6-yl]oxy}phenyl)acetamide hydrochloride N-(4-{[2-(4-amino-furazan-3-yl)-1-ethyl-1H-imidazo[4,5-c]pyridin-6-yl]oxy}phenyl)acetamide hydrochloride 2-(4-amino-furazan-3-yl)-1-ethyl-N-phenyl-1H-imidazo[4,5-c]pyridin-6-amine 4-[1-(phenylmethyl)-1H-imidazo[4,5-c]pyridin-2-yl]-furazan-3-ylamine hydrochloride 4-[1-(2,2,2-trifluoroethyl)-1H-imidazo[4,5-c]pyridin-2-yl]-furazan-3-ylamine 4-[1-(4-fluorophenyl)-1H-imidazo[4,5-c]pyridin-2-yl]-furazan-3-amine hydrochloride 4-(6-bromo-1-ethyl-1H-imidazo[4,5-c]pyridin-2-yl)-furazan-3-ylamine 4-{7-bromo-1-[4-(methyloxy)phenyl]-1H-imidazo[4,5-c]pyridin-2-yl}-furazan-3-ylamine 4-[2-(4-amino-furazan-3-yl)-7-bromo-1H-imidazo[4,5-c]pyridin-1-yl]phenol 4-[1-(4-{[2-(dimethylamino)ethyl]oxy}phenyl)-7-phenyl-1H-imidazo[4,5-c]pyridin-2-yl]-furazan-3-ylamine 4-(7-bromo-1-phenyl-1H-imidazo[4,5-c]pyridin-2-yl)-furazan-3-ylamine 4-(1,7-diphenyl-1H-imidazo[4,5-c]pyridin-2-yl)-furazan-3-ylamine 4-[1-phenyl-7-(2-thienyl)-1H-imidazo[4,5-c]pyridin-2-yl]-furazan-3-ylamine 4-[2-(4-amino-furazan-3-yl)-1-phenyl-1H-imidazo[4,5-c]pyridin-7-yl]phenol 2-(4-amino-furazan-3-yl)-1-phenyl-1H-imidazo[4,5-c]pyridine-7-carboxylic acid 4-(7-{4-[(ethylamino)methyl]phenyl}-1-phenyl-1H-imidazo[4,5-c]pyridin-2-yl)-furazan-3-ylamine 4-[7-(3,5-dimethyl-4-isoxazolyl)-1-phenyl-1H-imidazo[4,5-c]pyridin-2-yl]-furazan-3-ylamine 4-{1-ethyl-7-[3-(ethyloxy)phenyl]-1H-imidazo[4,5-c]pyridin-2-yl)-furazan-3-ylamine hydrochloride 2-(4-amino-furazan-3-yl)-1-ethyl-N-methyl-1H-imidazo[4,5-c]pyridine-7-sulfonamide hydrochloride 2-(4-amino-furazan-3-yl)-1-ethyl-N,N-dimethyl-1H-imidazo[4,5-c]pyridine-7-sulfonamide hydrochloride {3-[2-(4-amino-furazan-3-yl)-1-ethyl-1H-imidazo[4,5-c]pyridin-7-yl]phenyl}methanol hydrochloride 4-(1-ethyl-7-{4-[(phenylamino)methyl]phenyl}-1H-imidazo[4,5-c]pyridin-2-yl)-furazan-3-ylamine 4-[1-ethyl-7-(2-fluorophenyl)-1H-imidazo[4,5-c]pyridin-2-yl]-furazan-3-ylamine hydrochloride 4-{1-ethyl-7-[4-(methylsulfonyl)phenyl]-1H-imidazo[4,5-c]pyridin-2-yl}-furazan-3-ylamine hydrochloride 4-{1-ethyl-7-[4-(trifluoromethyl)phenyl]-1H-imidazo[4,5-c]pyridin-2-yl}furazan-3-ylamine hydrochloride 4-[7-(2,4-difluorophenyl)-1-ethyl-1H-imidazo[4,5-c]pyridin-2-yl]-furazan-3-ylamine hydrochloride 5-[2-(4-Amino-furazan-3-yl)-1-ethyl-1H-imidazo[4,5-c]pyridin-7-yl]-thiophen-2-yl}-carbaldehyde 4-[7-(1-benzothien-3-yl)-1-ethyl-1H-imidazo[4,5-c]pyridin-2-yl]-furazan-3-ylamine hydrochloride 4-{1-ethyl-7-[2-(trifluoromethyl)phenyl]-1H-imidazo[4,5-c]pyridin-2-yl}furazan-3-ylamine hydrochloride 4-{1-ethyl-7-[4-(methylthio)phenyl]-1H-imidazo[4,5-c]pyridin-2-yl}-furazan-3-ylamine hydrochloride 4-[1-ethyl-7-(4-methyl-2-thienyl)-1H-imidazo[4,5-c]pyridin-2-yl]-furazan-3-ylamine hydrochloride 4-[7-(2,6-dimethylphenyl)-1-ethyl-1H-imidazo[4,5-c]pyridin-2-yl]-furazan-3-ylamine hydrochloride 5-[2-(4-amino-furazan-3-yl)-1-ethyl-1H-imidazo[4,5-c]pyridin-7-yl]-2-fluorobenzaldehyde hydrochloride 4-[7-(3-aminophenyl)-1-ethyl-1H-imidazo[4,5-c]pyridin-2-yl]-furazan-3-ylamine hydrochloride 4-(1-ethyl-7-{3-[(trifluoromethyl)oxy]phenyl}-1H-imidazo[4,5-c]pyridin-2-yl)-furazan-3-ylamine hydrochloride 1-{3-[2-(4-amino-furazan-3-yl)-1-ethyl-1H-imidazo[4,5-c]pyridin-7-yl]phenyl}ethanone hydrochloride N-4-[2-(4-amino-furazan-3-yl)-1-ethyl-1H-imidazo[4,5-c]pyridin-7-yl]phenyl}methanesulfonamide hydrochloride 4-[1-ethyl-7-(5-phenyl-2-thienyl)-1H-imidazo[4,5-c]pyridin-2-yl]-furazan-3-ylamine hydrochloride 4-{7-[3,5-bis(trifluoromethyl)phenyl]-1-ethyl-1H-imidazo[4,5-c]pyridin-2-yl}-furazan-3-ylamine hydrochloride 4-{1-ethyl-7-[4-fluoro-3-(1-pyrrolidinylmethyl)phenyl]-1H-imidazo[4,5-c]pyridin-2-yl}-furazan-3-ylamine hydrochloride 4-{1-ethyl-7-[3-fluoro-4-(1-pyrrolidinylmethyl)phenyl]-1H-imidazo[4,5-c]pyridin-2-yl}-furazan-3-ylamine hydrochloride 4-(1-ethyl-7-{4-[(ethylamino)methyl]-3-fluorophenyl}-1H-imidazo[4,5-c]pyridin-2-yl)-furazan-3-ylamine hydrochloride 4-(7-{[(3S)-3-amino-1-pyrrolidinyl]sulfonyl}-1-ethyl-1H-imidazo[4,5-c]pyridin-2-yl)-furazan-3-ylamine hydrochloride 4-{1-ethyl-7-[4-(methylsulfinyl)phenyl]-1H-imidazo[4,5-c]pyridin-2-yl}-furazan-3-yl-amine hydrochloride 4-[1-ethyl-7-(4-morpholinylcarbonyl)-1H-imidazo[4,5-c]pyridin-2-yl]-furazan-3-ylamine 2-(4-amino-furazan-3-yl)-1-ethyl-N-(2-hydroxyethyl)-1H-imidazo[4,5-c]pyridine-7-carboxamide 4-[1-ethyl-7-(1-piperidinylcarbonyl)-1H-imidazo[4,5-c]pyridin-2-yl]-furazan-3-ylamine 2-(4-amino-furazan-3-yl)-1-ethyl-N,N-dimethyl-1H-imidazo[4,5-c]pyridine-7-carboxamide 2-(4-amino-furazan-3-yl)-1-ethyl-N-(1-methylethyl)-1H-imidazo[4,5-c]pyridine-7-carboxamide 2-(4-amino-furazan-3-yl)-1-ethyl-N-phenyl-1H-imidazo[4,5-c]pyridine-7-carboxamide 2-(4-amino-furazan-3-yl)-1-ethyl-N-methyl-1H-imidazo[4,5-c]pyridine-7-carboxamide 2-(4-amino-furazan-3-yl)-1-ethyl-N-[2-(methyloxy)ethyl] 1H-imidazo[4,5-c]pyridine-7-carboxamide 2-(4-amino-furazan-3-yl)-1-ethyl-N-(2,2,6,6-tetramethyl-4-piperidinyl)-1H-imidazo[4,5-c]pyridine-7-carboxamide 1,1-dimethylethyl[5-({[2-(4-amino-furazan-3-yl)-1-ethyl-1H-imidazo[4,5-c]pyridin-7-yl]carbonyl}amino)pentyl]carbamate 1,1-dimethylethyl 4-{2-[({[2-(4-amino-furazan-3-yl)-1-ethyl-1H-imidazo[4,5-c]pyridin-7-yl]carbonyl}amino)methyl]phenyl}-1-piperazinecarboxylate 2-(4-amino-furazan-3-yl)-N-[3-(dimethylamino)propyl]-1-ethyl-1H-imidazo[4,5-c]pyridine-7-carboxamide 2-(4-amino-furazan-3-yl)-1-ethyl-N-methyl-N-(phenylmethyl)-1H-imidazo[4,5-c]pyridine-7-carboxamide 2-(4-amino-furazan-3-yl)-1-ethyl-N-[2-(1-methyl-2-pyrrolidinyl)ethyl]-1H-imidazo[4,5-c]pyridine-7-carboxamide 2-(4-amino-furazan-3-yl)-N-[2-(4-chlorophenyl)-1-(hydroxymethyl)ethyl]-1-ethyl-1H-imidazo[4,5-c]pyridine-7-carboxamide 4-(1-ethyl-7-{[4-(phenylmethyl)-1-piperazinyl]carbonyl}-1H-imidazo[4,5-c]pyridin-2-yl)-furazan-3-ylamine 2-(4-amino-furazan-3-yl)-1-ethyl-N-{[4-(methyloxy)phenylmethyl)-1H-imidazo[4,5-c]pyridine-7-carboxamide 2-(4-amino-furazan-3-yl)-N-(5-aminopentyl)-1-ethyl-1H-imidazo[4,5-c]pyridine-7-carboxamide trifluoroacetate 2-(4-amino-furazan-3-yl)-1-ethyl-N-((2-(1-piperazinyl)phenyl]methyl}-1H-imidazo[4,5-c]pyridine-7-carboxamide trifluoroacetate 2-(4-amino-furazan-3-yl)-N-[(1S,5R,7S)-3-aminotricyclo[3.3.1.1~3,7-]dec-1-yl]-1-ethyl-1H-imidazo[4,5-c]pyridine-7-carboxamide trifluoroacetate 2-(4-amino-furazan-3-yl)-N-{[4-chloro-3-(trifluoromethylphenyl]methyl}-1-ethyl-1H-imidazo[4,5-c]pyridine-7-carboxamide 4-(1-ethyl-7-{[4-(4-pyridinylmethyl)-1-piperazinyl]carbonyl}-1H-imidazo[4,5-c]pyridin-2-yl)-furazan-3-ylamine 2-(4-amino-furazan-3-yl)-1-ethyl-N-[2-(4-methyl-1-piperidinyl)ethyl]-1H-imidazo[4,5-c]pyridine-7-carboxamide 2-(4-amino-furazan-3-yl)-1-ethyl-N-{2-[(phenylmethyl)amino]ethyl}-1H-imidazo[4,5-c]pyridine-7-carboxamide 4-{1-ethyl-7-[(4-ethyl-1-piperazinyl)carbonyl]-1H-imidazo[4,5-c]pyridin-2-yl}-furazan-3-ylamine 2-(4-amino-furazan-3-yl)-N-[2-(2,4-dichlorophenyl)ethyl]-1-ethyl-1H-imidazo[4,5-c]pyridine-7-carboxamide 2-(4-amino-furazan-3-yl)-1-ethyl-N-[2-(methylamino)ethyl]-1H-imidazo[4,5-c]pyridine-7-carboxamide 4-{1-ethyl-7-[4-(4-morpholinylcarbonyl)phenyl]-1H-imidazo[4,5-c]pyridin-2-yl}-furazan-3-ylamine 4-[2-(4-amino-furazan-3-yl)-1-ethyl-1H-imidazo[4,5-c]pyridin-7-yl]-N-(2-phenylethyl)benzamide 4-{1-ethyl-7-[4-(1-pyrrolidinylcarbonyl)phenyl]-1H-imidazo[4,5-c]pyridin-2-yl}-furazan-3-ylamine 4-[2-(4-amino-furazan-3-yl)-1-ethyl-1H-imidazo[4,5-c]pyridin-7-yl]-N-(phenylmethyl)benzamide methyl 1-({4-[2-(4-amino-furazan-3-yl)-1-ethyl-1H-imidazo[4,5-c]pyridin-7-yl]phenyl}carbonyl)-L-prolinate 4-(1-ethyl-7-{4-[(4-methyl-1-piperazinyl)carbonyl]phenyl})-1H-imidazo[4,5-c]pyridin-2-yl)-furazan-3-ylamine 3-[2-(4-amino-furazan-3-yl)-1-ethyl-1H-imidazo[4,5-c]pyridin-7-yl]-N-(2-phenylethyl)benzamide 3-[2-(4-amino-furazan-3-yl)-1-ethyl-1H-imidazo[4,5-c]pyridin-7-yl]-N-(phenylmethyl)benzamide methyl 1-({3-[2-(4-amino-furazan-3-yl)-1-ethyl-1H-imidazo[4,5-c]pyridin-7-yl]phenyl}carbonyl)-L-prolinate 4-(1-ethyl-7-{3-[(4-methyl-1-piperazinyl)carbonyl]phenyl}-1H-imidazo[4,5-c]pyridin-2-yl)-furazan-3-ylamine 4-{1-ethyl-7-[3-(4-morpholinylcarbonyl)phenyl]-1H-imidazo[4,5-c]pyridin-2-yl}-furazan-3-ylamine 4-[1-ethyl-7-(1-pyrrolidinylcarbonyl)-1H-imidazo[4,5-c]pyridin-2-yl]-furazan-3-ylamine 2-(4-amino-furazan-3-yl)-1-ethyl-N-phenyl-1H-imidazo[4,5-c]pyridin-7-amine 4-[1-ethyl-4-(ethyloxy)-1H-imidazo[4,5-c]pyridin-2-yl]-furazan-3-ylamine 4-[1-ethyl-4-(methyloxy)-1H-imidazo[4,5-c]pyridin-2-yl]-furazan-3-ylamine 1-{[2-(4-amino-furazan-3-yl)-1-ethyl-1H-imidazo[4,5-c]pyridin-7-yl]methyl}4-piperidinamine hydrochloride

[2-(4-amino-furazan-3-yl)-1-ethyl-1H-imidazo[4,5-c]pyridin-7-yl]methanol

N-{[2-(4-amino-furazan-3-yl)-1-ethyl-1H-imidazo[4,5-c]pyridin-7-yl]methyl}-1-(1-methylethyl)-4-piperidinamine hydrochloride 1-{[2-(4-amino-furazan-3-yl)-1-ethyl-1H-imidazo[4,5-c]pyridin-7-yl]methyl}-N-methyl-4-piperidinamine hydrochloride ((2S)-{[2-(4-amino-furazan-3-yl)-1-ethyl-1H-imidazo[4,5-c]pyridin-7-yl]methyl}-2-pyrrolidinyl)methanol 4-(7-{[(3R)-3-(dimethylamino)-1-pyrrolidinyl]methyl}-1-ethyl-1H-imidazo[4,5-c]pyridin-2-yl)-furazan-3-ylamine hydrochloride 4-(7-{[(3S)-3-(dimethylamino)-1-pyrrolidinyl]methyl}-1-ethyl-1H-imidazo[4,5-c]pyridin-2-yl)-furazan-3-ylamine hydrochloride 3-({[2-(4-amino-furazan-3-yl)-1-ethyl-1H-imidazo[4,5-c]pyridin-7-yl]methyl}amino)-1-propanol 4-[1-ethyl-7-({[2-(1-piperazinyl)ethyl]amino}methyl)-1H-imidazo[4,5-c]pyridin-2-yl]-furazan-3-ylamine hydrochloride 2-(4-amino-furazan-3-yl)-1-ethyl-N-[(3R)-3-pyrrolidinyl]-1H-imidazo[4,5-c]pyridine-7-carboxamide hydrochloride 2-(4-amino-furazan-3-yl)-1-ethyl-N-[(3S)-3-pyrrolidinyl]-1H-imidazo[4,5-c]pyridine-7-carboxamide hydrochloride N-{[2-(4-amino-furazan-3-yl)-1-ethyl-1H-imidazo[4,5-c]pyridin-7-yl]methyl}-N-4-piperidinylacetamide hydrochloride 4-(7-bromo-1-ethyl-4-methyl-1H-imidazo[4,5-c]pyridin-2-yl)-furazan-3-ylamine

[2-(4-amino-furazan-3-yl)-7-bromo-1-ethyl-1H-imidazo[4,5-c]pyridin-4-yl]methanol hydrochloride 4-[1-ethyl-7-({4-[(methylamino)acetyl]-1-piperazinyl}carbonyl)-1H-imidazo[4,5-c]pyridin-2-yl]-furazan-3-ylamine hydrochloride 4-(7-{[4-(aminoacetyl)-1-piperazinyl]carbonyl}-1-ethyl-1H-imidazo[4,5-c]pyridin-2-yl)-furazan-3-ylamine hydrochloride 4-(7-[{(3-aminopropanoyl)-1-piperazinyl]carbonyl}-1-ethyl-1H-imidazo[4,5-c]pyridin-2-yl)-furazan-3-ylamine hydrochloride 4-[7-({4-[(2R)-2-aminopropanoyl]-1-piperazinyl}carbonyl)-1-ethyl-1H-imidazo[4,5-c]pyridin-2-yl-furazan-3-ylamine hydrochloride 4-[7-({4-((2S)-2-aminopropanoyl]-1-piperazinyl}carbonyl)-1-ethyl-1H-imidazo[4,5-c]pyridin-2-yl]-furazan-3-ylamine hydrochloride 4-[9-cyclopropyl-2-(methylthio)-9H-purin-8-yl]-furazan-3-ylamine 4-[1-(3-Methoxy-phenyl)-1H-imidazo[4,5-c]pyridin-2-yl]-furazan-3-ylamine 3-[2-(4-Amino-furazan-3-yl)-imidazo[4,5-c]pyridin-1-yl]-phenol 1-{4-[2-(4-Amino-furazan-3-yl)-imidazo[4,5-c]pyridin-1-yl]-phenyl}-ethanone oxime 4-[1-(2-Methyl-1,2,3,4-tetrahydro-isoquinolin-7-yl)-1H-imidazo[4,5-c]pyridin-2-yl]-furazan-3-ylamine 4-(1-Benzo[1,3]dioxol-5-yl-1H-imidazo[4,5-c]pyridin-2-yl)-furazan-3-ylamine 7-[2-(4-Amino-furazan-3-yl)-imidazo[4,5-c]pyridin-1-yl]-3,4-dihydro-2H-isoquinolin-1-one 4-[1-(2-Methanesulfonyl-1,2,3,4-tetrahydro-isoquinolin-7-yl)-1H-imidazo[4,5-c]pyridin-2-yl]-furazan-3-ylamine 4-[2-(4-Amino-furazan-3-yl)-imidazo[4,5-c]pyridin-1-yl]-N-hydroxy-benzamidine 4-[1-(2,3,4,5-Tetrahydro-1H-benzo[c]azepin-8-yl)-1H-imidazo[4,5-c]pyridin-2-yl]-furazan-3-ylamine 4-[1-(1H-Indazol-6-yl)-1H-imidazole[4,5-c]pyridin-2-yl]-furazan-3-ylamine 4-[1-(1H-Indazol-5-yl)-1H-imidazole[4,5-c]pyridin-2-yl]-furazan-3-ylamine 4-{1-[4-(2-Diethylamino-ethoxy)-phenyl]-1H-imidazo[4,5-c]pyridin-2-yl}-furazan-3-ylamine hydrochloride 4-{1-[4-(3-Dimethylamino-propoxy)-phenyl]-1H-imidazo[4,5-c]pyridin-2-yl}-furazan-3-ylamine hydrochloride 4-{1-[4-((S)-1-Pyrrolidin-2-ylmethoxy)-phenyl]-1H-imidazo[4,5-c]pyridin-2-yl}-furazan-3-ylamine 4-{1-[4-(2-Morpholin-4-yl-ethoxy)-phenyl]-1H-imidazo[4,5-c]pyridin-2-yl}-furazan-3-ylamine hydrochloride N-{4-[2-(4-Amino-furazan-3-yl)-imidazo[4,5-c]pyridin-1-yl]-phenyl}-N,N',N'-trimethyl-ethane dihydrochloride N-{4-[2-Amino-furazan-3-yl)-imidazo[4,5-c]pyridin-1-1-yl-phenyl}-N-(2-dimethylamino-ethyl)-N',N'-dimethyl-ethane-1,2-diamine 4-{1-[4-(1-Methyl-piperidin-4-yloxy)-phenyl]-1H-imidazo[4,5-c]pyridin-2-yl}-furazan-3-ylamine 4-{1-[4-(3-Dimethylamino-propyl)-phenyl]-1H-imidazo[4,5-c]pyridin-2-yl}-furazan-3-ylamine 4-[1-(4-Dimethylamino-phenyl)-1H-imidazo[4,5-c]pyridin-2-yl]-furazan-3-ylamine {4-[2-(4-Amino-furazan-3-yl)-imidazo[4,5-c]pyridin-1-yl]-phenoxy}acetonitrile 4-{1-[4-((S)-1-Methyl-pyrrolidin-2-ylmethoxy)-phenyl]-1H-imidazo[4,5-c]pyridin-2-yl}-furazan-3-ylamine N-{4-[2-(4-amino-furazan-3-yl)-imidazo[4,5-c]pyridin-1-yl]-phenyl}-C-dimethylamino-acetamide N-{4-[2-(4-Amino-furazan-3-yl)-imidazo[4,5-c]pyridin-1-yl]-phenyl}-N',N'-dimethyl-ethane-1,2-diamine 4-{1-[3-(2-Dimethylamino-ethyloxy)-phenyl]-1H-imidazo[4,5-c]pyridin-2-yl}furazan-3-ylamine 4-{1-[3-(3-Dimethylamino-propoxy)-phenyl]-1H-imidazo[4,5-c]pyridin-2-yl}-furazan-3-ylamine 1-{4-[2-(4-Amino-furazan-3-yl)-imidazo[4,5-c]pyridin-1-yl]-phenyl}-3-methyl-urea 4-{1-[3-(1-Methyl-piperin-4-yloxy)-phenyl]-1H-imidazo[4,5-c]pyridine-2-yl}furazan-3-ylamine 4-{1-[4-(2-Piperidin-1-yl-ethoxy)-phenyl]-1H-imidazo[4,5-c]pyridin-2-yl}-furazan-3-ylamine 4-{1-[4-(2-Pyrrolidin-1-yl-ethoxy)-phenyl]-1H-imidazo[4,5-c]pyridin-2-yl}-furazan-3-ylamine 4-{1-[4-(2-Dimethylamino-1-methyl-ethoxy)-phenyl]-1H-imidazo[4,5-c]pyridin-2-yl}-furazan-3-ylamine 4-(1-{4-[2-(Benzyl-methyl-amino)-ethoxy]-phenyl}-1H-imidazo[4,5-c]pyridin-2-yl)-furazan-3-ylamine 2-{4-[2-(4-Amino-furazan-3-yl)-imidazo[4,5-c]pyridin-1-yl]-phenoxy}-acetamide 2-{4-[2-(4-Amino-furazan-3-yl)-imidazo[4,5-c]pyridin-1-yl]-phenoxy}-N-methyl-acetamide 2-{4-[2-(4-Amino-furazan-3-yl)-imidazo[4,5-c]pyridin-1-yl]-phenoxy}-N,N-dimethylacetamide 2-{4-[2-(4-Amino-furazan-3-yl)-imidazo[4,5-c]pyridin-1-yl]-phenoxy}ethanol 3-{4-[2-(4-Amino-furazan-3-yl)-imidazo[4,5-c]pyridin-1-yl]-phenoxy}-propan-1-ol 3-{4-[2-(4-Amino-furazan-3-yl)-imidazo[4,5-c]pyridin-1-yl]-phenoxy}-propionitrile N-(2-{4-[2-(4-Amino-furazan-3-yl)-imidazo[4,5-c]pyridin-1-yl]-phenoxyethyl)-isonicotinamide N-(2-{4-[2-(4-Amino-furazan-3-yl)-imidazo[4,5-c]pyridin-1-yl]-phenoxy}-ethyl)-acetamide Isoxazole-5-carboxylic acid (2-{4-[2-(4-amino-furazan-3-yl)-imidazo[4,5-c]pyridin-1-yl]-phenoxy}-ethyl)-amide N-(2-{4-[2-(4-Amino-furazan-3-yl)-imidazo[4,5-c]pyridin-1-yl]-phenoxy}-ethyl)-methanesulfonamide 2-{4-[2-(4-Amino-furazan-3-yl)-imidazo[4,5-c]pyridin-1-yl]-phenoxy}-propionamide 2-{4-[2-(4-Amino-furazan-3-yl)-imidazo[4,5-c]pyridin-1-yl]-phenoxy}-2-methyl-propionamide (2-{4-[2-(4-Amino-furazan-3-yl)-imidazo[4,5-c]pyridin-1-yl]-phenoxy}-ethyl)-carbamic acid tert-butyl ester 4-{1-[4-(2-Methylamino-ethoxy)-phenyl]-1H-imidazo[4,5-c]pyridin-2-yl}-furazan-3-ylamine 4-{1-[4-(2-Amino-ethoxy)-phenyl]-1H-imidazo[4,5-c]pyridin-2-yl}-furazan-3-ylamine 4-[1-(4-Methylsulfanylmethoxy-phenyl)-1H-imidazo[4,5]pyridin-2-yl]-furazan-3-ylamine 4-[1-(4-Benzenesulfinylmethoxy-phenyl)-1H-imidazo[4,5-c]pyridin-2-yl]-furazan-3-ylamine 4-[1-(4-Benzenesulfonylmethoxy-phenyl)-1H-imidazo[4,5-c]pyridin-2-yl]-furazan-3-ylamine 4-[1-(4-Methanesulfinylmethoxy-phenyl)-1H-imidazo[4,5-c]pyridin-2-yl]-furazan-3-ylamine 4-[1-(4-Phenylsulfanylmethoxy-phenyl)-1H-imidazo[4,5-c]pyridin-2-yl]-furazan-3-ylamine N-(2-{4-[2-(4-Amino-furazan-3-yl)-imidazo[4,5-c]-pyridin-1-yl}-phenoxy}-ethyl)-benzenesulfonamide (2-{4-[2-(4-Amino-furazan-3-yl)-imidazo[4,5-cpyridin-1-yl]-phenoxy}-ethyl)-urea N-(2-{4-[2-(4-Amino-furazan-3-yl)-imidazo[4,5-c]pyridin-1-yl]-phenoxy}-ethyl)-benzamide 3,5-Dimethyl-isoxazole-4-sulfonic acid (2-{4-[2-(4-amino-furazan-3-yl)-imidazo[4,5-c-pyridin-1-yl]-phenoxy}-ethyl)-amide N-[5-(2-{4-[2-(4-Amino-furazan-3-yl)-imidazo[4,5-c]pyridin-1-yl]-phenoxy}-ethylsulfamoyl)-4-methyl-thiazol-2-yl]-acetamide 4-[1-(4-Methanesulfonylmethoxy-phenyl)-1H-imidazo[4,5-c]pyridin-2-yl]-furazan-3-ylamine N-(2-{4-[2-(4-Amino-furazan-3-yl)-imidazo[4,5-c]-pyridin-1-yl]-phenoxy}-ethyl)-benzenesulfonamide 4-{4-[2-(4-Amino-furazan-3-yl)-imidazo[4,5-c]pyridin-1-yl]phenoxy}-piperidine-1-carboxylic acid benzyl ester 4-[2-(4-Amino-furazan-3-yl)-imidazo[4,5-c]pyridin-1-yl]-phenol 2-(4-Amino-furazan-3-yl)-1-ethyl-1H-imidazo[4,5-c]pyridine-7-carboxylic acid (piperidin-2-ylmethyl)amide 2-(4-Amino-furazan-3-yl)-1-ethyl-1H-imidazo[4,5-c]pyridine-7-carboxylic acid [1-((S)-1-pyrolidin-2-yl-methanoyl)-piperidin-4-yl]-amide 2-(4-Amino-furazan-3-yl)-1-ethyl-1H-imidazo[4,5-c]pyridine-7-carboxylic acid [1-(2-amino-ethanoyl)-piperidin-4-yl]-amide N-[2-(4-Amino-furazan-3-yl)-1-ethyl-1H-imidazo[4,5-c]pyridin-7-ylmethyl]-cyclohexane-1,4-diamine 2-(4-Amino-furazan-3-yl)-1-ethyl-1H-imidazo[4,5-c]pyridine-7-carboxaldehyde 2-(4-Amino-furazan-3-yl)-1-ethyl-1H-imidazo[4,5-c]pyridine-7-carboxylic acid [1-(3-amino-propanoyl)-piperidin-4-yl]-amide

[2-(4-Amino-furazan-3-yl)-1-ethyl-1H-imidazo[4,5-c]pyridin-7-ylmethyl]-piperidin-4-yl-amine 4-(4-Chloro-1-ethyl-1H-imidazo[4,5-c]pyridin-2-yl)-furazan-3-ylamine 4-{1-Ethyl-7-[(3-piperazin-1-yl-propylamino)-methyl]-1-ethyl-1H-imidazo[4,5-c]pyridin-2-yl}-furazan-3-ylamine 4-(1-Ethyl-7-{[(3-(4-methyl-piperazin-1-yl)-propylamino]-methyl}-1-ethyl-1H-imidazo[4,5-c]pyridin-2-yl)-furazan-3-ylamine

[2-(4-Amino-furazan-3-yl)-1-ethyl-1H-imidazo[4,5-c]pyridin-7-ylmethyl]-[1-(2-methoxy-ethyl)-piperidin-4-yl]-amine 4-[1-Ethyl-7-((R)-2-piperazin-1-ylmethyl-pyrrolidin-1-ylmethyl)-1H-imidazo[4,5-c]pyridin-2-yl]-furazan-3-ylamine

2

{3-[2-(4-Amino-furazan-3-yl)-1H-imidazo[4,5-c]pyridin-1-yl]-propyl}-carbamic acid tert-butyl ester 4-(1-Cyclohexylmethyl-1H-imidazo[4,5-c]pyridin-2-yl)-furazan-3-ylamine

[2-(4-Amino-furazan-3-yl)-1-cyclopropyl-1H-imidazo[4,5-c]pyridin-7-ylmethyl]-piperidin-4-yl-amine 4-[2-(4-Amino-furazan-3-yl)-1-ethyl-1H-imidazo[4,5-c]pyridin-7-ylmethyl]-piperazine-1-carboxylic acid tert-butyl ester 4-(3-Ethyl-3H-imidazo[4,5-c]pyridin-2-yl)-furazan-3-ylamine 3-(1-Ethyl-1H-imidazo[4,5-c]pyridin-2-yl)-pyrazin-2-ylamine and physiologically acceptable salts thereof.

The ability of the compounds of formula (I) to antagonise the effect of the kinase Msk-1 may be determined using published procedures such as those described in WO9967283 and WO0127315. Alternatively the following in vitro assay may be used.

Thus the Msk-1 antagonist activity was determined using human recombinant Msk-1 expressed in Sf9 cells (WO9967283). The enzyme underwent prior activation by incubation with MAPK (p42), which was removed prior to storage and subsequent assay. The assay of Msk-1 activity involved incubation with peptide substrate and $ATP^{33}$, the subsequent incorporation of $P^{33}$ into the peptide was quantified by Scintillation Proximity Assay (SPA—Amersham Pharmacia).

For IC50 determination, test compounds were typically dissolved at 10 mM in 100% DMSO, with subsequent serial dilution into 10% DMSO. Compounds were typically assayed over an eleven point dilution range with a concentration in the assay of 10 uM to 3 nM, in duplicate. IC50 values were calculated by bespoke curve fitting software.

Assays were performed in clear bottomed, white walled, 384 well plates, in a total assay volume of 12.5 ul. The assays contained: 2 nM activated MSK1; 2 uM biotinylated peptide (biotin-GRPRTSSFAEG-OH); 20 uM ATP; 25 Bq per pmole $ATP^{33}$; 50 mM Hepes; 10 mM $MgCl_2$; 0.1 mM EDTA; 0.0025% Tween-20; 5 mM β-Mercaptoethanol; pH 7.5. The reactions were incubated at 20° C. for 60 minutes, then terminated by the addition of 10 ul of 200 mM EDTA.

Streptavidin PVT SPA beads were added to a concentration of 0.2 mg per well. The plates were shaken for 10 minutes before centrifugation at 2500 rpm for 10 minutes. $P^{33}$ incorporation was quantified by scintillation counting in a Wallac Trilux.

The compounds of the invention are therefore useful in the treatment or prevention of diseases and/or conditions mediated through the kinase Msk-1. Thus the compounds are useful for the treatment or prophylaxis of disorders associated with neuronal degeneration resulting from ischemic events or inflammatory conditions. Examples of such disorders include acute stroke e.g. cerebral stroke, thromboembolic stroke, hemorrhagic stroke and cerebral ischemia, multi infarct dementia, pain, arthritis e.g. rheumatoid arthritis, osteoarthritis, psoriasis, and enteropathic arthritis, multiple sclerosis, Alzheimers disease, Parkinson's disease, amyotrophic lateral sclerosis, spinal cord injury and asthma. The compounds may also be useful for the treatment of irritable bowel syndrome, inflammatory bowel disease and certain cancers.

The invention therefore provides for the use of a compound of formula (I) and/or physiologically acceptable salts thereof for use in therapy and in particular for use as a medicine for inhibiting the effects of the kinase Msk-1.

The invention also provides for the use of a compound of formula (I) and/or a physiologically acceptable derivative or salt thereof for the manufacture of a medicament for inhibiting the effects of the kinase Msk-1.

According to a further aspect, the invention also provides for a method for inhibiting the effects of the kinase Msk-1 in a mammal e.g. a human, comprising administering to a patient in need thereof an effective amount of a compound of formula (I) and/or a physiologically acceptable derivative or salt thereof.

The ability of the compounds of formula (I) to antagonise the effect of the kinase ROCK1 may be determined by using the following assays:

1. ROCK Kinase Assay:

ROCK inhibitor activity was determined using human recombinant ROCK1 kinase domain (amino acid 1-578) expressed in Sf9 cells (WO9967283). The enzyme was purified using his-tag NTA column and Source 15 HPLC chromatography. The assay of Rock-1 activity involved incubation with peptide substrate and $ATP^{33}$, the subsequent incorporation of $P^{33}$ into the peptide was quantified by Scintillation Proximity Assay (SPA—Amersham Pharmacia).

For IC50 determination, test compounds were typically dissolved at 10 mM in 100% DMSO, with subsequent serial dilution into 10% DMSO. Compounds were typically assayed over an eleven point dilution range with a concentration in the assay of 10 uM to 3 nM, in duplicate. IC50 values were calculated by bespoke curve fitting software.

Assays were performed in clear bottomed, white walled, 96 well plates, in a total assay volume of 40 ul. The assays contained: 1 nM hROCK11; 1 uM biotinylated peptide (biotin-Ahx-AKRRRLSSLRA-CONH2); 1 uM ATP; 25 Bq per pmole $ATP^{33}$; 12.5 mM Hepes pH7.4; 7.5 mM $MgCl_2$; 0.015% BSA. The reactions were incubated at 20° C. for 120 minutes, then terminated by the addition of 10 ul of 200 mM EDTA.

Streptavidin PVT SPA beads were added to a concentration of 0.4 mg per well. The plates were shaken for 10 minutes before centrifugation at 2500 rpm for 10 minutes. $P^{33}$ incorporation was quantified by scintillation counting in a Wallac Trilux.

2. Aorta Artery Contraction Assay:

Male Sprague-Dawley rats (350-400 g) are anesthetized with 5% Isoflurane in $O_2$ and euthanized by exsanguination. Proximal descending thoracic aortae are removed and placed in oxygenated (95% $O_2$, 5% $CO_2$) ambient temperature Krebs solution (pH 7.4) with the following composition (mM): NaCl 112.0, KCl 4.7, $CaCl_2$ 2.5, $KH_2PO_2$ 1.2, $MgSO_4$ 1.2, $NaHCO_3$25.0, dextrose 11.0, indomethacin 0.01, and L-NAME 0.1. The isolated aortae are cut into four 3 mm rings and each segment is suspended by two 0.1 mm diameter tungsten wire hooks and placed in a 10 mL organ bath containing oxygenated (95% $O_2$, 5% $CO_2$) 37° C. Krebs solution (pH 7.4). The tissues are equilibrated under 1.0 grams resting tension for approximately 30 minutes. Responses are measured isometrically using a Grass FT 03 force-transducer and recorded on a Grass polygraph (model 7D) as change in tension.

After the equilibration period, each tissue is contracted with 60 mM KCl for about 15 minutes, washed with 37° C. Krebs solution, and allowed to relax to the resting tension. The 60 mM KCl contraction is repeated. The tissue is then contracted to equilibration with 1 M norepinephrine and washed with 37° C. Krebs solution and allowed to relax to the resting tension.

A cumulative concentration-response curve to phenylephrine is obtained by dosing at 0.5 log unit intervals (1 nM to 1 M) and the $EC_{80}$ is determined. Following several washes, each vessel is contracted to equilibrium with an $EC_{80}$ concentration of phenylephrine and tone is reversed by adding cumulative amounts of a ROCK inhibitor at 0.5 log unit intervals (0.1 nM to 3 M). When constructing cumulative concentration-response, a higher concentration of vasoactive agent is added to the tissue bath after the previous response has reached a plateau.

3. In Vivo Effect of ROCK Inhibitors (Intravenous, IV):

Rats are anesthetised with isoflurane 3% for the implantation of femoral venous and arterial catheters. During the experiment, anaesthesia was maintained at 2%. Each rat received an intravenous bolus dose of vehicle followed by a bolus doses of ROCK inhibitors at 10, 30, 100 and 300 ug/kg with approx 20 minutes between doses. Blood samples are taken at 20 minutes after doses 10, 30 and 300 ug/kg for the subsequent determination of plasma levels of ROCK inhibitors.

Arterial blood pressure and heart rate derived from the blood pressure are recorded on strip chart and also on a computerised data acquisition system (Po-Ne-Mah, V 3.30, Gould Instruments). Hemodynamic data is presented as the maximum change from pre-dose control expressed as means+/−SEM.

The compounds of the invention are therefore useful in the treatment or prevention of diseases and/or conditions mediated through Rho kinases-1 and/or -2.

Thus the compounds are useful for the treatment or prophylaxis of cardiovascular diseases such as hypertension, chronic and congestive heart failure, cardiac hypertrophy, restenosis, chronic renal failure and atherosclerosis. The compounds are useful for the treatment or prophylaxis of disorders associated with neuroinflammatory diseases such as stroke, spinal cord injury, multiple sclerosis, Alzheimer's disease, Parkinson's disease, amyotrophic lateral sclerosis and/or inflammatory disorders such as inflammatory pain, as rheumatoid arthritis, irritable bowel syndrome, inflammatory bowel disease.

The compounds are useful for the treatment or prophylaxis of asthma, female sexual dysfunction, male erectile dysfunctions and over-active bladder syndrome, cancer and tumor metastasis, viral and bacterial infections, insulin resistance and diabetes. The invention therefore provides for the use of a compound of formula (I) and/or physiologically acceptable salts thereof for use in therapy and in particular for use as a medicine for inhibiting the effects of Rho kinases-1 and/or -2.

The invention also provides for the use of a compound of formula (I) and/or a physiologically acceptable derivative or salt thereof for the manufacture of a medicament for inhibiting the effects of Rho kinase-1/2.

The invention also provides for a method for inhibiting the effects of the Rho kinase-1/2 in a mammal e.g. a human, comprising administering to a patient in need thereof an effective amount of a compound of formula (I) and/or a physiologically acceptable derivative or salt thereof. According to a further aspect, the invention also provides for a method for inhibiting the effects of the kinases Msk-1 and/or Rho kinase-1/2 in a mammal e.g. a human, comprising administering to a patient in need thereof an effective amount of a compound of formula (I) and/or a physiologically acceptable derivative or salt thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated, the route of administration and the age and the condition of the patient and will be ultimately at the discretion of the attendant physician. In general however doses employed for adult human treatment will typically be in the range of 5 to 800 mg per day, dependent upon the route of administration.

Preferred routes of administration include by intravenous injection or orally.

Thus for parenteral administration a daily dose regimen will typically be in the range 0.1 to 80 mg/kg of the total body weight, preferably from about 0.2 to 30 mg/kg or more preferably 0.5 to 15 mg/kg. For oral administration a daily dose regimen will typically be within the range range 0.1 to 80 mg/kg of the total body weight, preferably from about 0.2 to 30 mg/kg or more preferably 0.5 to 15 mg/kg.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant or rectal administration. Appropriate dosage forms for adminisration by each of these routes may be prepared by conventional techniques.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

Conveniently the compounds of the invention are formulated for intravenous or oral administration.

The compositions according to the invention may contain between 0.1-99% of the active ingredient, conveniently from 30-95% for tablets and capsules and 3-50% for liquid preparations.

Compounds of formula (I) wherein $R_1$ is a group (a), (c) and (d) may be prepared by reacting the diamine (II)

(II)

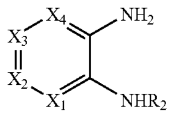

wherein $R_2$, $X_1$, $X_2$, $X_3$ and $X_4$ have the meanings defined in (I) with the appropriate compound of formula (III), (IV) or (V)

(III)

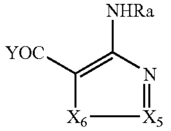

(IV)

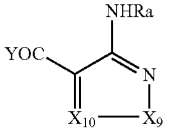

(V)

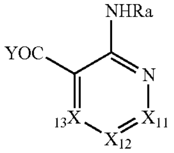

wherein Y is hydrogen, halogen e.g. Cl, Br or I, hydroxy or $C_{1-4}$alkoxy, Ra is hydrogen or a nitrogen protecting group such as an alkoxycarbonyl or benzyloxycarbonyl group and each of $X_5$, $X_6$, $X_9$, $X_{10}$, $X_{11}$, $X_{12}$ and $X_{13}$ have the meanings as defined in formula (I) or is a group available thereto, followed when required by removal of the nitrogen protecting group Ra using conventional methods.

When Y is a group selected from halogen, alkoxy or hydroxy the reaction is carried out with heating and optionally in the presence of a solvent and/or a dehydrating agent such as polyphosphoric acid.

When Y is hydrogen the reaction is conveniently carried out in the presence of an oxidant such as sodium bisulphite.

Compounds of formula (I) wherein R, is the group (b) may be prepared by reduction of the corresponding nitro derivative (VI)

(VI)

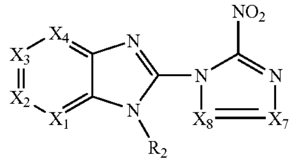

wherein $R_2$, $R_3$, $R_3$, $X_1$, $X_2$, $X_3$, $X_4$, $X_7$ and $X_8$ have the meanings defined in formula (I).

The reduction may be effected using conventional procedures for converting a nitro group into an amino group, thus for example, the reduction may be effected using hydrogen and a suitable metal catalyst e.g. palladium.

Compounds of formula (I) wherein $R_1$ is the group (c) and $X_9$ is oxygen and $X_{10}$ is nitrogen may be prepared by reacting the nitrile (VII)

(VII)

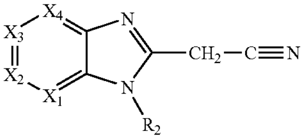

wherein $R_2$, $X_1$, $X_2$, $X_3$ and $X_4$ have the meanings defined in formula (I) with hydrochloric acid and sodium nitrite in a solvent such as an alkanol and treatment of the product thus formed with a base e.g. aqueous sodium hydroxide and hydroxylamine and subsequent heating.

Compounds of formula (I) wherein $R_1$ represent the group (c) wherein $X_9$ is NH and $X_{10}$ is CH may be prepared by reacting compound (VII)

(VIII)

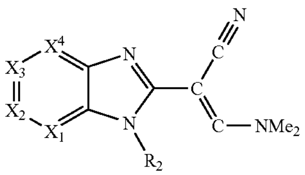

wherein $R_2$, $X_1$, $X_2$, $X_3$ and $X_4$ have the meanings defined in formula (I) with hydrazine. This reaction is preferably carried out in a solvent e.g. an alkanol such as methanol and with heating.

In another aspect of the invention compounds of formula (I) may be converted into other compounds of formula (I). Thus N-oxides of compounds of formula (I) may be prepared by treating a compound of formula (I) with a peroxy acid such as hydrogen peroxide in acetic acid.

For example reactions of a compound of formula (I) wherein $X_2$ or $X_3$ is N may be converted into the corresponding N-oxide i.e. $X_2$ or $X_3$ is N═O by reaction with hydrogen peroxide in acetic acid.

A compound of formula (I) wherein $R_4$ or $R_6$ is halogen e.g. chlorine or bromine may be prepared from the of formula (I) wherein $X_2$ is N═O and $X_1$, is CH or $X_3$ is N═O and $X_4$ is CH by reaction with the appropriate phosphorus oxyhalide e.g. phosphorus oxychloride or oxybromide.

Compounds of formula (I) wherein $R_6$ is alkoxy e.g. methoxy may be prepared by treating the corresponding compound wherein $R_6$ is halogen e.g. chlorine or bromine with the appropriate alkanol e.g. methanol in the presence of a base such as sodium hydroxide.

Compounds of formula (I) wherein $R_3$ or $R_6$ is an optionally substituted aryl e.g. optionally substituted phenyl group or an optionally substituted heteroaryl group may be prepared by treating the corresponding compound wherein $R_3$ and or $R_6$ is halogen e.g. chlorine or bromine by reaction with the corresponding optionally substituted aryl or heteroarylboronic acid in the presence of a suitable palladium catalyst e.g. bis(triphenylphosphine)palladium(II) dichloride or tetrakis(triphenylphosphine)palladium(0) or 1,1-bis (triphenylphosphono)ferrocene dichloropalladium(II) chloroform complex and a base e.g. sodium carbonate. The reaction is preferably carried out in a solvent e.g. hydrocarbon such as toluene or ether such as 1,2-dimethoxyether or an amide such as DMF and with heating.

Compounds of formula (I) wherein $R_3$ is a group $R_{19}S$ or $R_{19}NH$ and wherein $R_{19}$ is an optionally substituted aryl e.g. optionally substituted phenyl group or an optionally substituted heteroaryl group may be prepared by treating the corresponding compound wherein $R_3$ is halogen e.g. bromine with the corresponding thiol $R_{19}SH$ or amine $R_{19}NH_2$ in the presence of a suitable palladium catalyst e.g. Tris (dibenzylidene-acetone)dipalladium and racemic-2,2'-Bis (diphenylphosphino)-1,1'-binaphthyl The reaction is preferably carried out in a solvent e.g. an ether such as dioxane with heating.

Compounds of formula (I) wherein $R_3$ is a group the group $SO_2NR_{14}R_{15}$ may be prepared by treating the corresponding compound wherein $R_3$ is halogen e.g. bromine with the sodium hydride and then n-butyllithium and the treating the resultant product sequentially with sulphur dioxide, sulphuryl chloride and then the amine $HNR_{14}R_{15}$. The reaction is conveniently carried out in a solvent such as tetrahydrofuran.

Compounds of formula (I) wherein $R_6$ is an alkyl group e.g methyl may be prepared by treating the corresponding compound wherein $R_6$ is halogen e.g. bromine by reaction with the corresponding trialkylaluminium in the presence of bis(triphenylphosphine)palladium(II) dichloride. The reaction is preferably carried out in a solvent e.g. 1,4 dioxan and with heating.

Compounds of formula (I) in which $R_2$ and/or $R_3$ contain a phenyl group substituted by a methoxy group, as a substituent or part of a substituent may be converted into the corresponding compound of formula (I) wherein the phenyl group is substituted by hydroxy, by reaction with boron tribromide in a suitable solvent such as dichloromethane.

Compounds of formula (I) wherein $R_2$ is a phenyl group substituted by an optionally substituted alkoxy group e.g. a dialkylaminoalkoxy group may be prepared by reacting the corresponding compound of formula (I) wherein $R_2$ is a phenyl group substituted by hydroxy with a suitable base e.g. sodium hydride in an aprotic solvent such as dimethylformamide and then the appropriate optionally substituted alkylhalide e.g. dialklaminoalkylhalide.

Compounds of formula (I) wherein $R_3$ is bromine may be converted into the corresponding wherein $R_3$ is formyl by reaction with n-butyllithium and dimethylformamide in a solvent such as tetrahydrofuran followed by quenching with water.

Compounds of formula (I) wherein $R_3$ is carboxyl may be prepared from the corresponding compound of formula (I) wherein $R_3$ is bromine by reaction with lithium disopropylamide and then butyl lithium in hexanes followed by treatment with carbon dioxide gas. The reaction is preferably carried out at a low temperature e.g. −78° C.

Compounds of formula (I) wherein $R_3$ is a methyl group substituted by a group selected from $R_{19}NH$, $R_{19}R_{20}N$, or an N linked, 4-7 membered heterocyclic group (containing one or two hetero atoms selected from N, O or S(O)n), may be prepared by reaction of the corresponding compound wherein $R_3$ is formyl with the appropriate amine $R_{19}NH_2$, $R_{19}R_{20}NH$ or 4-7 membered heterocycle under reductive alkylation conditions. For example using a cyanoborohydride in a suitable solvent e.g. methanol. In this reaction if the groups $R_{19}$, $R_{20}$ or the 4-7 membered heterocycle contains an additional primary or secondary amino group then it is desirable to protect these using a conventional nitrogen protecting group such as a t-butyloxycarbonyl which may then be deprotected if so required.

Compounds of formula (I) wherein $R_2$ or $R_3$ is phenyl substituted by amino methyl and wherein the amino group refers to a group $R_{19}NH$, $R_{19}R_{20}N$ or an N linked 4-7 membered heterocyclic group containing one or two heteatoms selected from N, O or S(O)n may be prepared by reacting the corresponding compound wherein $R_2$ or $R_3$ is phenyl substituted by CHO under conventional reductive alkylation conditions such as those described above for preparing compounds wherein $R_3$ is methyl substituted by $R_{19}NH$ or $R_{19}R_{20}N$. The compounds of formula (I) wherein $R_2$ is phenyl substituted by CHO may br prepared in situ from the corresponding compound wherein $R_2$ is phenyl substituted by halogen e.g. bromine by reaction with n-butyllithium and dimethylformamide in a solvent such as tetrahydrofuran followed by quenching with water.

Compounds of formula (I) wherein $R_3$ is the group $CONR_{14}R_{15}$ and $R_{14}$ and $R_{15}$ have the meanings defined in formula (I) may be prepared from the corresponding compounds of formula (I) wherein $R_3$ is carboxyl by reaction with the amine $HNR_{14}R_{15}$ wherein $R_{14}$ and $R_{15}$ have the meanings defined in formula (I) or are protected derivatives thereof under conventional procedures for preparing amides from acid followed by removal of the said protecting groups.

Conventionally the reaction is carried out by treating the acid with carbonyldimidiimidazole in a suitable solvent such as DMF followed by reaction with the amine $HNR_{14}R_{15}$.

Compounds of formula (I) wherein $R_3$ is hydroxyl may be prepared from the corresponding compound wherein $R_3$ is halogen e.g. bromine by reaction with n-butyl lithium in a solvent such as tetrahydrofuran or hexanes and tetrahydrofuran followed by addition of a trialkyl borate such as trimethylborate. The reaction is preferably carried out at low temperatures e.g. 78° C. and then allowed to reach room temperature before being quenched by aqueous sodium hydroxide followed by aqueous hydrogen peroxide.

Compounds of formula (I) wherein $R_3$ is the group $R_{19}O$ and wherein $R_{19}$ has the meaning defined in formula (I) hydroxyl may be prepared from the corresponding compound wherein $R_3$ is hydroxyl by reaction with a group $R_{19}La$ wherein $R_{19}$ has the meaning defined in formula (I) is a protected derivative thereof and La is a leaving group. Thus La can be a halogen group e.g. bromines or iodine, or a hydroxyl which can be converted into a leaving group insitu e.g. by reaction with tributylphosphine and azodicarbonyl) dipiperidine.

Compounds of formula (I) wherein $R_3$ is an optionally substituted ethenyl grouping may be prepared by a compound of formula (I) wherein $R_3$ is bromine by reaction with the appropriate ethene derivative in the presence of palladium acetate, or tolyltriphenylphosphine and a teritary organic base such as triethylamine.

Compounds wherein $R_3$ is an optionally substituted ethyl group may be prepared by treating the corresponding compound of formula (I) wherein $R_3$ is halogen e.g. bromine by reaction with the corresponding optionally substituted ethenyl compound in the presence of 9-borobicyclo[3,3.1]-nonane and 1,1 bis(diphenylphosphono ferrocene dichloro palladium complex in a suitable solvent such as tetrahydrofuran and or dichloromethane.

In the above synthesis of compounds of formula (I) wherein they contain a primary or secondary amino grouping it may be necessary or desirable to carry out these procedures wherein the primary or secondary amine is in a protected form e.g. as a carbamate e.g. a t-butyl carbamate and then the carbamate converted into the required amine by conventional procedures, for example by the reaction with trifluoroacetic acid.

The nitrile of formula (VII) may be prepared by heating of a compound of formula (II) with ethyl cyanoacetate.

The compound of formula (VIII) may be prepared by reacting the nitrile of formula (VII) with an acetal of N,N dimethylformamide in a solvent e.g. a hydrocarbon such as ortho xylene and with heating.

Compounds of formula (VI) may be prepared by reaction of the 2-iodo-imidazole derivative (IX)

(IX)

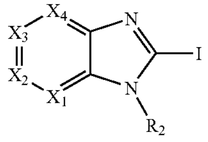

wherein $R_2$, $X_1$, $X_2$, $X_3$ and $X_4$ have the meanings defined in formula (I) with the compound (X)

(X)

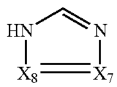

wherein $X_7$ and $X_8$ have the meanings defined in formula (I) in the presence of a base and a polar aprotic solvent and then reacting the resultant compound (XI)

(XI)

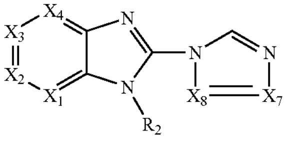

with an alkyl nitrite in the presence of a suitable base.

Compounds of formula (II) may be prepared by reacting a compound of formula (XII)

(XII)

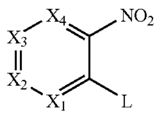

wherein $X_1$, $X_2$, $X_3$ and $X_4$ have the meanings defined above and L is a group displaceable by the amine $R_2NH_2$ e.g. methoxy, bromine, chlorine, fluorine or methoxysulphonyl to give the nitro amine (XIII)

(XIII)

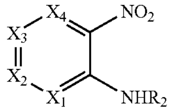

followed by reduction of the nitro group by conventional means, for example using hydrogen and a palladium catalyst, iron and an organic acid e.g. acetic acid or with sodium dithionate.

When compounds of formula (I) contain an asymmetric centre the specific enantiomers arising there from may be obtained by conventional procedures. For example using preparative high performance liquid chromatography (HPLC) with a chiral stationary phase.

Physiologically acceptable acid addition salts of the compounds of formula (I) may be prepared by conventional procedures, for example by addition of a solution of the inorganic or organic acid in a suitable solvent e.g. an alkanol or an ether to a solution of the free base in a solvent such as an alkanol, e.g. methanol or an ether e.g. diethyl ether or tetrahydrafuran.

The compounds of formula (III), (IV), (V) (IX), (X) and (XII) are either known compounds or may be prepared by analogous methods to those preparing the known compounds.

The following examples are illustrative of the present invention and are not to be construed as a limitation of the scope of the invention.

EXAMPLE 1

4-(1-Ethyl-1H-imidazo[4,5-c]pyridin-2-yl)furazan-3-ylamine

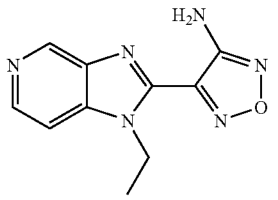

Step 1. Ethyl-(3-nitropyridin-4-yl)amine

4-Methoxy-3-nitropyridine hydrochloride (11.2 g, 58.9 mmol) in ethanol (75 ml) was treated with a 70% solution of ethylamine in water (32 ml) and heated under reflux for 1 hour. Further ethylamine solution (32 ml) was added and the mixture heated under reflux for a further 2 hours. After cooling to room temperature, the solvent was removed in vacuo and the residue dissolved in ethyl acetate, washed (x3) with water and saturated aqueous sodium chloride solution, dried over sodium sulphate and concentrated in vacuo to afford the title compound (8.7 g, 88%); MS (ES+) m/e 168 $[M+H]^+$.

Step 2. $N^4$-Ethylpyridine-3,4-diamine

The product from Step 1 (8.7 g, 52.0 mmol) in ethanol (150 ml) was hydrogenated for 18 hours in the presence of 10% palladium on carbon. After filtration of the catalyst through Kieselguhr, the filtrate was concentrated in vacuo to afford the title compound (6.7 g, 94%); MS (ES+) m/e 138 $[M+H]^+$.

Step 3. (1-Ethyl-1H-imidazo[4,5-c]pyridin-2-yl)acetonitrile

The product from Step 2 (500 mg, 3.6 mmole) and ethyl cyanoacetate (620 mg, 5.5 mmol) were heated together at 190° C. for 20 minutes. After cooling to room temperature, the residue was purified by column chromatography eluting with 10% methanol in ethyl acetate to afford the title compound (250 mg, 37%); MS (ES+) m/e 187 $[M+H]^+$.

Step 4. 4-(1-Ethyl-1H-imidazo[4,5-c]pyridin-2-yl)furazan-3-ylamine

The product from Step 3 (200 mg, 1.1 mmol) in methanol (4 ml) and 2N hydrochloric acid (4 ml) was treated portionwise with sodium nitrite (150 mg, 2.2 mmol) and stirred at room temperature for 2 hours. The pH of the mixture was adjusted to 12 by addition of 50% sodium hydroxide solution and a 50% solution of hydroxylamine in water (3 ml) was added. The mixture was heated at 90° C. for 2.5 hours and the reaction allowed to cool to room temperature. The resulting precipitate was filtered and dried in vacuo to afford the title compound (110 mg, 43%); MS (ES+) m/e 231 $[M+H]^+$.

EXAMPLE 2

4-(1-Cyclopropyl-1H-imidazo[4,5-c]pyridin-2-yl) furazan-3-ylamine

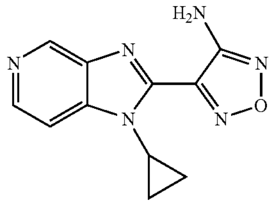

Step 1. Cyclopropyl-(3-nitropyridin-4-yl)amine

4-Methoxy-3-nitropyridine hydrochloride (2.0 g, 11.3 mmol) and cyclopropylamine (1.6 ml, 22.6 mmol) in ethanol (5 ml) was treated with triethylamine (1.7 ml, 12.4 mmol) and heated under reflux for 18 hours. After cooling to room temperature, the solvent was removed in vacuo and the residue dissolved in dichloromethane, washed with water and saturated aqueous sodium chloride solution, dried over magnesium sulphate and concentrated in vacuo to afford the title compound (1.7 g, 84%); MS (AP+) m/e 180 $[M+H]^+$.

Steps 2. 4-(1-Cyclopropyl-1H-imidazo[4,5-c]pyridin-2-yl) furazan-3-ylamine

The title compound was prepared from the product of Step 1 using the methods of Example 1 Steps 2-4; MS (AP+) m/e 243 $[M+H]^+$.

The following examples were prepared by the general two-step method described in Example 2.

| | Example | Amine | Characterisation |
|---|---|---|---|
| 3 | 4-(1-Methyl-1H-imidazo[4,5-c]pyridin-2-yl)furazan-3-ylamine | Methylamine (8M in ethanol) | MS(AP+) m/e 217 $[M + H]^+$ |
| 4 | 4-(1-Cyclohexyl-1H-imidazo[4,5-c]pyridin-2-yl)furazan-3-ylamine | Cyclohexylamine | MS (ES+) m/e 285 $[M + H]^+$. |
| 5 | 4-(1-Cyclopropylmethyl-1H-imidazo[4,5-c]pyridin-2-yl)furazan-3-ylamine | Cyclopropylmethylamine | MS(AP+) m/e 257 $[M + H]^+$ |
| 6 | 4-(1-Cyclohexylmethyl-1H-imidazo[4,5-c]pyridin-2-yl)furazan-3-ylamine | Cyclohexylmethylamine | MS(AP+) m/e 299 $[M + H]^+$ |
| 7 | 4-(1-Cyclobutyl-1H-imidazo[4,5-c]pyridin-2-yl)furazan-3-ylamine | Cyclobutylamine | MS(AP+) m/e 257 $[M + H]^+$ |
| 8 | 4-[1-(2-Ethylbutyl)-1H-imidazo[4,5-c]pyridin-2-yl)furazan-3-ylamine | 2-Ethyl-N-butylamine | MS(AP+) m/e 288 $[M + H]^+$ |
| 9 | 4-(-Isopropyl-1H-imidazo[4,5-c]pyridin-2-yl)furazan-3-ylamine | Isopropylamine | MS(AP+) m/e 245 $[M + H]^+$ |
| 10 | 4-(1-sec-Butyl-1H-imidazo[4,5-c]pyridin-2-yl)furazan-3-ylamine | sec-Butylamine | MS(AP+) m/e 259 $[M + H]^+$ |
| 11 | 4-(1-Cyclopentyl-1H-imidazo[4,5-c]pyridin-2-yl)-furazan-3-ylamine | Cyclopentylamine | MS(AP+) m/e 271 $[M + H]^+$ |
| 12 | 4-(1-Cycloheptyl-1H-imidazo[4,5-c]pyridin-2-yl-furazan-3-ylamine | Cycloheptylamine | MS(AP+) m/e 299 $[M + H]^+$ |
| 13 | 4-[1-(2-Dimethylamino-1-methylethyl)-1H-imidazo[4,5-c]pyridin-2-yl)furazan-3-ylamine | $N^1$,$N^1$-Dimethyl-1,2-propanediamine | MS(AP+) m/e 288 $[M + H]^+$ |
| 14 | 4-(1-Piperidin-4-yl)-1H-imidazo[4,5-c]pyridin-2-yl-furazan-3-ylamine | 4-Amino-piperidine-1-carboxylic acid tert-butyl ester | MS(AP+) m/e 286 $[M + H]^+$ |
| 15 | 4-[1-(4-Diethylamino-1-methyl-butyl)-1H-imidazo[4,5-c]pyridin-2-yl]-furazan-3-ylamine | 2-amino-5-diethylamino pentane | MS (AP+) m/e 344 $[M + H]^+$ |
| 16 | {4-[2-(4-Amino-furazan-3-yl)-imidazo[4,5-c]pyridin-1-yl]-butyl}-carbamic acid tert-butyl ester | (4-Amino-butyl)-carbamic acid tert-butyl ester | MS (ES+) m/e 374$[M + H]^+$ |
| 17 | 4-[1-(3-Dimethylamino-propyl)-1-H-imidazo[4,5-c]pyridin-2-yl]-furazan-3-ylamine | $N^1$,$N^1$-Dimethyl-propane-1,3-diamine (Monatsh. Chem. 112, 825-840 (1981)) | MS (ES+) m/e 288 $[M + H]^+$. |
| 18 | 4-{1-[2-(4-Methyl-piperazin-1-yl)-ethyl]-1-H-imidazo[4,5-c]pyridin-2-yl}-furazan-3-ylamine | 2-(4-Methyl-piperazin-1-yl)-ethylamine (J. Med. Chem. 42 (15) 2870-2880 (1999)) | MS (ES+) m/e 329 $[M + H]^+$. |

EXAMPLES 19 AND 20

(+)-4-[1-(2-Dimethylamino-1-methylethyl)-1H-imidazo[4,5-c]pyridin-2-yl)furazan-3-ylamine and (−)-4-[1-(2-Dimethylamino-1-methylethyl)-1-H-imidazo [4,5-c]pyridin-2-yl)furazan-3-ylamine The racemic product of Example 13 was separated into the title enantiomeric forms by preparative LC using Chiralcel OD, 10 micron particle size; 250 mm×4.6 mm i.d.; n-Hexane: Ethanol, 99.7% v/v–100% v/v (80:20 v/v); 1.0 ml/min; UV detection at 215 nm yielding the (+) enantiomer [α]D+6.8°; HPLC tR 8.2 min and the (−) enantiomer [α]D−2.2°; HPLC tR 9.0 min.

EXAMPLE 21

4-[1-(4-Amino-butyl)-1H-imidazo[4,5-c]pyridin-2-yl]4-furazan-3-ylamine

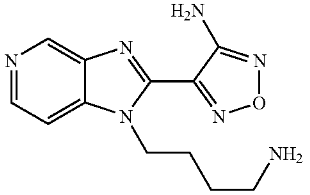

A solution of the product of Example 16 (155 mg, 0.415 mmol) in anhydrous dichloromethane (4 ml) was treated with trifluoroacetic acid (4 ml), and stirred at room temperature for 0.5 hours. The solvent was evaporated in vacuo and the residue partitioned between dichloromethane and saturated sodium bicarbonate solution. The organic phase was washed with water (×3), and dried over anhydrous sodium sulphate, and the solvent evaporated in vacuo. The residue was purified by silica gel chromatography eluting with a mixture of 0.880 ammonia:methanol:dichloromethane (1:9:90) to afford the title product (52 mg, 46%). MS (ES+) m/e 274 $[M+H]^+$.

The following compounds were prepared by the methods of Example 2 followed by the method of example 21:

| Example | | Amine | Characterisation |
|---|---|---|---|
| 22 | 4-(1-(1-Pyrrolidin-3-yl-1-H-imidazo[4,5-c]pyridin-2-yl)-furazan-3-ylamine | 3-amino-pyrrolidine-1-carboxylic acid tert-butyl ester (Syn. Comm. 2357-60 (1992) | MS (ES+) m/e 272 $[M + H]^+$. |
| 23 | 4-[1-(5-Amino-pentyl)-1-H-imidazo[4,5-c]pyridin-2-yl]-furazan-3-ylamine | (5-Amino-pentyl)-carbamic acid tert-butyl ester (J. Med. Chem. 32(2) 391-396 (1989)) | MS (ES+) m/e 288 $[M + H]^+$. |
| 24 | 4-[1-(3-Amino-propyl)-1-H-imidazo[4,5-c]pyridin-2-yl]-furazan-3-ylamine | (3-Amino-propyl)-carbamic acid tert-butyl ester(J. Org. Chem. 57(21)5687-5692 (1992)) | MS (ES+) m/e 259 $[M + H]^+$. |

EXAMPLE 25

4-(1-Piperidin-3-yl-1H-imidazo[4,5-c]pyridin-2-yl) furazan-3-ylamine

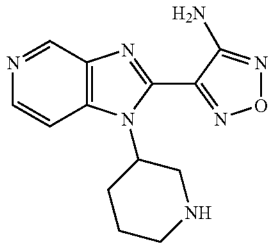

Step 1. 3-(3-Nitro-pyridin-4-ylamino-piperidine-1-carboxylic acid tert-butyl ester 4-Chloro-3-nitropyridine (1.1 g, 6.99 mmol) in ethanol (12 ml) was treated with 3-Amino-piperidine-1-carboxylic acid tert-butyl ester (2.8 g, 13.9 mMol) followed by sodium acetate (0.57 g, 6.99 mMol) and heated under reflux for 2 hours. After cooling to room temperature, the solvent was removed in vacuo and the residue dissolved in ethyl acetate, washed (×3) with water dried over magnesium sulphate and concentrated in vacuo to afford the title compound (2.1 g, 94%); MS (ES+) m/e 323 $[M+H]^+$.

Step 2. 4-(1-Piperidin-3-yl-1H-imidazo[4,5-c]pyridin-2-yl) furazan-3-ylamine

The title compound was prepared from the product of step 1 using the method of example 1 Steps 2 to 4, then example 21. MS (ES+) m/e 286 $[M+H]^+$.

The following compound was synthesised using the same 2-step procedure used to make example 25.

| | Name | Amine | Data |
|---|---|---|---|
| 26 | 4-[1-(2-Piperazin-1-yl-ethyl)-1-H-imidazo[4,5-c]pyridin-2-yl]-furazan-3-ylamine | from 4-(2-Aminoethyl)-piperazine-1-carboxylic acid benzyl ester (J. Med. Chem. 30(1) 121-131 (1987) | MS (ES+) m/e 315 $[M + H]^+$. |

EXAMPLES 27 AND 28

(+)-4-(1-Piperidin-3-yl-1H-imidazo[4,5-c]pyridin-2-yl)furazan-3-ylamine and (−)-4-(1-Piperidin-3-yl-1H-imidazo[4,5-c]pyridin-2-yl)furazan-3-ylamine The racemic product of Example 25 was separated into the title enantiomeric forms by preparative LC using Chiralpak AD, 10 micron particle size; 250 mm×20 mm i.d.; n-Hexane: Ethanol, (50:50 v/v; pre-mixed); 17 m/min; UV detection at 215 nm yielding the (+) enantiomer [α]D+0.4°; HPLC tR 6.6 min and the (−) enantiomer [α]D−3.2°; HPLC tR 7.7 min.

EXAMPLE 29

4-(1-Piperidin-4-ylmethyl-1H-imidazo(4,5-c)pyridi-2-yl)-furazan-3-ylamine

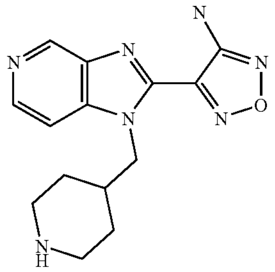

Step 1. 4-((3-Nitro-pyridin-4-ylamino)-methyl)-piperidine-1-carboxylic acid tert-butyl ester 4-Methoxy-3-nitropyridine hydrochloride (2.26 g, 11.9 mmol) in ethanol (15 ml) was treated with 4-aminomethyl-piperidine-1-carboxylic acid tert-butyl ester (3.05 g, 14.2 mMol) followed by triethylamine (1.82 ml, 13.1 mMol) and heated under reflux for 6 hours. After cooling to room temperature, the solvent was removed in vacuo and the residue dissolved in ethyl acetate, washed (×3) with water, brine, dried over sodium sulphate and concentrated in vacuo to afford the title compound (2.78 g, 77%); $^1$H NMR (400 MHz) δ 9.21 (1H (s) Ar—H), δ 8.30 (1H, (d) Ar—H), δ 8.2 (1H, (s) N—H) δ 6.70 (1H, (d) Ar—H), δ 4.04 (2H (broad), $CH_2$) δ 3.25 (2H, (t) piperidine) δ 2.73 (2H, (broad) piperidine), δ 1.79 (1H, (broad) piperidine), δ 1.46 (9H, (s) $^t$Bu).

Steps 2. 4-(1-Piperidin-4-ylmethyl-1H-imidazo(4,5-c)pyridi-2-yl)-furazan-3-ylamine The title compound was prepared from the product of step 1 according to the method of example 1 steps 2-4, followed by the method of example 21. MS (ES+) m/e 300 $[M+H]^+$.

EXAMPLE 30

4-[1-(4-Methoxy-phenyl)-1H-imidazo[4,5-c]pyridin-2-yl]-furazan-3-ylamine

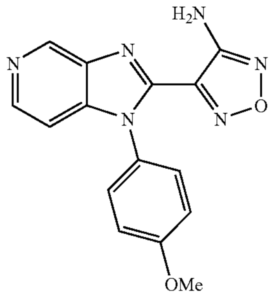

Step 1: (4-Methoxy-phenyl)-(3-nitro-pyridin-4-yl)-amine

To a solution of 4-chloro-3-nitropyridine (Kruger J, Mann F. G, *J. Chem. Soc.,* 1955, 2755) (700 mg, 4.41 mmol) in ethanol (10 ml) was added 4-methoxyaniline (1.087 g, 8.82 mmol), followed by sodium acetate (362 mg, 4.41 mmol). The mixture was heated under reflux for 16 hours, cooled to room temperature and diluted with water (30 ml). The resulting precipitate was collected by filtration, washed with water (×3) and dried in vacuo to afford the title compound (800 mg, 74%); MS (ES+) m/e 309 $[M+H]^+$.

Step 2: 4-[1-(4-Methoxy-phenyl)-1H-imidazo[4,5-c]pyridin-2-yl]-furazan-3-ylamine The title compound was prepared from the product of Step 1 using the methods of Example 1 Step 2-4; MS (AP+) m/e 309 $[M+H]^+$.

The following examples were prepared by the general two-step method described in Example 30.

| | Example | Aniline | Characterisation |
|---|---|---|---|
| 31 | 4-(1-Phenyl-1H-imidazo[4,5-c]pyridin-2-yl)-furazan-3-ylamine | Aniline | MS (ES+) m/e 279 $[M + H]^+$ |
| 32 | 4-[1-(4-Amino-phenyl)-1H-imidazo[4,5-c]pyridin-2-yl]-furazan-3-ylamine | 4-amino acetanilide | MS (ES+) m/e 294 $[M + H]^+$ |
| 33 | 4-[1-(3-Methoxy-phenyl)-1H-imidazo[4,5-c]pyridin-2-yl]-furazan-3-ylamine | 3-methoxy aniline | MS (ES+) m/e 309 $[M + H]^+$ |
| 34 | 4-[1-(2-Methoxy-phenyl)-1H-imidazo[4,5-c]pyridin-2-yl]-furazan-3-ylamine | 2-methoxy aniline | MS (ES+) m/e 309 $[M + H]^+$ |
| 35 | 4-[1-(2-Ethyl-phenyl)-1H-imidazo[4,5-c]pyridin-2-yl]-furazan-3-ylamine | 2-ethyl aniline | MS (ES+) m/e 307 $[M + H]^+$ |

EXAMPLE 36

4-[1-(3-Chloro-phenyl)-1H-imidazo[4,5-c]pyridin-2-yl]-furazan-3-ylamine

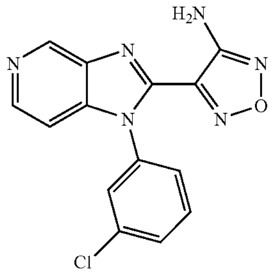

Step 1: (3-Chloro-phenyl)-(3-nitro-pyridin-4-yl)-amine

The title compound was prepared from 3-chloro aniline using the procedures detailed in Example 30 Step 1.

Step 2: N4-(3-Chloro-phenyl)-pyridine-3,4-diamine

The product of Step 1 (325 mg, 1.302 mmol), was dissolved in ethanol (20 ml), and treated with iron powder (727 mg, 13.017 mmol), 20 drops of 37%. hydrochloric add and water (2 ml), and refluxed for 1 hour. The reaction was then filtered hot, and the filtrate evaporated in vacuo. The residue was dissolved in ethyl acetate then washed with saturated sodium bicarbonate solution, water, and brine, separated, dried over anhydrous sodium sulfate and evaporated in vacuo to afford the title compound (253 mg, 88%). MS (ES+), m/e 220/222 $[M+H]^+$.

Step 3: 4-[1-(3-Chloro-phenyl)-1H-imidazo[4,5-c]pyridin-2-yl]-furazan-3-ylamine

The title product was prepared using the general method described in Example 1 Step 3-4; MS (ES+), m/e 313/315 $[M+H]^+$.

The following example was prepared by the general 3 step method described in example 36.

| | | | |
|---|---|---|---|
| 37 | 4-[1-(3-bromo-phenyl)-1H-imidazo[4,5-c]pyridin-2-yl]-furazan-3-ylamine | 3-bromo aniline | MS (ES+) m/e 357/359 $[M + H]^+$ |

EXAMPLE 38

4-[2-(4-Amino-furazan-3-yl)-imidazo[4,5-c]pyridin-1-yl]-phenol

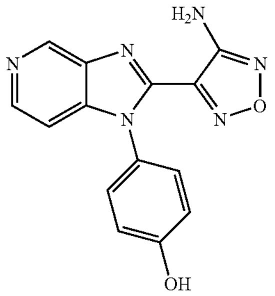

To a solution of the product of Example 30 (100 mg, 0.32 mmol) in anhydrous dichloromethane (1.0 ml) stirred at 0° C., was added dropwise a 10M solution of boron tribromide (2.91 ml, 2.92 mmol) in dichloromethane and the mixture stirred at room temperature for 16 hours. The reaction was then quenched with water (20 ml), and the pH adjusted to 14 with 50% sodium hydroxide solution. The aqueous phase was washed with dichloromethane (×3), neutralised with 5N hydrochloric acid, and the resulting precipitate collected, washed with water (×3), diethyl ether and dried in vacuo to yield the title compound (59 mg, 62%); MS (ES+) m/e 295 $[M+H]^+$.

EXAMPLE 39

3-[2-(4-Amino-furazan-3-yl)-imidazo[4,5-c]pyridin-1-yl]-phenol

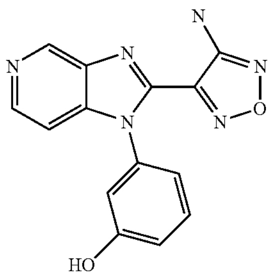

The title compound was prepared from the product of Example 33 using the procedure detailed in Example 38.

EXAMPLE 40

4-[1-(3-Pyrrolidin-1-ylmethyl-phenyl)-1H-imidazo[4,5-c]pyridin-2-yl]-furazan-3-ylamine

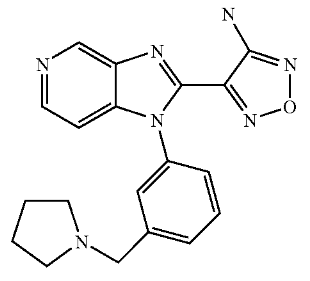

Step 1: 3-[2-(4-Amino-furazan-3-yl)-imidazo[4,5-c]pyridin-1-yl]-benzaldehyde

The product of Example 37 (1.07 g, 3 mmol) in anhydrous tetrahydrofuran at −78° C. was treated dropwise with a 2.5M solution of n-butyllithium (3.6 ml, 9 mmol) in hexanes, followed by anhydrous dimethylformamide (10 ml) and stirred for 10 minutes. The reaction was then warmed to room temperature, quenched with water and extracted with dichloromethane (×3). The combined organic phase was washed with water, brine, dried over anhydrous sodium sulfate and evaporated in vacuo. The residue was purified using silica gel chromatography, eluting with a mixture of ethyl acetate/pentane (3:1) to afford the title compound (75 mg, 8%); MS (ES+), m/e 307 $[M+H]^+$.

Step 2: 4-[1-(3-Pyrrolidin-1-ylmethyl-phenyl)-1H-imidazo[4,5-c]pyridin-2-yl]-furazan-3-ylamine The product of Step 1 was stirred in 1,2-dichloroethane, and treated with pyrrolidine (27 uL, 0.326 mmol) and stirred for 15 minutes at room temperature. The reaction was then treated with sodium triacetoxyborohydride (34 mg, 0.164 mmol) and stirred at room temperature for 16 hours. The reaction was diluted with methanol and applied to a Mega Bond Elute SCX ion exchange column, eluting sequentially with water, methanol and finally 0.880 ammonia:methanol (1:9). The residue was purified using silica gel chromatography eluting with a mixture of 0.880 ammonia:methanol: dichloromethane (1:9:90) to afford the compound (20 mg, 34%); MS (ES+), m/e 362 $[M+H]^+$.

EXAMPLE 41

4-{1-[4-(2-Dimethylamino-ethoxy)-phenyl]-1H-imidazo[4,5-c]pyridin-2-yl}-furazan-3-ylamine hydrochloride

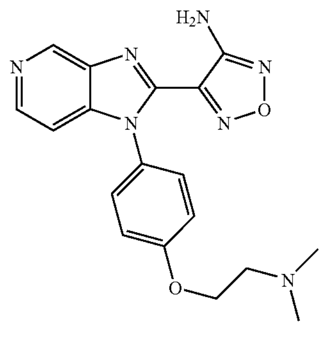

To a solution of the product of Example 38 (30 mg, 0.102 mmol), in N,N-dimethylformamide (2 ml), was added sodium hydride (60% dispersion in mineral oil, 4 mg, 0.10 mmol). After 5 minutes at room temperature 2-(dimethylamino)ethyl chloride hydrochloride (15 mg, 0.102 mmol) and sodium hydride (60% dispersion in mineral oil, 4 mg, 0.102 mmol) were added and the reaction heated at 60° C. for 5 hours. The solvent was evaporated in vacuo and the residue was partitioned between ethyl acetate and 2M sodium hydroxide solution. The organic phase was separated then washed with water (×3), dried over anhydrous sodium sulphate and evaporated in vacuo. Purification of the residue by silica gel chromatography eluting with 10% methanol in dichloromethane gave the free base of the title compound. The product was dissolved in methanol (1 ml) and treated with a 1M solution hydrochloric acid (36 uL, 0.036 mmol) in diethyl ether and evaporated in vacuo to yield the title compound (14 mg, 32%); MS (ES+) m/e 366 $(M+H]^+$.

EXAMPLE 42

2-{4-[2-(4-Amino-furazan-3-yl)-imidazo[4,5-c]pyridin-1-yl]-phenoxy}-acetamide trifluoroacetate

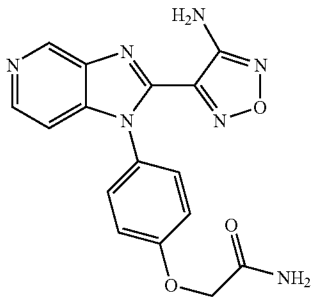

The product of Example 38 (77.0 mg, 0.0260 mmol) was dissolved in N,N-dimethylformamide (1.5 ml) and sodium hydride (60% dispersion in oil, 11.5 mg, 0.286 mmol) was added (gas evolution!). After 5 minutes at room temperature, chloroacetamide (36.5 mg, 0.390 mmol) was added and the solution was heated to 60° C. for 3 hours. The reaction mixture was partitioned between ethyl acetate and satd. aqueous $NaHCO_3$. The aqueous phase was washed with EtOAc (×2), dried over anhydrous sodium sulfate and evaporated in vacuo. Purification of the residue by preparative HPLC (0-80% $CH_3CN/H_2O$ (0.1% TFA), retention time=5.35 minutes) afforded the title compound as a white solid (58 mg, 48%). MS (ES+) m/e 352 $[M+H]^+$.

The following examples were prepared by the general method described in Example 42.

| | Example | Alkyl Halide | Characterisation |
|---|---|---|---|
| 43 | 2-{4-[2-(4-Amino-furazan-3-yl)-imidazo[4,5-c]pyridin-1-yl]-phenoxy}-N,N-dimethylacetamide | N,N-dimethyl chloroacetamide | MS(ES+) m/e 366 [M + H]$^+$ |
| 44 | 2-{4-[2-(4-Amino-furazan-3-yl)-imidazo[4,5-c]pyridin-1-yl]-phenoxy}-ethanol | 2-bromoethanol | MS(ES+) m/e 339 [M + H]$^+$ |
| 45 | 3-{4-[2-(4-Amino-furazan-3-yl)-imidazo[4,5-c]pyridin-1-yl]-phenoxy}-propionitrile | 3-chloropropionitrile | MS(ES+) m/e 429 [M + H]$^+$ |
| 46 | 3-{4-[2-(4-Amino-furazan-3-yl)-imidazo[4,5-c]pyridin-1-yl]-phenoxy}-propan-1-ol | 3-bromopropanol | MS(ES+) m/e 353 [M + H]$^+$ |
| 47 | 2-{4-[2-(4-Amino-furazan-3-yl)-imidazo[4,5-c]pyridin-1-yl]-phenoxy}-N-methyl-acetamide | N-Methyl chloroacetamide | MS(ES+) m/e 366 [M + H]* |
| 48 | 4-[1-(4-Methylsulfanyl-methoxyphenyl)-1H-imidazo[4,5-c]pyridin-2-yl]-furazan-3-ylamine | Chloromethyl methyl sulfide | MS(ES+) m/e 355 [M + H]$^+$ |
| 49 | 4-[1-(4-Phenylsulfanyl-methoxy-phenyl)-1H-imidazo[4,5-c]pyridin-2-yl]-furazan-3-ylamine | Chloromethyl phenyl sulfide | MS(ES+) m/e 433 [M + H]$^+$ |

EXAMPLE 50

(2-{4-[2-(4-Amino-furazan-3-yl)-imidazo[4,5-c]pyridin-1-yl]-phenoxy}-ethyl)-carbamic acid tert-butyl ester trifluoroacetate

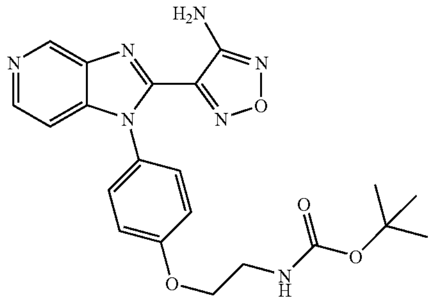

To a suspension of the product of Example 38 (0.400 g, 1.36 mmol) in 1,4-dioxane was added triphenylphosphine (534 mg, 2.04 mmol) and N-BOC ethanolamine (0.316 mL, 2.04 mmol). Diisopropylazodicarboxylate (0.401 mL, 2.04 mmol) was added. After 14.5 hours, the reaction mixture was evaporated in vacuo. The resulting residue was purified by preparative HPLC (0-80% $CH_3CN/H_2O$ (0.1% TFA), retention time=7.75 minutes) affording the title compound as the trifluoroacetate salt (383 mg, 51%). MS (ES+) m/e 438 [M+H]$^+$.

The following example was prepared according to the general procedure described in Example 50:

| | Example | Alcohol | Characterisation |
|---|---|---|---|
| 51 | 4-{1-[4-(2-Methylamino-ethoxy)-phenyl]-1H-imidazo[4,5-c]pyridin-2-yl}-furazan-3-ylamine | N-methyl ethanolamine | MS(ES+) m/e 352 [M + H]$^+$ |

EXAMPLES 52 AND 53

4-[1-(4-Benzenesulfinylmethoxy-phenyl)-1H-imidazo[4,5-c]pyridin-2-yl]-furazan-3-ylamine and 4-[1-(4-Benzenesulfonylmethoxy-phenyl)-1H-imidazo[4,5-c]pyridin-2-yl]-furazan-3-ylamine The product of Example 49 (28.0 mg, 0.053 mmol) was dissolved in methanol (0.600 mL) and $H_2O$ (0.300 mL). Sodium periodate (14 mg, 0.065 mmol) was added and the reaction was allowed to stir for four days. The solution was partitioned between ethyl acetate and aq. NaCl. The organic phase was dried over sodium sulfate, filtered and concentrated. The resulting residue was purified by preparative HPLC (0-80% $CH_3CN/H_2O$ (0.1% TFA) sulfoxide retention time=6.79 minutes; sulfone=7.45 minutes) to yield the title compounds as their trifluoroacetate salts: Example 52 (sulfoxide) (10.0 mg, 35%), MS (ES+) m/e 433 [M+H]$^+$; Example 53 (sulfone) (3.2 mg, 11%), MS (ES+) m/e 449 [M+H]$^+$.

EXAMPLE 54

4-[1-(4-Methanesulfinylmethoxy-phenyl)-1H-imidazo[4,5-c]pyridin-2-yl]-furazan-3-ylamine The title compound was prepared from the product of example 48 according to the procedure described for example 52. MS (ES+) m/e 371 [M+H]$^+$.

EXAMPLE 55

4-{1 [4-(2-Amino-ethoxy)-phenyl]-1H-imidazo[4,5-c]pyridin-2-yl}-furazan-3-ylamine hydrochloride

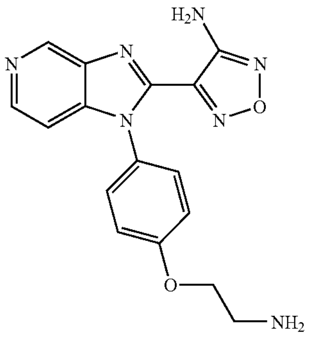

The product of Example 50 was treated with 4.0 M HCl/dioxane. After two hours, the reaction was judged complete by LC-MS. The reaction mixture was concentrated in vacuo to provide the title compound as a white powder (245 mg, 86%). MS (ES+) m/e 339 $[M+H]^+$.

EXAMPLE 56

Isoxazole-5-carboxylic acid (2-{4-[2-(4-amino-furazan-3-yl)-imidazo[4,5-c]pyridin-1-yl]-phenoxy)-ethyl)-amide

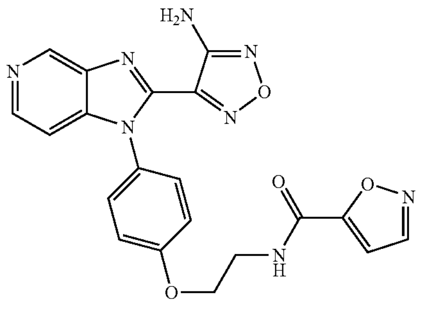

The product of example 55 was suspended in dichloromethane (0.5 mL) and triethylamine (0.025 mL, 0.173 mmol) was added. Isoxaole 5-carbonyl chloride (0.010 mL, 0.073 mmol) was added. After 2.5 hours, the reaction mixture was partitioned between ethyl acetate and 2N NaOH. The aqueous phase was washed with ethyl acetate (×1). The combined organic phases were washed with satd. aq. NaCl, dried over sodium sulfate, filtered and concentrated. The resulting residue was purified by preparative HPLC (0-80% $CH_3CN/H_2O$ (0.1% TFA), retention time=6.42 minutes) to yield the title compound as the trifluoroacetate salt (7.0 mg, 26%). MS (ES+) m/e 433 $[M+H]^+$.

The following example was prepared according to the general procedure described in Example 56:

| | Example | Acid Chloride | Characterisation |
|---|---|---|---|
| 57 | N-(2-{4-[2-(4-Amino-furazan-3-yl)-imidazo[4,5-c]pyridin-1-yl]-phenoxy}-ethyl)-acetamide | Acetyl chloride | MS(ES+) m/e 380 $[M + H]^+$ |

The following example was prepared according to the general procedure described in Example 56, using an additional equivalent of triethylamine:

| | | | |
|---|---|---|---|
| 58 | N-(2-{4-[2-(4-Amino-furazan-3-yl)-imidazo[4,5-c]pyridin-1-yl]-phenoxy}-ethyl)-isonicotinamide | isonicotinoyl chloride hydrochloride | MS(ES+) m/e 433 $[M + H]^+$ |

EXAMPLE 59

(2—[2-(4-Amino-furazan-3-yl)-imidazo[4,5-c]-pyridin-1-yl]-phenoxy}-ethyl)-urea

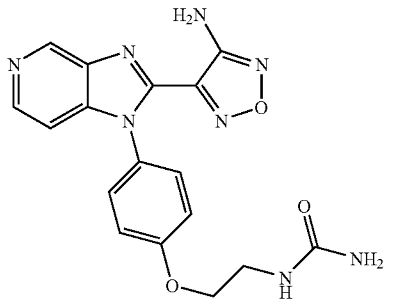

The product of example 55 (25 mg, 0.061 mmol) was dissolved in THF (0.350 mL) and $H_2O$ (0.150 mL). A solution of KOCN (25 mg, 0.0608 mmol) in $H_2O$ (0.150 mL) was added to the reaction slowly dropwise over 30 minutes. After an additional 1.5 hours, the reaction was judged complete by LC-MS analysis. The reaction mixture was partitioned between EtOAc and dilute aq. $NaHCO_3$. The aqueous phase was washed with EtOAc (×1) and the combined organic phases were dried over sodium sulfate, filtered, and concentrated. Trituration with diethyl ether provided a white solid (5.0 mg, 22%). MS (ES+) m/e 381 $[M+H]^+$.

EXAMPLE 60

2-{4-[2-(4-Amino-furazan-3-yl)-imidazo[4,5-c]pyridin-1-yl]-phenoxy}-propionamide

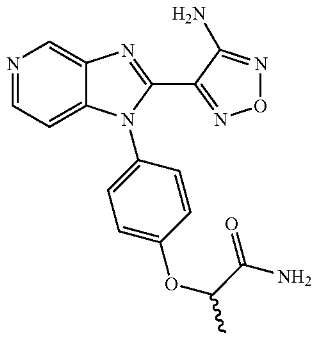

Step 1. 2-{4-[2-(4-Amino-furazan-3-yl)-imidazo[4,5-c]pyridin-1-yl]-phenoxy}-propionic acid methyl ester The ester was prepared from the product of Example 38 (58.0 mg) as described in Example 42, employing methyl 2-bromopropionate as the alkyl halide. The ester was used directly in Step 2. MS (ES+) m/e 381 $[M+H]^+$.

Step 2. 2-{4-[2-(4-Amino-furazan-3-yl)-imidazo[4,5-c]pyridin-1-yl]-phenoxy}-propionamide The product of Step 1 was dissolved in methanol (1.0 mL) and concentrated ammonium hydroxide (0.500 mL) was added. After 14.5 hours, a white precipitate was evident. The reaction mixture was filtered and the solid washed with water and diethyl ether. The title compound was isolated as an off-white powder (12.5 mg, 20%). MS (ES+) m/e 366 $[M+H]^+$.

The following example was prepared according to the procedure described in Example 60, Steps 1 and 2.

| | Example | Alkyl Halide | |
|---|---|---|---|
| 61 | 2-{4-[2-(4-Amino-furazan-3-yl)-imidazo[4,5-c]pyridin-1-yl]-phenoxy}-2-methyl-propionamide | Ethyl 2-bromoisobutyrate | MS(ES+) m/e 366 $[M + H]^+$ |

EXAMPLE 62

N-(2-{4-[2-(4-Amino-furazan-3-yl)-imidazo[4,5-c]pyridin-1-yl]-phenoxy}-ethyl)-methanesulfonamide

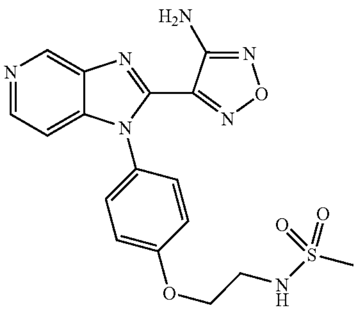

Step 1. 4-{1-[4-(2-Bromo-ethoxy)-phenyl]-1H-imidazo[4,5-c]pyridin-2-yl}-furazan-3-ylamine trifluoroacetate The title compound was prepared using the procedure described in example 50, using 2-bromoethanol as the alcohol. MS (ES+) m/e 381 $[M+H]^+$.

Step 2. N-(2-{4-[2-(4-Amino-furazan-3-yl)-imidazo[4,5-c]pyridin-1-yl]-phenoxy}-ethyl)-methanesulfonamide The product of Step 1 (21.5 mg, 0.042 mmol) and methanesulfonamide (8.0 mg, 0.080 mmol) were dissolved in DMF. Sodium hydride (60% dispersion in mineral oil, 5.3 mg, 0.133 mmol) was added to the reaction, and the mixture was heated to 60° C. After two hours, the reaction was judged complete by LC-MS. The reaction mixture was poured into EtOAc and diluted with pH 7 phosphate buffer.

The layers were separated and the aqueous layer washed with EtOAc (×3). The combined organic layers were dried over sodium sulfate, filtered, and concentrated. The resulting residue was purified by preparative HPLC (0-80% $CH_3CN/H_2O$ (0.1% TFA), retention time=6.29 minutes) to yield the title compound as the trifluoroacetate salt (5.0 mg, 22%). MS (ES+) m/e 416 $[M+H]^+$.

EXAMPLE 63

{4-[2-(4-Amino-furazan-3-yl)-imidazo[4,5-c]pyridin-1-yl]-phenoxy}-acetonitrile

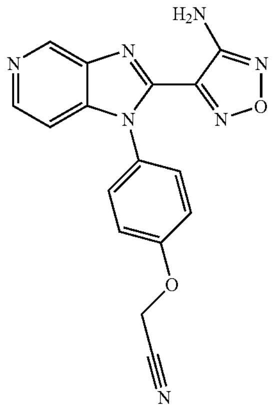

To a solution containing 150 mg of the product from Example 38 (0.51 mmols) in 2.6 mL of dry DMF was added 25 mg of NaH (0.61 mmols, 60% suspension in oil). After stirring at ambient temperature for 5 min, 0.033 mL of chloroacetonitrile (0.51 mmols) was added to the reaction via syringe. The reaction was warmed to 60° C. for 16 h. After cooling to room temperature, 1 mL of water was carefully added to the reaction mixture. The mixture was diluted with 20 mL of EtOAc and washed with 2N NaOH (3×10 mL). The organic layer was dried over $MgSO_4$, filtered, and concentrated in vacuo. The residue was dissolved in a minimum volume of DMSO and filtered through a 0.45 m acrodisc filter. The resulting solution was purified on the Gilson reverse-phase HPLC to afford the title product (4 mg, 2%). MS (ES+) m/e 334 $[M+H]^+$.

The following examples were prepared using the general method of Example 63.

| | Example | alkyl halide or alkyl mesylate | Characterization |
|---|---|---|---|
| 64 | 4-{1-[4-(2-Dimethylamino-1-methyl-ethoxy)-phenyl]-1H-imidazo[4,5-c]pyridin-2-yl}-furazan-3-ylamine | (2-chloro-propyl)-dimethyl-amine | MS $(ES^+)$ m/e 380 $[M + H]^+$ |

-continued

| Example | alkyl halide or alkyl mesylate | Characterization |
|---|---|---|
| 65 4-{1-[4-((S)-1-Methyl-pyrrolidin-2-ylmethoxy)-phenyl]-1H-imidazo[4,5-c]pyridin-2-yl}-furazan-3-yl amine | ((S)-1-Methyl-pyrrolidin-2-yl)-methyl-mesylate | MS ($ES^+$) m/e 392 $[M + H]^+$ |
| 66 4-(1-{4-[2-(Benzyl-methyl-amino)-ethoxy]-phenyl}-1H-imidazo[4,5-c]pyridin-2-yl)-furazan-3-ylamine | N-(2-chloroethyl)-N-methylbenzylamine hydrochloride | MS ($ES^+$) m/e 442 $[M + H]^+$ |

EXAMPLE 67

4-{1-[4-(2-Diethylamino-ethoxy)-phenyl]-1H-imidazo[4,5-c]pyridin-2-yl}-furazan-3-ylamine

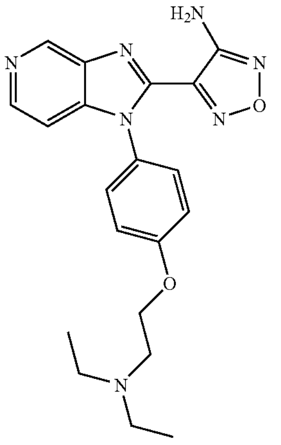

To a solution containing 50 mg the product from Example 38 (0.17 mmols) in 3.4 mL of dry DMF was added 14 mg of NaH (0.34 mmols, 60% suspension in oil). After stirring at ambient temperature for 5 min, 44 mg of 2-bromoethyl-diethylamine (0.17 mmols) was added to the reaction. The reaction was warmed to 60° C. for 16 h. After cooling to room temperature, 1 mL of water was carefully added to the reaction mixture. The mixture was diluted with 20 mL of EtOAc and washed with 2N NaOH (3×10 mL). The organic layer was dried over $MgSO_4$, filtered, and concentrated in vacuo. The residue was dissolved in a minimum volume of DMSO and filtered through a 0.45 m acrodisc filter. The resulting solution was purified on the Gilson reverse-phase HPLC. The resulting product was dissolved in a minimum amount of MeOH and treated with excess 1 N HCl in diethylether. The resulting precipitate was collected and washed with diethylether to afford the title product (11 mg, 17%). MS (ES+) m/e 393 $[M]^+$.

The following examples were prepared using the same general method for Example 67.

| Example | alkyl halide | Characterization |
|---|---|---|
| 68 4-{1-[4-(3-Dimethyl amino-propoxy)-phenyl]-1H-imidazo[4,5-c]pyridin-2-yl}-furazan-3-ylamine | N-(3-chloropropyl)-dimethylamine | MS ($ES^+$) m/e 380 $[M + H]^+$ |
| 69 4-{1-[4-(3-Diisopropylamino-ethoxy)-phenyl]-1H-imidazo[4,5-c]pyridin-2-yl}-furazan-3-ylamine | N-(2-chloroethyl)-diisopropyl-amine hydrochloride | MS ($ES^+$) m/e 422 $[M + H]^+$ |
| 70 4-{1-[4-(3-Morpholin-4-yl-ethoxy)-phenyl]-1H-imidazo[4,5-c]pyridin-2-yl}-furazan-3-ylamine | N-(2-chloroethyl)-morpholine | MS ($ES^+$) m/e 408 $[M + H]^+$ |
| 71 4-{1-[4-(1-Methyl-piperidin-4-yloxy)-phenyl]-1H-imidazo[4,5-c]pyridin-2-yl}-furazan-3-ylamine | N-methyl-4-chloro-piperidine hydrochloride | MS ($ES^+$) m/e 392 $[M + H]^+$ |
| 72 4-{1-[4-(2-Piperidin-1-yl-ethoxy)-phenyl]-1H-imidazo[4,5-c]pyridin-2-yl}-furazan-3-ylamine | N-(2-chloroethyl)-piperidine hydrochloride | MS ($ES^+$) m/e 406 $[M + H]^+$ |

EXAMPLE 73

4-{1-[4-((S)-1-Pyrrolidin-2-ylmethoxy)-phenyl]-1H-imidazo[4,5-c]pyridin-2-yl}-furazan-3-ylamine

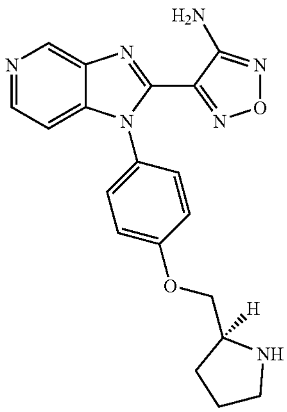

This example was prepared using the same general method of Example 67 using (S)-(−)-1-(tert-butoxycarbonyl)-2-pyrrolidinemethyl-mesylate (48 mg, 23%). MS (ES+) m/e 378 $[M+H]^+$.

The following examples were prepared from the product of Example 38 using the general method of Example 39

| Example | Alkyl halide | Characterization |
|---|---|---|
| 74 4-{1-[3-(2-Dimethyl amino-ethoxy)-phenyl]-1H-imidazo[4,5-c]pyridin-2-yl}-furazan-3-ylamine | N-(2-chloro-ethyl)-dimethyl-amine hydrochloride | MS ($ES^+$) m/e 366 $[M + H]^+$ |

-continued

| | Example | Alkyl halide | Characterization |
|---|---|---|---|
| 75 | 4-{1-[3-(3-Dimethylamino-propoxy)-phenyl]-1H-imidazo[4,5-c]pyridin-2-yl}-furazan-3-ylamine | N-(2-chloro-propyl)-dimethyl-amine hydrochloride | MS ($ES^+$) m/e 380 $[M + H]^+$ |

EXAMPLE 76

4-{1-[4-(3-Methyl-butoxy)-phenyl]-1H-imidazo[4,5-c]pyridin-2-yl}-furazan-3-ylamine

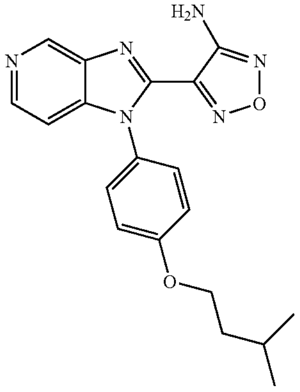

The title compound was prepared using the same general method for Example 50 starting from isoamyl alcohol. MS (ES+) m/e 364 $[M+H]^+$.

EXAMPLE 77

4-{1-[3-(1-Methyl-piperidin-4-yloxy)-phenyl]-1H-imidazo[4,5-c]pyridin-2-yl}-furazan-3-ylamine

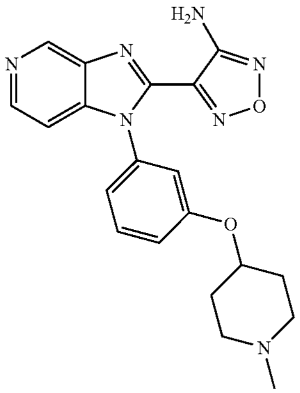

The title compound was prepared from the product of Example 39 using the general method of Example 50 using N-methyl-4-hydroxy-piperidine. MS (ES+) m/e 392 $[M+H]^+$.

EXAMPLE 78

N-{4-[2-(4-Amino-furazan-3-yl)-1H-imidazo[4,5-c]pyridin-2-yl]-phenyl}-N',N'-dimethyl-ethane-1,2-diamine

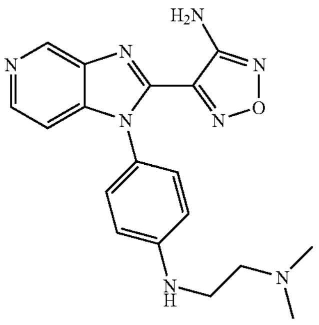

Step 1. 4-[1-(4-Amino-phenyl)-1H-imidazo[4,5-c]pyridin-2-yl]-furazan-3-ylamine

The title compound was prepared by the method of Example 25 starting from 4-chloro-3-nitro pyridine and (4-aminophenyl)-carbamic acid t-butyl ester. MS (ES+) m/e 294 $[M+H]^+$.

Step 2. N-{4-[2-(4-Amino-furazan-3-yl)-1H-imidazo[4,5-c]pyridin-1-yl]-phenyl}-N',N'-dimethyl-ethane-1,2-diamine To a solution containing 500 mg the product from Step 1 (1.7 mmol) in 10 mL DMF was added 200 mg of NaH (60% dispension in oil, 5.1 mmol). After 2 hours at room temperature, 246 mg of 2-(dimethylamino)ethyl chloride hydrochloride (1.7 mmol) was added, and the reaction mixture was heated to 60° C. for 5 hours. The solvent was evaporated in vacuo to yield a residue which was partitioned between ethyl acetate and brine. The organic phase was dried over anhydrous sodium sulphate, filtered, and concentrated in vacuo. Purification of the residue by Gilson reverse-phase HPLC afforded the title compound (24 mg, 4%). MS ($ES^+$) m/e 365 $[M+H]^+$.

EXAMPLE 79

1-{4-[2-(4-Amino-furazan-3-yl)-imidazo[4,5-c]pyridin-1-yl]-phenyl}-3-methyl-urea

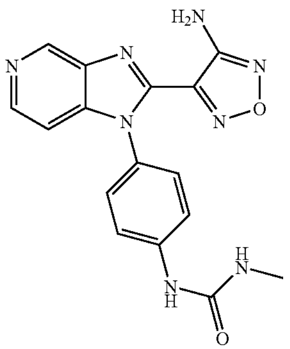

To a solution containing 50 mg the product from Example 78, Step 1 (0.17 mmol) in 1 mL pyridine, was added 20 mg of methyl isocyanate (0.34 mmol) dropwise at 0° C. The resulting mixture was stirred at room temperature for 5 hours. The solvent was evaporated in vacuo to yield a residue which was partitioned between ethyl acetate and brine. The organic phase was dried over anhydrous sodium sulphate, filtered, and concentrated in vacuo. Purification of the residue by Gilson reverse-phase HPLC afforded the title compound (5.4 mg, 9.0%). MS (ES+) m/e 351 [M+H]$^+$.

EXAMPLE 80

N-{4-[2-(4-Amino-furazan-3-yl)-imidazo[4,5-c]pyridin-1-yl]-phenyl}-C-dimethylamino-acetamide

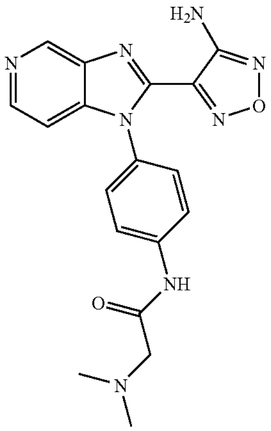

To a solution containing 100 mg of the product of Example 78, Step 1 (0.3 mmol) in 5 mL $CH_2Cl_2$, was added 65 mg of dimethylamino acetyl chloride (0.4 mmol) and 92 mg of triethylamine (0.9 mmol). The resulting mixture was heated to reflux for 12 hours. The reaction was cooled to ambient temperature and the solvent was concentrated in vacuo. The resulting residue was partitioned between ethyl acetate and brine. The organic phase was dried over anhydrous sodium sulphate, filtered, and concentrated in vacuo. Purification of the residue by Gilson reverse-phase HPLC afforded the title compound (38 mg, 30%). MS (ES+) m/e 379 [M+H]$^+$.

The following examples were prepared using the general method of Example 30

-continued

| Example | | Aniline | Characterization |
|---|---|---|---|
| 81 | 4-[1-(1H-Indazol-5-yl)-1H-imidazo[4,5-c]pyridin-2-yl]-furazan-3-ylamine | 5-amino-indazole | MS (ES$^+$) m/e 319 [M + H]$^+$ |
| 82 | 4-[1-(1H-Indazol-6-yl)-1H-imidazo[4,5-c]pyridin-2-yl]-furazan-3-ylamine | 6-amino-indazole | MS (ES$^+$) m/e 319 [M + H]$^+$ |
| 83 | 4-{1-[4-(3-Dimethylamino-propyl)-phenyl]-1H-imidazo[4,5-c]pyridin-2-yl}-furazan-3-ylamine | 4-(3-dimethylamino propyl)aniline (Klein, C. D. P.; Klingmueller, M.; Schellinski, C.; Landmann, S.; Hauschild, S.; Heber, D.; Mohr, K.; Hopfinger, A. J. J. Med. Chem. 1999, 42, 3874-3888. | MS (ES$^+$) m/e 364 [M + H]$^+$ |
| 84 | 4-[1-(4-Dimethylamino-phenyl)-1H-imidazo[4,5-c]pyridin-2-yl]-furazan-3-ylamine | N,N-Dimethyl-benzene-1,4-diamine (Wurster; Chem. Ber. 1879, 12, 523.) | MS (ES$^+$) m/e 322 [M + H]$^+$ |
| 85 | 4-(1-enzo[1,3]dioxol-5-yl-1H-imidazo[4,5-c]pyridin-2-yl) furazan-3-ylamine | benzo [1,3]dioxol-5-ylamine | MS (ES$^+$) m/e 323 [M + H]$^+$ |
| 86 | 4-[1-(2-Methyl-1,2,3,4-tetrahydro-isoquinolin-7-yl)-1H-imidazo[4,5-c]pyridin-2-yl]-furazan-3-ylamine | 2-methyl-1,2,3,4-tetrahydro-isoquinolin-7-ylamine (Heer, J. P.; Harling, John D.; Thompson, Mervyn. Synthetic Communications 2002, 32(16), 2555-2563.) | MS (ES$^+$) m/e 348 [M + H]$^+$ |
| 87 | 1-{4-[2-(4-Amino-furazan-3-yl)-imidazo[4,5-c]pyridin-1-yl]-phenyl}-ethanone oxime | 4-amino-acetophenone | MS (ES$^+$) m/e 336 [M + H]$^+$ |
| 88 | 4-[1-(2,3,4,5-Tetrahydro-1H-benzo[c]azepin-8-yl)-1H-imidazo[4,5-c]pyridin-2-yl]-furazan-3-ylamine | 2,3,4,5-tetrahydro-1 H-benzo[c]azepin-8-ylamine (Grunewald, G. L.; Dahanukar, V. H.; Criscione, K. R. Bioorganic & Medicinal Chemistry 2001, 1957-1965.) | MS (ES$^+$) m/e 348 [M + H]$^+$ |
| 89 | 7-[2-(4-Amino-furazan-3-yl)-imidazo[4,5-c]pyridin-1-yl]-3,4-dihydro-2H-isoquinolin-1-one | 7-amino-3,4-dihydro-2H-isoquinolin-1-one (Lee, N-H.; Lee, C-S.; Jung, D-S. Tetrahedron Lett. 1998, 39, 1385-1388.) | MS (ES$^+$) m/e 348 [M + H]$^+$ |
| 90 | 4-[2-(4-Amino-furazan-3-yl)-imidazo[4,5-c]pyridin-1-yl]-N-hydroxy-benzamidine | 4-amino-benzonitrile | MS (ES+) m/e 337 [M + H]$^+$ |

EXAMPLE 91

N-{4-[2-(4-Amino-furazan-3-yl)-imidazo[4,5-c]pyridin-1-yl]-phenyl}-N,N',N'-trimethyl-ethane-1,2-diamine

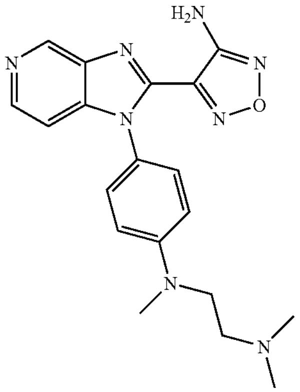

Step 1: N,N, N'-Trimethyl-N'-(4-nitro-phenyl)-ethane-1,2-diamine

To a solution containing 1.52 g of 4-nitro-N-methylaniline (10 mmol) in 30 mL THF, was added 0.8 g of sodium hydride (60% dispension in oil, 20 mmol). After 5 minutes at room temperature, 2.59 g of 2-(dimethylamino)ethyl chloride hydrochloride (18 mmol) and 0.4 g of sodium hydride (60% dispension in oil, 10 mmol) were added. The reaction was heated at 60° C. for 5 hours. The solvent was concentrated in vacuo to yield a residue which was partitioned between ethyl acetate and 2 M sodium hydroxide solution. The organic phase was washed with water (3×), dried over anhydrous sodium sulphate, filtered, and concentrated in vacuo to yield the title compound as a brown oil (1.23 g, 55%). MS ($ES^+$) m/e 224 $[M+H]^+$.

Step 2: N-(2-dimethylaminoethyl)-N-methyl-benzene-1,4-diamine

To a solution containing 1.23 g of product from step 1 (5.5 mmol) in 20 mL MeOH, was added 0.6 g of Pd (5 wt. % on activated carbon). The resulting suspension was stirred under $H_2$ (50 psi) at room temperature for 3 hours. The reaction mixture was filtered through celite. The filtrate was concentrated in vacuo to yield the title compound as a colorless oil (0.71 g, 67%). MS ($ES^+$) m/e 194 $[M+H]^+$.

Step 3: N-{4-[2-(4-Amino-furazan-3-yl)-imidazo[4,5-c]pyridin-1-yl]-phenyl}-N,N',N'-trimethyl-ethane-1,2-diamine This example was prepared using the general method of Example 30 using the product from step 2. MS (ES+) m/e 379 $[M+H]^+$.

EXAMPLE 92

N-{4-[2-(4-Amino-furazan-3-yl)-imidazo[4,5-c]pyridin-1-yl]-phenyl}-N-(2-dimethylamino-ethyl)-N',N'-dimethyl-ethane-1,2-diamine

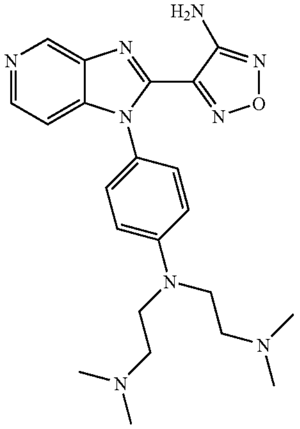

Step 1: N-(2-dimethylamino-ethyl)-N',N'-dimethyl-N-(4-nitro-phenyl)-ethane-1,2-diamine To a solution containing 2.76 g of 4-nitroaniline (20 mmol) in 20 mL DMF was added 1.60 g of NaH (60% dispension in oil, 40 mmol). After 2 hours at room temperature, 2-(dimethylamino)ethyl chloride hydrochloride (3.46 g, 24 mmol) was added, and the reaction mixture was heated at 60° C. for 12 hours. The solvent was evaporated in vacuo to yield a residue which was partitioned between ethyl acetate and brine. The organic phase was dried over anhydrous sodium sulphate, filtered, and concentrated in vacuo to yield a residue. Purification of the residue by flash chromatography with 2% MeOH in $CH_2Cl_2$ as the eluent yielded N,N-dimethyl-N'-(4-nitro-phenyl)-ethane-1,2-diamine (2.34 g, 56%) and the title compound (1.23 g, 22%). MS (ES+) m/e 281 $[M+H]^+$.

Step 2: N,N-bis-(2-dimethylamino-ethyl)-benzene-1,4-diamine

To a solution containing 1.23 g of product from step 1 (4 mmol) in 20 mL MeOH, was added 0.8 g of Pd (5 wt. % on activated carbon, 0.4 mmol). The resulting suspension was stirred under $H_2$ (50 psi) at room temperature for 3 hours. The reaction mixture was filtered, and the filtrate was concentrated in vacuo to yield the title compound as a colorless oil (1.10 g, 100%). MS (ES+) m/e 251 $[M+H]^+$.

Step 3: N-{4-[2-(4-Amino-furazan-3-yl)-imidazo[4,5-c]pyridin-1-yl]-phenyl}-N-(2-dimethylamino-ethyl)-N',N'-dimethyl-ethane-1,2-diamine This example was prepared using the general method of Example 30 using the product from step 2. MS (ES+) m/e 436 $[M+H]^+$.

EXAMPLE 93

N-(2-{4-[2-(4-amino-furazan-3-yl)-imidazo[4,5-c]pyridin-1-yl]-phenoxy}-ethyl)-benzenesulfonamide

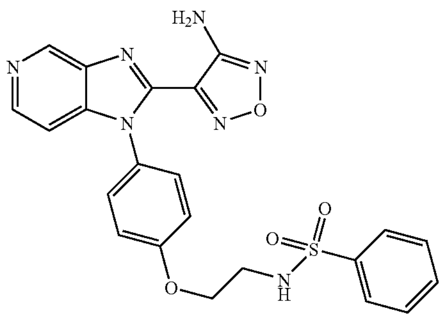

The product of example 55 was suspended in dichloromethane (1.25 mL) and triethylamine (0.218 mL, 0.487 mmol) was added, followed by benzenesulfonyl chloride (0.023 mL, 0.182 mmol). After 30 minutes, the reaction mixture was partitioned between ethyl acetate and 2N NaOH. The aqueous phase was washed with ethyl acetate (×1). The combined organic phases were washed with satd. aq. NaCl, dried over sodium sulfate, filtered and concentrated. The resulting residue was purified by preparative HPLC (0-80% $CH_3CN/H_2O$ (0.1% TFA), retention time=7.31 minutes) to yield the title compound as the trifluoroacetate salt (25.7 mg, 44%). MS (ES+) m/e 478 $[M+H]^+$.

EXAMPLE 94

4-[1-(4-Aminomethyl-phenyl)-1H-imidazo[4,5-c]pyridin-2-yl]-furazan-3-ylamine

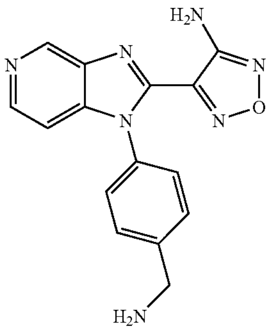

Step 1: {4-[2-(4-Amino-furazan-3-yl)-imidazo[4,5-c]pyridin-1-yl]-benzyl}-carbamic acid tert-butyl ester The title compound was prepared from (4-aminobenzyl)-carbamic acid tert-butyl ester (*J. Am. Chem. Soc,* 112, 12, 2000, 2698-2710), using the procedures detailed in Example 30; MS (ES+), m/e 408 $[M+H]^+$.

Step 2: 4-[1-(4-Aminomethyl-phenyl)-1H-imidazo[4,5-c]pyridin-2-yl]-furazan-3-ylamine The title compound was prepared from the product of Step 1 using the method of Example 21; MS (ES+), m/e 308 $[M+H]^+$.

The following examples were prepared using the general two step method of example 94.

| Example | | Aniline | Characterisation |
|---|---|---|---|
| 95 | 4-[1-(3-Aminomethyl-phenyl)-1H-imidazo[4,5-c]pyridin-2-yl]-furazan-3-ylamine | (3-Amino-benzyl)-carbamic acid tert-butyl ester. (J. Med. Chem. 42, 14, 1999, 2504-2526) | MS (ES+) m/e 308 $[M + H]^+$ |
| 96 | 4-[1-(1,2,3,4-Tetrahydro-isoquinolin-5-yl)-1H-imidazo[4,5-c]pyridin-2-yl]-furazan-3-ylamine | 5-Amino-3,4-dihydro-1H-isoquinoline-2-carboxylic acid tert-butyl ester. (Bioorg. Med. Chem. 8, 8, 2000, 2085-2094). | MS (ES+) m/e 334 $[M + H]^+$ |
| 97 | 4-[1-(1,2,3,4-Tetrahydro-isoquinolin-7-yl)-1H-imidazo[4,5-c]pyridin-2-yl]-furazan-3-ylamine | 7-Amino-3,4-dihydro-1H-isoquinoline-2-carboxylic acid tert-butyl ester (WO 99/14197) | MS (ES+) m/e 334 $[M + H]^+$ |

EXAMPLE 98

4-[1-(2,3-Dihydro-1H-isoindol-5-yl)-1H-imidazo[4,5-c]pyridin-2-yl]-furazan-3-ylamine Step 1: 5-nitroisoindoline Nitrate Isoindoline (4 g, 33.1 mmol) was added to 95%. sulphuric acid, the reaction was treated carefully with fuming nitric acid (2.2 ml) at 0° C. and stirred for 1 hour, then the mixture was poured onto ice and the resulting precipitate was collected by filtration and dried in vacuo to afford the title compound (4.1 g, 46%); 1H NMR (DMSO-d6) 8.35 (1H, s), 8.35 (1H, d, 8.4 Hz), 7.70 (1H, d, 8.4 Hz), 4.64 (4H, s).

Step 2: 5-Nitro-1,3-dihydro-isoindole-2-carboxylic acid tert-butyl ester

The product of Step 1 (3.06 g, 13.47 mmol) in dichloromethane (50 ml) was treated with triethylamine (4.09 g, 40.42 mmol) followed by di-tertbutyl dicarbonate (3.08 g, 14.15 mmol) and stirred at room temperature for 3 days. The reaction was then diluted with dichloromethane and washed with 3N citric acid, sodium bicarbonate solution, water and brine. The organic phase was separated, dried over anhydrous sodium sulfate and evaporated in vacuo to afford the title compound (3.5 g, 98%); 1H NMR (CDCl3) 8.19 (2H, m), 7.26 (1H, m), 4.75 (4H, m), 1.52 (9H, s).

Step 3: 5-Amino-1,3-dihydro-isoindole-2-carboxylic acid tert-butyl ester

The product of Step 2 (3.5 g, 13.25 mmol) was dissolved in ethanol (200 ml) and treated with 10 wt % Palladium on charcoal (1 g), and stirred under 1 atm of $H_2$ for 16 hours. The reaction was filtered and evaporated in vacuo to afford the title compound (3.01 g, 96%); MS (ES+), m/e 235 $[M+H]^+$.

Step 4: 4-[1-(2,3-Dihydro-1H-isoindol-5-yl)-1H-imidazo[4,5-c]pyridin-2-yl]-furazan-3-ylamine The amine from Step 3 was reacted according to the general two step method of Example 94 to give the title product. MS (ES+) m/e 320 $[M+H]^+$.

EXAMPLE 99

4-[1-(3-Pyrrolidin-2-yl-phenyl)-1H-imidazo[4,5-c]pyridin-2-yl]-furazan-3-ylamine

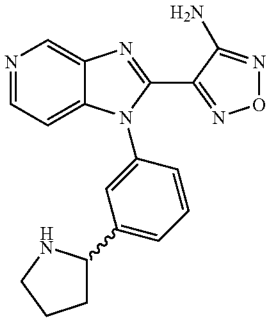

Step 1: 2-(3-Nitro-phenyl)-pyrrole-1-carboxylic acid tert-butyl ester

A solution of 1-bromo-3-nitrobenzene (1.5 g 7.42 mmol) in anhydrous 1,2-dimethoxyethane (10 ml) was treated sequentially with 1,1-bistriphenylphosphine palladium II dichloride (260 mg, 0.371 mmol), 2M aqueous sodium carbonate (7.4 ml), and 1-(t-Butoxycarbonyl)pyrrole-2-boronic acid (1.88 g, 8.91 mmol) dissolved in ethanol (10 ml). The reaction was heated under reflux for 5 hours under argon. The solvent was evaporated and the residue dissolved in dichloromethane, washed with water, brine, dried over anhydrous sodium sulfate, and evaporated in vacuo. The residue was purified by silica gel chromatography eluting with a mixture of ether/hexane (5:95) to afford the title compound (1.09 g, 51%); MS (ES+) m/e 288 $[M+H]^+$.

Step 2: 2-(3-Amino-phenyl)-pyrrolidine-1-carboxylic acid tert-butyl ester

The product of Step 1 (7.5 g, 26.01 mmol), was dissolved in ethanol (125 ml), and treated with 5 wt % Platinum on charcoal (750 mg), and stirred under 1 atm of $H_2$ for 4 days. The reaction was filtered and the filtrate evaporated in vacuo. The residue was purified by silica gel chromatography eluting with a mixture of ether/dichloromethane (5:95) to afford the title compound (4.2 g, 62%); MS (ES+) m/e 263 $[M+H]^+$.

Step 3: 2-{3-[2-(4-Amino-furazan-3-yl)-imidazo[4,5-c]pyridin-1-yl]-phenyl}-pyrrolidine-1-carboxylic acid tert-butyl ester The title compound was prepared from the product of Step 2 using the methods of example 30; MS (ES+), m/e 448 $[M+H]^+$.

Step 4: 4-[1-(3-Pyrrolidin-2-yl-phenyl)-1H-imidazo[4,5-c]pyridin-2-yl]-furazan-3-ylamine The title compound was prepared from the product of Step 3 using the method of Example 21; MS (ES+), m/e 348 $(M+H]^+$.

EXAMPLE 100

4-(7-Bromo-1-ethyl-1H-imidazo[4,5-c]pyridin-2-yl)furazan-3-ylamine

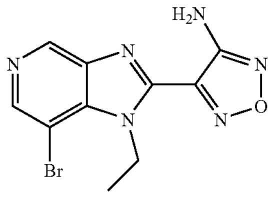

Step 1. (3-Bromo-5-nitropyridin-4-yl)ethylamine

To a solution of the product of Example 1 Step 1 (3.0 g, 17.9 mmol) in acetic acid (40 ml) was added bromine (3.12 g, 1 ml, 19.7 mmol) and the mixture was heated at 100° C. for 20 hours. After cooling the solvent was removed in vacuo and the residue was partitioned between dichloromethane and saturated sodium bicarbonate solution. The organic phase was washed with water (×3), dried and evaporated in vacuo. Purification of the residue by silica gel chromatography eluting with 50% dichloromethane in ethyl acetate afforded the title compound (1.9 g, 43%). $^1H$ NMR (DMSO-$d_6$) 8.73 (1H, s), 8.52 (1H, s), 7.0 (1H, br), 3.25 (2H, m), 1.16 (3H, t, J=7.2 Hz).

Step 2. 5-Bromo-$N^4$-Ethylpyridine-3,4-diamine

A solution of the product of Step 1 (0.5 g, 2 mmol) in ethanol (8 ml)/water (10 ml) was stirred at 60° C. and sodium dithionite (2.12 g, 12.2 mmol) was added protionwise. After 10 minutes the mixture was cooled to room temperature, and diluted with water and dichloromethane. The organic phase was dried and evaporated in vacuo, the residue was used directly in the next reaction; $^1H$ NMR (DMSO-$d_6$) 7.76 (1H, s), 7.75 (1H, s), 5.0 (2H, br), 4.46 (1H, t, J=9.6 Hz), 3.26 (2H, m), 1.06 (3H, t, J=7.2 Hz).

Step 3. 4-(7-Bromo-1-ethyl-1H-imidazo[4,5-c]pyridin-2-yl)furazan-3-ylamine

The title compound was prepared from the product of Step 2 using the methods of Example 1 Steps 3 and 4; MH (ES+) m/e 309/311 $[M+H]^+$.

EXAMPLE 101

4-(1-Ethyl-7-phenyl-1H-imidazo[4,5-c]pyridin-2-yl)furazan-3-ylamine

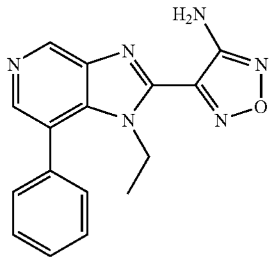

A mixture of the product of Example 100 (50 mg, 0.161 mmol), phenylboronic acid (30 mg, 0.243 mmol), bis(triphenylphosphine)palladium(II) dichloride (11 mg, 0.0161 mmol), sodium carbonate solution (2M, 0.25 ml) and toluene (3 ml) was heated at 100° C. for 3 hours.

After cooling to room temperature the solvent was evaporated in vacuo and the residue purified by silica gel chromatography eluting with 50% dichloromethane in ethyl acetate to afford the title compound; (45 mg, 92%). MS (ES+) m/e 307 $[M+H]^+$.

The following examples were prepared by the general method described in Example 101.

| | Example | Boronic acid | Characterisation |
|---|---|---|---|
| 102 | 4-[1-Ethyl-7-(4-methoxyphenyl)-1H-imidazo[4,5-c]pyridin-2-yl]furazan-3-ylamine | 4-Methoxyphenylboronic acid | MS(ES+) m/e 337 $[M + H]^+$ |
| 103 | 4-(1-Ethyl-7-thiophen-2-yl-1H-imidazo[4,5-c]pyridin-2-yl)furazan-3-ylamine | Thiophene-2-boronic acid | MS (ES+) m/e 313 $[M + H]^+$. |

The following example was prepared by the general method described in Example 101, replacing the toluene solvent by 1,2-dimethoxyethane.

| | | | |
|---|---|---|---|
| 104 | 4-[7-(4-Aminomethylphenyl)-1-ethyl-1H-imidazo[4,5-c]pyridin-2-yl]furazan-3-ylamine | 4-(Aminomethyl)-phenylboronic acid hydrochloride | MS (AP+) m/e 336 $[M + H]^+$. |

The following example was prepared by the general method described in Example 101, replacing the toluene solvent by dioxane.

| | Example | Boronic Acid | Characterization |
|---|---|---|---|
| 105 | 4-[7-(3-Ethoxy-phenyl)-1-ethyl-1H-imidazo[4,5-c]pyridin-2-yl]-furazan-3-ylamine | 3-Ethoxyphenylboronic acid | MS (ES+) m/e 351 $[M + H]^+$ |
| 106 | 4-[1-Ethyl-7-(2-fluoro-phenyl)-1H-imidazo[4,5-c]pyridin-2-yl]-furazan-3-ylamine | 2-Fluorophenylboronic acid | MS (ES+) m/e 325 $[M + H]^+$ |
| 107 | 4-[1-Ethyl-7-(4-methanesulfonyl-phenyl)-1H-imidazo[4,5-c]pyridin-2-yl]-furazan-3-ylamine | 4-(Methanesulfonyl)benzene-boronic acid | MS (ES+) m/e 385 $[M + H]^+$ |
| 108 | 4-[1-Ethyl-7-(4-trifluoromethyl-phenyl)-1H -imidazo[4,5-c]pyridin-2-yl]-furazan-3-ylamine | 4-Trifluoromethylbenzene-boronic acid | MS (ES+) m/e 375 $[M + H]^+$ |
| 109 | 4-[7-(2,4-Difluoro-phenyl)-1-ethyl-1H-imidazo[4,5-c]pyridin-2-yl]-furazan-3-ylamine | 2,4-Difluorophenylboronic acid | MS (ES+) m/e 343 $[M + H]^+$ |
| 110 | 4-[1-Ethyl-7-(2-trifluoromethyl-phenyl)-1H-imidazo[4,5-c]pyridin-2-yl]-furazan-3-ylamine | 2-Trifluoromethylbenzene-boronic acid | MS (ES+) m/e 375 $[M + H]^+$ |
| 111 | 4-[1-Ethyl-7-(4-methylsulfanyl-phenyl)-1H-imidazo[4,5-c]pyridin-2-yl]-furazan-3-ylamine | 4-(Methylthio)benzeneboronic acid | MS (ES+) m/e 353 $[M + H]^+$ |
| 112 | 4-[7-(2,6-Dimethyl-phenyl)-1-ethyl-1H-imidazo[4,5-c]pyridin-2-yl]-furazan-3-ylamine | 2,6-Dimethylphenylboronic acid | MS (ES+) m/e 335 $[M + H]^+$ |
| 113 | 5-[2-(4-Amino-furazan-3-yl)-1-ethyl-1H-imidazo[4,5-c]pyridin-7-yl]-2-fluoro-benzaldehyde | 4-Fluoro-3-formylbenzeneboronic acid | MS (ES+) m/e 353 $[M + H]^+$ |
| 114 | 4-[7-(3-Amino-phenyl)-1-ethyl-1H-imidazo[4,5-c]pyridin-2-yl]-furazan-3-ylamine | 3-Aminobenzeneboronic acid monohydrate | MS (ES+) m/e 322 $[M + H]^+$ |
| 115 | 4-[1-Ethyl-7-(3-trifluoromethoxy-phenyl)-1H-imidazo[4,5-c]pyridin-2-yl]-furazan-3-ylamine | 3-(Trifluoromethoxy)phenyl-boronic acid | MS (ES+) m/e 391 $[M + H]^+$ |
| 116 | 1-{3-[2-(4-Amino-furazan-3-yl)-1-ethyl-1H-imidazo[4,5-c] pyridin-7-yl]-phenyl}-ethanone | 3-Acetylphenylboronic acid | MS (ES+) m/e 349 $[M + H]^+$ |

-continued

| | Example | Boronic Acid | Characterization |
|---|---|---|---|
| 117 | N-}4-[2-(4-Amino-furazan-3-yl)-1-ethyl-1H-imidazo[4,5-c] pyridin-7-yl]-phenyl}-methanesulfonamide | [(4-Methylsulfonyl)amino-phenyl]boronic acid | MS (ES+) m/e 400 $[M + H]^+$ |
| 118 | 4-[(Bis-trifluoromethyl-phenyl)-ethyl-1H-imidazo[4,5-c]pyridin-2-yl]-furazan-3-ylamine | 3,5-Bis(trifluoromethyl)-benzeneboronic acid | MS (ES+) m/e 443 $[M + H]^+$ |
| 119 | 4-[2-(4-Amino-furazan-3-yl)-1-ethyl-1H-imidazo[4,5-c]pyridin-7-yl]-2-fluoro-benzaldehyde | 3-Fluoro-4-formylbenzeneboronic acid | MS (ES+) m/e 353 $[M + H]^+$ |

EXAMPLE 120

4-[1-Ethyl-7-(4-methanesulfinyl-phenyl)-1H-imidazo[4,5-c]pyridin-2-yl]-furazan-3-ylamine

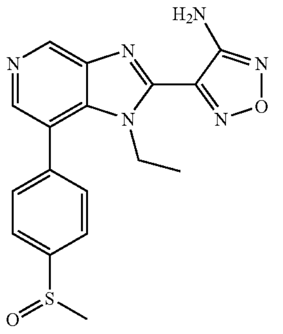

A solution of the product from Example 111 (0.030 g, 0.085 mmol) in dichloromethane (4 mL), was cooled to −78° C. under Argon, and was treated with mCPBA (0.029 g, 0.17 mmol). Allowed the reaction mixture to warm to room temperature and stir for 6 hours. The reaction was reduced in-vacuo, then was dissolved in DMSO (1 mL), and purified on the Gilson via reverse-phase HPLC to afford the title compound (12 mg, 38%); MS (ES+) m/e 369 $[M+H]^+$.

The following example was prepared by the general method described in Example 101, replacing the toluene solvent by DMF.

| | Example | Boronic Acid | Characterization |
|---|---|---|---|
| 121 | 5-[2-(4-Amino-furazan-3-yl)-1-ethyl-1H-imidazo[4,5-c]pyridin-7-yl]-thiophen-2-yl}-carbaldehyde | 5-Formyl-2-thiopheneboronic acid | MS (ES+) m/e 355 $[M + H]^+$ |
| 122 | 4-(7-Benzo[b]thiophen-3-yl-1-ethyl-1H-imidazo[4,5-c]pyridin-2-yl]-furazan-3-ylamine | Benzothiophene-3-boronic acid | MS (ES+) m/e 363 $[M + H]^+$ |
| 123 | 4-[1-Ethyl-7-(4-methyl-thiophen-2-yl)-1H-imidazo[4,5-c]pyridin-2-yl]-furazan-3-ylamine | 4-Methylthiophene-2-boronic acid | MS (ES+) m/e 327 $[M + H]^+$ |
| 124 | 4-[1-Ethyl-7-(5-phenyl-thiophen-2-yl)-1H-imidazo[4,5-c]pyridin-2-yl]-furazan-3-ylamine | 5-Phenylthiophene-2-boronic acid | MS (ES+) m/e 389 $[M + H]^+$ |

The following examples were prepared by the general method described in Example 101, replacing the toluene solvent by 1,2-dimethoxyethane, and palladium bis(triphenylphosphine)palladium(II) dichloride catalyst with tetrakis(triphenylphosphine)palladium(0).

| | | | |
|---|---|---|---|
| 125 | 4-(7-Benzo[1,3]dioxol-5-yl-1-ethyl-1H-imidazo[4,5-c]pyridin-2-yl)furazan-3-ylamine | 3,4-Methylenedioxy phenyl boronic acid | MS (ES+) m/e 351 $[M + H]^+$. |

-continued

| | | | |
|---|---|---|---|
| 126 | 4-(1-Ethyl-7-pyridin-4-yl-1H-imidazo[4,5-c]pyridin-2-yl)furazan-3-ylamine | 4-Pyridylboronic acid | MS (ES+) m/e 308 $[M + H]^+$. |
| 127 | 4-(1-Ethyl-7-pyridin-3-yl-1H-imidazo[4,5-c]pyridin-2-yl)furazan-3-ylamine | 3-Pyridylboronic acid | MS (ES+) m/e 308 $[M + H]^+$. |
| 128 | 4-(1-Ethyl-7-furan-3-yl-1H-imidazo[4,5-c]pyridin-2-yl)furazan-3-ylamine | 3-Furylboronic acid | MS (ES+) m/e297 $[M + H]^+$. |
| 129 | 4-(1-Ethyl-7-thiophen-3-yl-1H-imidazo[4,5-c]pyridin-2-yl)furazan-3-ylamine | 3-Thiopheneboronic acid | MS (ES+) m/e 313 $[M + H]^+$. |
| 130 | 4-[1-Ethyl-7-(4-phenoxy-phenyl)-1H-imidazo[4,5-c]pyridin-2-yl]furazan-3-ylamine | 4-Phenoxybenzene-boronic acid | MS (ES+) m/e 399 $[M + H]^+$. |
| 131 | 4-(1-Ethyl-7-quinoline-8-yl-1H-imidazo[4,5-c]pyridin-2-yl]furazan-3-ylamine | 8-Quinoline boronic acid | MS (ES+) m/e 358 $[M + H]^+$. |
| 132 | 4-[7-(3,5-Dimethyl-isoxazole-4-yl)-1-ethyl-1H-imidazo[4,5-c]pyridin-2-yl]furazan-3-ylamine | 4-(3,5-Dimethylisoxazole) boronic acid | MS (ES+) m/e 326 $[M + H]^+$. |
| 133 | 4-[1-Ethyl-7-(4-fluoro-phenyl)-1H-imidazo[4,5-c]pyridin-2-yl]furazan-3-ylamine | 4-Fluorobenzene boronic | MS (ES+) m/e 346 $[M + H]^+$. |
| 134 | 4-[1-Ethyl-7-(4-indol-5-yl-)-1 H-imidazo[4,5-c]pyridin-2-yl]furazan-3-ylamine | 5-Indolylboronic acid acid | MS (ES+) m/e 325 $[M + H]^+$. |
| 135 | 3-[2-(4-Amino-furazan-3-yl)-1-ethyl-1-H-imidazo[4,5,c]pyridin-7-yl]-benzonitrile | 3-Cyanophenyl boronic acid | MS (ES+) m/e 332 $[M + H]^+$. |
| 136 | 4-[2-(4-Amino-furazan-3-yl)-1-ethyl-1-H-imidazo[4,5,c]pyridin-7-yl]-phenol | 4-Hydroxyphenyl boronic acid | MS (ES+) m/e 323 $[M + H]^+$. |
| 137 | N-{3-[2-(4-Amino-furazan-3-yl)-1-ethyl-1-H-imidazo[4,5,c]pyridin-7-yl]-phenyl}-acetamide | 3-Acetamidophenyl boronic acid | MS (ES+) m/e 364 $[M + H]^+$. |
| 138 | 4-[2-(4-Amino-furazan-3-yl)-1-ethyl-1-H-imidazo[4,5,c]pyridin-7-yl]-benzonitrile | 4-Cyanophenyl boronic acid | MS (ES+) m/e 332 $[M + H]^+$. |
| 139 | 4-[1-Ethyl-7-(3-trifluoromethyl-phenyl)-1H-imidazo[4,5-c]pyridin-2-yl)furazan-3-ylamine | 3-Trifluoromethylphenyl boronic acid | MS (ES+) m/e 375 $[M + H]^+$. |
| 140 | {3-[2-(4-Amino-furazan-3-yl)-1-ethyl-1-H-imidazo[4,5,c]pyridin-7-yl]-phenyl}-methanol | (3-Hydroxymethyl) phenyl boronic acid | MS (ES+) m/e 337 $[M + H]^+$. |
| 141 | 3-[2-(4-Amino-furazan-3-yl)-1-ethyl-1-H-imidazo[4,5,c]pyridin-7-yl]-N,N-dimethyl-benzamide | N,N-Dimethylbenzamide-3-boronic acid | MS (ES+) m/e 378 $[M + H]^+$. |
| 142 | 4-{1-Ethyl-7-[4-(5-methyl-[1,2,4]Oxadiazole-3-yl)-phenyl]-1H-imidazo[4,5-c]pyridin-2-yl]furazan-3-ylamine | 4-(5-Methyl-[1,2,4]Oxadiazol-3-yl)benzene boronic acid [prepared from the corresponding bromide (WO9743262) using the general procedure of Bagley et al Tetrahedron Lett. 2000, 41(35), 6901.] | MS (ES+) m/e 389 $[M + H]^+$. |
| 143 | 4-[2-(4-Amino-furazan-3-yl)-1-ethyl-1-H-imidazo[4,5,c]pyridin-7-yl]-benzamide | 4-Aminocarbonylphenyl boronic acid | MS (ES+) m/e 350 $[M + H]^+$. |
| 144 | 3-[2-(4-Amino-furazan-3-yl)-1-ethyl-1-H-imidazo[4,5,c]pyridin-7-yl]-benzamide | 3-Aminocarbonylphenyl boronic acid | MS (ES+) m/e 350 $[M + H]^+$. |
| 145 | 4-{7-[4-(2-Amino-ethyl)-phenyl]-1-ethyl-1H-imidazo[4,5-c]pyridin-2-yl]furazan-3-ylamine | 4-(2-Amino-ethyl)-benzene boronic acid (WO9910022) | MS (ES+) m/e 350 $[M + H]^+$. |

-continued

| | | | |
|---|---|---|---|
| 146 | 4-[7-(3-aminomethyl-phenyl)-1-ethyl-1H-imidazo[4,5-c]pryridin-2-yl]-furazan-3-ylamine | 3-Aminomethyl-phenyl boronic acid | MS (ES+) m/e 336 [M + H]$^+$ |
| 147 | 4-(1-ethyl-7-o-tolyl-1H-imidazo[4,5]pryidin-2-yl-furazan-3-ylamine | 2-Methylphenyl boronic acid | MS (ES+) m/e 322 [M + H]$^+$ |

The following example was prepared by the general method described in Example 101, replacing the toluene solvent by N,N-dimethylformamide and replacing bis(triphenylphosphine)palladium(II) dichloride with 1,1'-bis(diphenylphoshino)ferrocenedichloropalladium(II) chloroform complex.

| | | | |
|---|---|---|---|
| 148 | 4-[2-(4-Amino-furazan-3-yl)-1-ethyl-1H-imidazo[4,5-c]pryidin-7-yl]-benzaldehyde | 4-Formyl phenyl boronic acid | MS (ES+) m/e 335 [M + H]$^+$ |

EXAMPLE 149

4-[1-Ethyl-7-(4-morpholin-4-ylmethyl-phenyl)-1H-imidazo[4,5-c]pyridin-2-yl]-furazan-3-ylamine

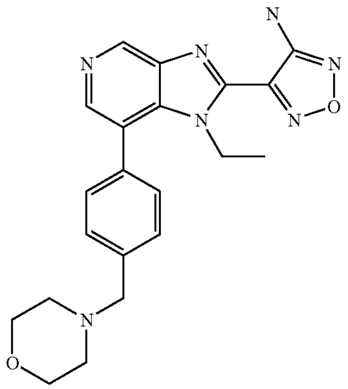

To a solution of the product of Example 148 (65 mg, 0.19 mmol) in methanol (5 ml) was added morpholine (33 mg, 0.033 ml, 0.38 mmol), acetic acid (0.2 ml) and (polystyrylmethyl)trimethylammonium cyanoborohydride (94 mg, 0.38 mmol). This mixture was stirred for 18 hours. The (polystyrylmethyl)trimethylammonium cyanoborohydride was filtered off and the residue concentrated in vacuo. The residue was purified by silica gel chromatography eluting with DCM:methanol (40:1) to afford the title compound (21 mg, 13%); MS (ES+) m/e 406 [M+H]$^+$.

The following compounds were prepared by the general method described in Example 149 from the product of Example 148.

| | Example | Amine | Characterisation |
|---|---|---|---|
| 150 | 4-[1 Ethyl-7-(4-ethylaminomethyl-phenyl)-1H-imidazo[4,5-c]pyridin-2-yl]furazan-3-ylamine | Ethylamine in THF (1M) | MS (ES+) m/e 364 [M + H]$^+$ |
| 151 | 4-{4-[2-(4-Amino-furazan-3-yl)-1-ethyl-1H-imidazo[4,5-c]pyridin-7-yl]-benzylamino}-piperidine-1-carboxylic acid tert-butyl ester | 4-Amino-piperidine-1-carboxylic acid tert-butyl ester | MS (ES+) m/e 519 [M + H]$^+$ |
| 152 | 4-[1-Ethyl-7-(4-pyrrolidin-1-ylmethyl-phenyl)-1H-imidazo[4,5-c]pyridin-2-yl]-furazan-3-ylamine | Pyrrolidine | MS (ES+) m/e 390 [M + H]$^+$ |

EXAMPLE 153

4-[1 Ethyl-7-(3-ethylaminomethyl-phenyl)-1H-imidazo[4,5-c]pyridin-2-yl]furazan-3-ylamine

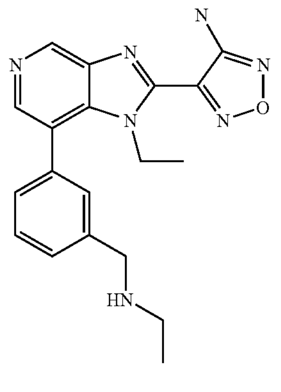

Step 1: 3-[2-(4-Amino-furazan-3-yl)-1-ethyl-1H-imidazo[4,5-c]pryidin-7-yl]-benzaldehyde The crude title compound was prepared from the 3-formylphenyl boronic acid using the method of Example 148.

Step 2: 4-[1 Ethyl-7-(3-ethylaminomethyl-phenyl)-1H-imidazo[4,5-c]pyridin-2-yl]furazan-3-ylamine The product of Step 1 was converted into the title compound by reaction with ethylamine (1M in THF) according to the general method of Example 149. MS (ES+) m/e 364 [M+H]$^+$.

The following compounds were prepared by the general method described in Example 149 from the product of Example 153 Step 1.

| | Example | Amine used | Characterisation |
|---|---|---|---|
| 154 | 4-[7-(3-Dimethylaminomethyl-phenyl)-1-ethyl-1H-imidazo[4,5-c]pyridin-2-yl]-furazan-3-ylamine | Dimethylamine | MS(ES+) m/e 365 $[M + H]^+$ |
| 155 | 4-[1-ethyl-7-(3-morpholin-4-ylmethyl-phenyl)-1 H-imidazo[4,5-c]pyridin-2-yl]-furazan-3-ylamine | Morpholine | MS (ES+) m/e 406 $[M + H]^+$ |
| 156 | 4-[1-Ethyl-7-(3-pyrrolidin-1-ylmethyl-phenyl)-1H-imidazo[4,5-c]pyridin-2-yl]-furazan-3-ylamine | Pyrrolidine | MS (ES+) m/e 390 $[M + H]^+$ |

EXAMPLE 157

{4-[2-(4-Amino-furazan-3-yl)-1-ethyl-1H-imidazo[4,5-c]pyridin-7-yl]-benzyl}-piperidin-4-yl-amine

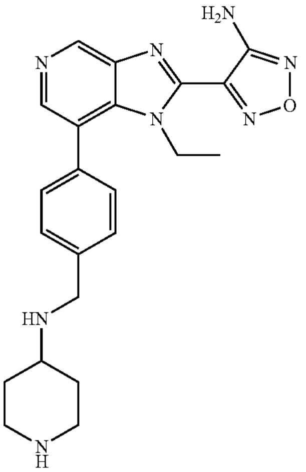

The title compound was prepared from the product of Example 151 using the method described in Example 21; MS (ES+) m/e 419 $[M+H]^+$.

EXAMPLE 158

{3-[2-(4-Amino-furazan-3-yl)-1-ethyl-1H-imidazo[4,5-c]pyridin-7-yl]-benzyl}-piperidin-4-yl-amine

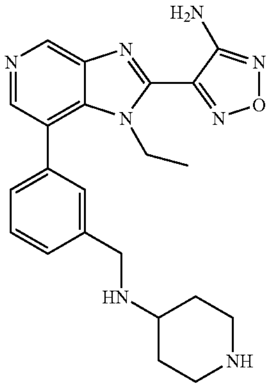

The title compound was prepared from 4-amino-piperidine-1-carboxylic acid tert-butyl ester and the product of Example 153 Step 1 using the method of Example 149, followed by the method described in Example 21. MS (ES+) m/e 419 $[M+H]^+$.

EXAMPLE 159

4-[2-(4-Amino-furazan-3-yl)-1-ethyl-1H-imidazo[4,5-c]pyridin-7-yl]-benzoic Acid

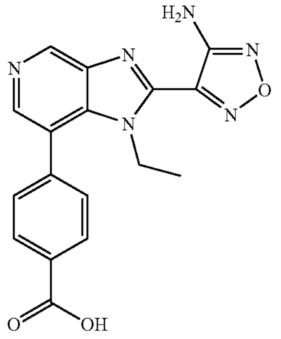

To a solution of the product from Example 100 (1.5 g, 4.85 mmol) in 1,4-Dioxane (50 ml) was added 4-carboxybenzene boronic acid (1.20 g, 7.23 mmol), sodium carbonate (7 ml of a 2 M solution) and tetrakis(triphenylphosphine) palladium(0) (1.12 g, 0.97 mmol). The reaction mixture was heated to reflux with stirring for 18 hours and allowed to cool. The reaction mixture was filetered and washed with ether (5×, 100 ml) to afford the title compound as a yellow solid (0.594 g, 35%); MS (ES+) m/e 351 $[M+H]^+$.

The following example was prepared by the method of Example 159

| | Example | Boronic acid | Characterisation |
|---|---|---|---|
| 160 | 3-[2-(4-Amino-furazan-3-yl)-1-ethyl-1H-imidazo[4,5-c]pyridin-7-yl]-benzoic acid | 3-carboxybenzene boronic acid | MS (ES+) m/e 351 $[M + H]^+$. |

EXAMPLE 161

4-[2-(4-Amino-furazan-3-yl)-1-ethyl-1H-imidazo[4,5-]pyridin-7-yl]-phenyl}-1-morpholin-4-yl-methanone

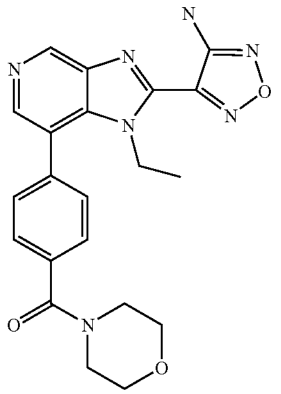

The product from Example 159 in DMF (5 ml) (0.200 g, 571 mmol) was treated with PyBop (892 mg, 1.71 mmol), DIPEA (297 ul, 1.71 mmol) and morpholine (149 ul, 1.71 mmol). The mixture was stirred at room temperature for 18 hours and the crude product concentrated to a glassy solid.

The crude product was purified on a Gilson HPLC system to yield the titled compound as a solid (0.129 g, 54%); MS (ES+) m/e 420 $[M+H]^+$.

The following compounds were prepared by the general method described in Example 161 from the product of Example 159.

| | Example | Amine | Characterisation |
|---|---|---|---|
| 162 | 4-[2-(4-Amino-furazan-3-yl)-1-ethyl-1H-imidazo[4,5-c]pyridin-7-yl]-N-phenethyl-benzamide | phenethyl amine | MS (ES+) m/e 454 $[M + H]^+$ |
| 163 | 4-[2-(4-Amino-furazan-3-yl)-1-ethyl-1H-imidazo[4,5-]pyridin-7-yl]-phenyl}-1-pyrrolidin-1-yl-methanone | Pyrroliidine | MS (ES+) m/e 404 $[M + H]^+$ |
| 164 | 4-[2-(4-Amino-furazan-3-yl)-1-ethyl-1H-imidazo[4,5-c]pyridin-7-yl]-N-benzyl-benzamide | benzylamine | MS (ES+) m/e 440 $[M + H]^+$ |
| 165 | 4-[2-(4-Amino-furazan-3-yl)-1-ethyl-1H-imidazo[4,5-c]pyridin-7-yl]-phenyl}-methanoyl)-pyrrolidine-2-carboxylic acid methyl ester | L-proline methyl estser | MS (ES+) m/e 462 $[M + H]^+$ |
| 166 | 4-[2-(4-Amino-furazan-3-yl)-1-ethyl-1H-imidazo[4,5-c]pyridin-7-yl]-phenyl}-1-(4-methyl-piperazin-1-yl)-methanone | 1-methyl piperazine | MS (ES+) m/e 433 $[M + H]^+$ |

The following compounds were prepared by the general method described in Example 161 from the product of Example 160.

| | Example | Amine | Characterisation |
|---|---|---|---|
| 167 | 3-[2-(4-Amino-furazan-3-yl)-1-ethyl-1H-imidazo[4,5-c]pyridin-7-yl]-N-phenethyl-benzamide | phenethyl amine | MS (ES+) m/e 454 $[M + H]^+$ |
| 168 | 3-[2-(4-Amino-furazan-3-yl)-1-ethyl-1H-imidazo[4,5-c]pyridin-7-yl]-N-benzyl-benzamide | benzylamine | MS (ES+) m/e 440 $[M + H]^+$ |
| 169 | 3-[2-(4-Amino-furazan-3-yl)-1-ethyl-1H-imidazo[4,5-c]pyridin-7-yl]-phenyl}-methanoyl)-pyrrolidine-2-carboxylic acid methyl ester | L-proline methyl estser | MS (ES+) m/e 462 $[M + H]^+$ |
| 170 | 3-[2-(4-Amino-furazan-3-yl)-1-ethyl-1H-imidazo[4,5-c]pyridin-7-yl]-phenyl}-1-(4-methyl-piperazin-1-yl)-methanone | 1-methyl piperazine | MS (ES+) m/e 433 $[M + H]^+$ |

-continued

| | Example | Amine | Characterisation |
|---|---|---|---|
| 171 | 3-[2-(4-Amino-furazan-3-yl)-1-ethyl-1H-imidazo[4,5-]pyridin-7-yl]-phenyl}-1-morpholin-4-yl-methanone | morpholine | MS (ES+) m/e 420 $[M + H]^+$ |

EXAMPLE 172

[2-(4-Amino-furazan-3-yl)-1-ethyl-1H-imidazo[4,5-c]pyridin-7-yl]-phenyl-amine

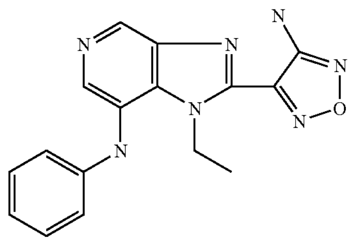

Under Ar, a solution of the product from Example 100 (24 mg, 77.6 mol) in 1,4-dioxane (0.8 ml) and toluene (1.2 ml) was treated with Tris(dibenzylidene-acetone)dipalladium (7.2 mg, 7.8 mol), racemic-2,2'-Bis(diphenylphosphino)-1,1'-binaphthyl (9.7 mg, 15.6 mol), aniline (8.5 l, 93.1 mol), and sodium tert-butoxide (10.5 mg, 108.6 mol). This mixture was then heated to 175° C. by microwave for 45 min. After cooled to ambient temperture, the reaction mixture was diluted with ethyl acetate (30 ml), filtered though a celite pad and then the filtrate was concentrated in vacuo. The residue was purified with reverse phase HPLC (10% $MeCN/H_2O \rightarrow 80\%$ $MeCN/H_2O$), to afford the title compound, (6.3 mg, 24%); MS (ES+) m/e 322 $[M+H]^+$.

The following examples were obtained by the method of Example 172.

| | Example | Aniline | Characterisation |
|---|---|---|---|
| 173 | [2-(4-Amino-furazan-3-yl)-1-ethyl-1H-imidazo[4,5-c]pyridin-7-yl]-pyridin-3-yl-amine | 3-aminopyridine | MS(ES+) m/e 323 $[M + H]^+$ |
| 174 | [2-(4-Amino-furazan-3-yl)-1-ethyl-1H-imidazo[4,5-c]pyridin-7-yl]-(4-morpholin-4-yl-phenyl)-amine | 4-morpholinoaniline | MS (ES+) m/e 407 [M + H]+ |

EXAMPLE 175

4-[1-Ethyl-7-(4-methoxy-phenylsulfanyl)-1H-imidazo[4,5-c]pyridin-2-yl]-furazan-3-ylamine

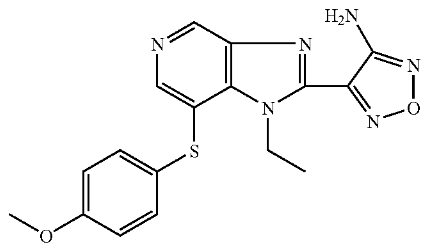

Under Ar, a solution of the product from Example 100 (53.2 mg, 172 mol) in 1,4-dioxane (1 ml) and toluene (1.5 ml) was treated with Tris(dibenzylidene-acetone)dipalladium (15 mg, 17 mol), racemic-2,2'-Bis(diphenylphosphino)-1,1'-binaphthyl (20 mg, 34 mol), 4-methoxybenzenethiol (26 l, 206 mol), and sodium tert-butoxide (23.5 mg, 241 mol). This mixture was then heated to 175° C. by microwave for 1 h. After cooled to ambient temperture, the reaction mixture was diluted with ethyl acetate (30 ml) and methanol (30 ml), filtered though a celite pad and then the filtrate was concentrated in vacuo. The residue was purified with flash chromatography (hexanes/ethyl acetate 2:1), to afford the title compound, (35.6 mg, 56%); MS (ES+) m/e 369 $[M+H]^+$.

The following example was obtained by the method of Example 175.

| | Example | thiophenol | Characterization |
|---|---|---|---|
| 176 | 4-[1-Ethyl-7-phenyl-sulfanyl)-1H-imidazo[4,5-c]pyridin-2-yl]-furazan-3-ylamine | benzenethiol | MS(ES+) m/e 339 $[M + H]^+$ |

EXAMPLE 177

4-(1-cyclopropyl-7-phenyl-1H-imidazo[4,5c]pyridin-2-yl)furazan-3-ylamine

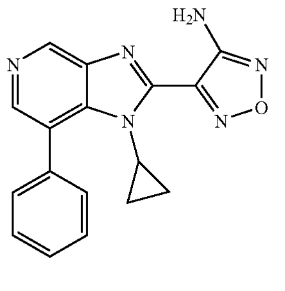

Step 1. 3-Bromo-5-nitropyridin-4-ol

To a suspension of 4-hydroxy-3-nitropyridine (7.00 g, 50 mmol) in water (50 ml) was added bromine (3.23 ml, 63 mmol) dropwise at room temperature. The resulting mixture was stirred for one hour then heated to 50° C. for two hours. After cooling to room temperature and stirring for a further hour the product was filtered off, washed with water and dried under vacuum for two days, affording 9.54 g (87%); MS (AP−) m/e 217/219 $[M+H]^+$.

Step 2. 3-Bromo-4-chloro-5-nitro-pyridine

To phosphorous oxychloride (50 ml) cooled in ice was slowly added the product of step 1 (6.57 g, 30 mmol). To the resulting stirred solution was added N,N-diethylaniline (4.77 ml, 30 mmol) dropwise. The resulting mixture was warmed to room temperature, then heated to reflux for two hours. After this time the mixture was concentrated under vacuum and the residue poured onto ice. The mixture was extracted into diethyl ether and the organic phase washed twice with water, followed by once with brine before concentrating to a brown oil which solidified on standing, 8.01 g (>100%); $^1H$ NMR ($CDCl_3$) 8.94 (1H, s), 8.93 (1H, s).

Step 3. (3-Bromo-5-nitro-pyridin-4-yl)-cyclopropyl-amine

To a solution of the product of Step 2 (8.01 g, ca. 30 mmol) in dichloromethane (100 ml) at 0° C. was added cyclopropylamine (4.16 ml, 60 mmol) drop-wise. The resulting mixture was stirred overnight at room temperature, then concentrated under vacuum to a residue and re-dissolved in ethyl acetate, basifying with sodium bicarbonate. The organic phase was washed with water three times, followed by twice with brine before concentrating under vacuum to a crude solid. This oil was purified by column chromatography eluting with a gradient of 50% DCM/hexane to DCM affording product as a yellow solid, 6.22 g (80%); MS (ES+) m/e 258/260 $[M+H]^+$.

Step 4. 5-Bromo-$N^4$-cyclopropyl-pyridine-3,4-diamine

To a stirred solution of the product obtained from Step 3 (2.95 g, 11.4 mmol) in glacial acetic acid (50 ml) was added iron dust (3.35 g, 60 mmol). The resulting mixture was stirred at 80° C. for 90 minutes, after which it was filtered through Celite and the liquor concentrated under vacuum. The crude product was re-dissolved in ethyl acetate, basified with sodium bicarbonate and refiltered. Th organic phase was washed with water three times, followed by twice with brine before concentrating under vacuum to give the product. Passed through a silica plug affording product as an oil, 1.65 g (63%); MS (ES+) m/e 228/230 $[M+H]^+$.

Step 5. 4-(7-Bromo-1-cyclopropyl-1H-imidazo[4,5-c]pyridin-2-yl)-furazan-3-ylamine The title compound was prepared from the product of Step 4 using the method of Example 1 Steps 3 and 4; MS (ES+) m/e 321/323 $[M+H]^+$.

Step 6. 4-(1-Cyclopropyl-7-phenyl-1H-imidazo[4,5-c]pyridin-2-yl)furazan-3-ylamine The title compound was prepared from the product of Step 5 and phenylboronic acid using the method of Example 101; MS (ES+) m/e 319 $[M+H]^+$.

The following compounds were prepared from the product of Example 177, Step 5 and the corresponding boronic acid using the general method of Example 101

| | | | |
|---|---|---|---|
| 178 | 4-[7-(4-Aminomethylphenyl)-1-cyclopropyl-1H-imidazo[4,5-c]pyridin-2-yl]furazan-3-ylamine | 4-(Aminomethyl)-phenylboronic acid hydrochloride | MS (ES+) m/e 348 $[M + H]^+$. |

-continued

| | | | |
|---|---|---|---|
| 179 | 4-(1-Cyclopropyl-7-thiophen-2-yl-1H-imidazo[4,5-c]pyridin-2-yl)furazan-3-ylamine | 2-Thiopheneboronic acid | MS (ES+) m/e 325 [M + H]+. |

EXAMPLE 180

4-(7-Bromo-1-phenyl-1H-imidazo[4,5-c]pyridin-2-yl)-furazan-3-ylamine

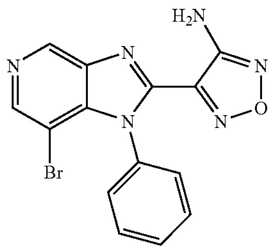

The title compound was prepared from the product of Example 177 Step 2 and aniline using the method described in Example 177 Steps 3-5; MS (ES+) m/e 358 $[M+H]^+$.

EXAMPLE 181

4-(1-Phenyl-7-thiophen-2-yl-1H-imidazo[4,5-c]pyridin-2-yl)-furazan-3-ylamine

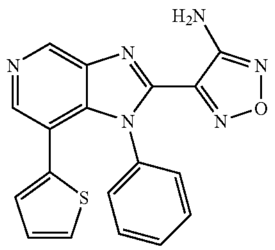

A stirred mixture of the product from Example 180 (50 mg, 0.14 mmol), thiophene-2-boronic acid (27 mg, 0.21 mmol) and $Pd(dppf)_2Cl_2.CH_2Cl_2$ (11 mg, 0.014 mmol) in 3.5 ml of 2.5:1 Dioxane/2 M $K_2CO_3$ contained in a 20 ml pressure tube was heated to 110° C. for 18 h. The resulting biphase mixture was cooled to room temperature. The organic layer (top) was removed with pipet, filtered to remove the Pd. The aqueous layer was extracted once with EtOAc. EtOAc was combined with the organic filtrate, washed with sat'd $NaHCO_3$, water, brine, dried ($Na_2SO_4$) and reduced in vacuo. the residue was purified by silica gel chromatography eluting with 10% MeOH in $CHCl_3$, to afford the title compound, (9 mg, 18%); MS (ES+) m/e 361 $[M+H]^+$.

The following examples were prepared from the product of Example 180 using the method described in Example 181.

| | Example | Boronic acid | Characterisation |
|---|---|---|---|
| 182 | 4-(1,7-Diphenyl-1H-imidazo[4,5-c]pyridin-2-yl)-furazan-3-ylamine | phenylboronic acid | MS(ES+) m/e 355 M + H]+ |
| 183 | 4-[2-(4-Amino-furazan-3-yl)-1-phenyl-1H-imidazo [4,5-c]pyridin-7-yl]-phenol | 4-hydroxybenzene boronic acid | MS (ES+) m/e 371 [M + H]+ |
| 184 | 4-[7-(3,5-Dimethyl isoxazole-4-yl)-1-phenyl-1H-imidazo[4,5-c]pyridin-2-yl]-furazan-3-ylamine | 3,5-dimethyl isoxazole-4-boronic acid | MS (ES+) m/e 374 [M + H]+ |

EXAMPLE 185

4-[7-(4-Ethylaminomethyl-phenyl)-1-phenyl-1H-imidazo[4,5-c]pyridin-2-yl]-furazan-3-ylamine

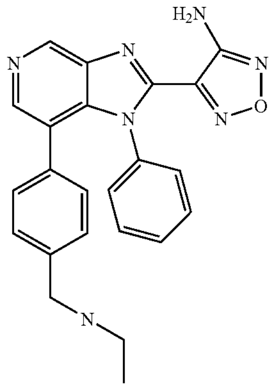

Step 1. 4-[2-(4-Amino-furazan-3-yl)-1-phenyl-1H-imidazo[4,5-c]pyridin-7-yl]-benzaldehyde A stirred mixture the product of Example 180 (0.2 g, 0.56 mmol), 4-formylbenzeneboronic acid (0.126 g, 0.84 mmol) and $Pd(dppf)_2Cl_2.CH_2C)_2$ (0.046 g, 0.056 mmol) in 6.0 ml of 2.5:1 Dioxane/2 M $K_2CO_3$ contained in a 20 ml pressure tube was heated to 110° C. for 18 h. The resulting biphase mixture was cooled to room temperature. The organic layer (top) was removed with pipet, filtered to remove the Pd. The aqueous layer was extracted once with EtOAc. EtOAc was combined with the organic filtrate, washed with sat'd $NaHCO_3$, water, brine, dried ($Na_2SO_4$) and reduced in vacuo. the residue was purified by silica gel chromatography eluting with 10% MeOH in $CHCl_3$, to afford the title compound, (0.10 g, 47%); MS (ES+) m/e 383 $[M+H]^+$.

Step 2. 4-[7-(4-Ethylaminomethyl-phenyl)-1-phenyl-1H-imidazo[4,5-c]pyridin-2-yl]-furazan-3-ylamine To a stirring solution of the product from step 1 (0.1 g, 0.26 mmol) and ethylamine (in THF, 0.12 ml, 0.24 mmol) in methylene chloride (4 ml) was added sodium triacetoxy-borohydride (0.055 g, 0.26 mmol) and acetic acid (0.4 ml). The reaction mixture was stirred overnight The solvent was removed and the residue was washed with sat'd $NaHCO_3$, extracted 3× with EtOAc water, dried ($Na_2SO_4$) and reduced in vacuo. The residue was purified by silica gel chromatography eluting with 30% ethyl acetate in hexane, to afford the title compound, (0.016 g, 15%); MS (ES+) m/e 411 $[M+H]^+$.

EXAMPLE 186

2-(4-Amino-furazan-3-yl)-1-phenyl-1H-imidazo[4,5-c]pyridine-7-carboxylic acid

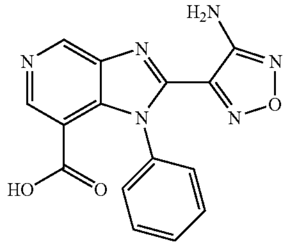

A solution of the-product from Example 180 (0.1 g, 0.28 mmol) in tetrahydrofuran (10 ml) at −78° C. was treated with 2 M solution lithium diisopropylamide (LDA, 0.28 ml, 0.56 mmol) in hexane under argon. After 5 minutes the solution was treated with a 1.6 M solution of n-butyl lithium (0.52 ml, 0.84 mmol) in hexane at −78° C. The mixture was stirred for 10 mins, then carbon dioxide gas was bubbled through the solution for 10 mins. The resulting pale yellow suspension was allowed to warm to room temperature over 2 h, water (1 ml) in tetrahydrofuran (3 ml) was cautiously added dropwise and the mixture concentrated in vacuo. The residual solid was washed with ether (2×10 ml) then dissolved in methanol (10 ml) containing glacial acetic acid. The solvent was evaporated and the residue triturated under ether (2 ml) and filtered to give the title compound (10 mg, 11%); MS (ES+) m/e 323 $[M+H]^+$.

EXAMPLE 187

4-[7-Bromo-1-(4-methoxy-phenyl)-1H-imidazo[4,5-c]pyridin-2-yl]-furazan-3-ylamine

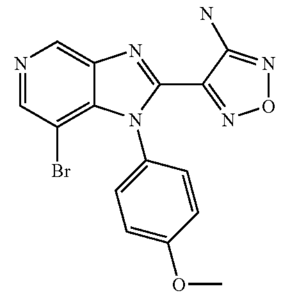

The title compound was prepared from the product of Example 177 Step 2 and 4-methoxy-aniline using the method described in Example 177 Steps 3-5; MS (ES+) m/e 388 $[M+H]^+$.

EXAMPLE 188

4-[2-(4-Amino-furazan-3-yl)-7-bromo-imidazo[4,5-c]pyridin-1-yl]-phenol

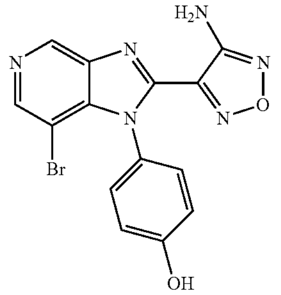

To a solution of the product from Example 187 (0.1 g, 0.26 mmol) in anhydrous dichloromethane (10 ml) stirred at 0° C., was added dropwise boron tribromide (1.0 M solution in dichloromethane, 2.3 ml, 2.3 mmol) and the mixture stirred at room temperature for 16 hours. The reaction was quenched with water (20 ml), basified to pH 14 with 50% sodium hydroxide solution. The aqueous phase was washed with dichloromethane 3×, neutralised with 6 N hydrochloric acid, and the resulting precipitate collected, washed with water 3×, diethyl ether and dried in vacuo to yield the title product (40 mg, 40%); MS (ES+) m/e 374 $[M+H]^+$.

EXAMPLE 189

4-{1-[4-(2-Dimethylamino-ethoxy)-phenyl]-7-phenyl-1H-Imidazo[4,5-c]pyridin-2-yl}-furazan-3-ylamine

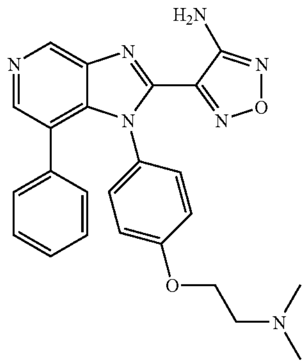

Step 1. 4-{7-Bromo-1-[4-(2-dimethylamino-ethoxy)-phenyl]-1H-imidazo[4,5-c]pyridin-2-yl}-furazan-3-ylamine The title compound was obtained from the product of Exaample 188 by the method of Example 41; MS (ES+) m/e 444/446 $[M+H]^+$.

Step 2. 4-(1-[4-(2-Dimethylamino-ethoxy)-phenyl]-7-phenyl-1H-imidazo[4,5-c]pyridin-2-yl-furazan-3-ylamine A stirred mixture of the product of Step 1 (0.1 g, 0.23 mmol), phenylboronic acid (41 mg, 0.34 mmol) and $Pd(dppf)_2Cl_2.CH_2Cl_2$ (19 mg, 0.023 mmol) in 2.5 ml of 2.5:1 Dioxane/2 M $K_2CO_3$ contained in a 20 ml pressure tube was heated to 110° C. for 18 h. The resulting biphase mixture was cooled to room temperature. The organic layer (top) was removed with pipet, filtered to remove the Pd. The aqueous layer was extracted once with EtOAc. EtOAc was combined with the organic filtrate, washed with sat'd $NaHCO_3$, water, brine, dried ($Na_2SO_4$) and reduced in vacuo. the residue was purified by silica gel chromatography eluting with 10% MeOH in $CHCl_3$, to afford the title compound, (16 mg, 16%); MS (ES+) m/e 442 $[M+H]^+$.

The following examples were prepared from the product of Exaple 189, Step 1 using the method of Example 189, Step 2.

| | Example | Boronic acid | Characterisation |
|---|---|---|---|
| 190 | 4-[1-[4-(2-Dimethylamino-ethoxy)-phenyl]-7-(4-fluoro-phenyl)-1H-imidazo[4,5-c]pyridin-2-yl]-furazan-3-ylamine | 4-fluorophenyl boronic acid | MS(ES+) m/e 460 $[M + H]^+$ |

EXAMPLE 191

[2-(4-Amino-furazan-3-yl)-1-ethyl-1H-imidazo[4,5-c]pyridin-7-ylmethyl]-piperidin-4-yl-amine

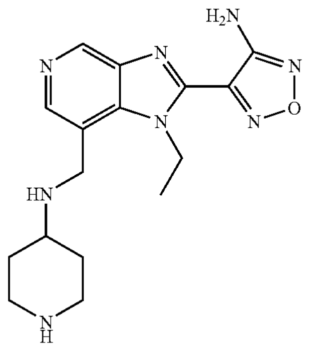

Step 1. 2-(4-Amino-furazan-3-yl)-1-ethyl-1H-imidazo[4,5-c]pyridine-7-carbaldehyde A solution of the product from Example 100 (0.1 g, 0.324 mmol) in tetrahydrofuran (4 ml) at −78° C. was treated with a 1.6M solution of n-butyllithium (0.6 ml, 0.97 mmol) in hexanes. After 5 minutes the mixture was treated with dimethylformamide (0.3 ml) and allowed to reach room temperature. After 30 minutes at room temperature the reaction was carefully quenched with water and extracted into dichloromethane (×2). The organic layer was then washed with brine, dried ($Na_2SO_4$) and reduced in vacuo. The residue was purified by silica gel chromatography eluting with ethyl acetate, to afford the title compound, (0.034 g, 41%); MS (ES+) m/e 259 $[M+H]^+$.

Step 2. 4-{[2-(4-Amino-furazan-3-yl)-1-ethyl-1H-imidazo[4,5-c]pyridin-7-ylmethyl]-amino}-piperidine-1-carboxylic acid tert-butyl ester The title compound was prepared from the product of Step 1 and 4-Amino-piperidine-1-carboxylic acid tert-butyl ester according to the general method of Example 149; MS (ES+) m/e 443 $[M+H]^+$.

Step 3. [2-(4-Amino-furazan-3-yl)-1-ethyl-1H-imidazo[4,5-c]pyridin-7-ylmethyl]-piperidin-4-yl-amine A solution of the product from Step 2 (0.075 g, 0.17 mmol) in dichoromethane (1 ml) was treated with trifluoroacetic acid (1 ml). After 2 hours the reaction was reduced in vacuo, dissolved in methanol and applied to a SCX ion exchange column and eluted with methanol and then a mixture of methanol/0.880 ammonia (9:1). The basic fractions were then reduced to afford the title compound, (0.053 g, 91%); MS (ES+) m/e 343 $[M+H]^+$.

The following examples were prepared from the product of Example 191 Step 1 using the method described in Example 149 followed by the method of Example 191 Step 3

| | Example | Amine | Characterisation |
|---|---|---|---|
| 192 | 1-[2-(4-Amino-furazan-3-yl)-1-ethyl-1H-imidazo[4,5-c]pyridin-7-ylmethyl]-piperidin-4-ylamine | Piperidin-4-yl-carbamic acid tert-butyl ester | MS(ES+) m/e 343 $[M + H]^+$ |
| 193 | 4-(1-Ethyl-7-piperazin-1-ylmethyl-1H-imidazo[4,5-c]pyridin-2-yl)-furazan-3-ylamine | piperazine-1-carboxylic acid tert-butyl ester | MS (ES+) m/e 329 $[M + H]^+$ |

EXAMPLE 194

N-[2-(4-Amino-furazan-3-yl)-1-ethyl-1H-imidazo[4,5-c]pyridin-7-ylmethyl]-N-piperidin-4-yl-acetamide

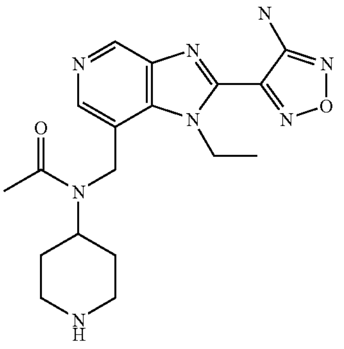

Step 1. 4-{Acetyl-[2-(4-amino-furazan-3-yl)-1-ethyl-1H-imidazo[4,5-c]pyridin-7-ylmethyl]-amino}-piperidine-1-carboxylic acid tert-butyl ester The title compound from Example 191, Step 2 (145 mg, 0.3 mmol) in dichloromenthane at 0° C. was treated with potassium carbonate (90 mg, 0.66 mmol) followed by acetyl chloride (26 mg, 0.33 mL), and the mixture was stirred at room temperature for 1 hour. Purification of the residue by silica gel chromatography eluting with 10% methanol/dichloromethane afforded the title compound (68 mg, 10%). MS (ES+) m/e 484 $[M+H]^+$.

Step 2. N-[2-(4-Amino-furazan-3-yl)-1-ethyl-1H-imidazo[4,5-c]pyridin-7-ylmethyl]-N-piperidin-4-yl-acetamide The title compound was prepared from the product of Step 1 and 4-Amino-piperidine-1-carboxylic acid tert-butyl ester according to the general method of Example 191 Step 3. MS (ES+) m/e 384 $[M+H]^+$.

The following examples were prepared from the product of Example 191 Step 1 using the method described in Example 149.

| | Example | Amine | Characterisation |
|---|---|---|---|
| 195 | 4-{7-[(4-Bromo-benzylamino)-methyl]-1-ethyl-1H-imidazo[4,5-c]pyridin-2-yl}-furazan-3-ylamine | 4-Bromo-benzylamine | MS(ES+) m/e 429 $[M + H]^+$ |
| 196 | 4-{1-Ethyl-7-[(3-methoxy-benzylamino)-methyl]-1H-imidazo[4,5-c]pyridin-2-yl}-furazan-3-ylamine | 3-Methoxy-benzylamine | MS (ES+) m/e 380 $[M + H]^+$ |
| 197 | 4-(1-Ethyl-7-morpholin-4-ylmethyl-1H-imidazo[4,5-c]pyridin-2-yl)furazan-3-ylamine | Morpholine | MS(ES+) m/e 330 $[M + H]^+$ |
| 198 | 4-(1-Ethyl-7-piperidin-1-ylmethyl-1H-imidazo[4,5-c]pyridin-2-yl)furazan-3-ylamine | Piperidine | $^1$H NMR($D^6$DMSO) δ 9.06 (1H, s), 8.27(1H, s), 6.96 (2H, br s), 5.00(2H, q, J8, 13Hz), 3.77(2H, s), 2.50–2.25(4H, m), 1.56–1.30(9H, m) |
| 199 | 4-[1-Ethyl-7-(4-ethylpiperazin-1-ylmethyl)-1H-imidazo[4,5-c]pyridin-2-yl)furazan-3-ylamine | 1-Ethylpiperazine | MS(ES+) m/e 357 $[M + H]^+$ |

EXAMPLE 200

4-{-Ethyl-7-[4-(4-fluoro-phenyl)-piperazin-1-ylmethyl]-1H-imidazo[4,5-c]pyridin-2-yl)furazan-3-ylamine

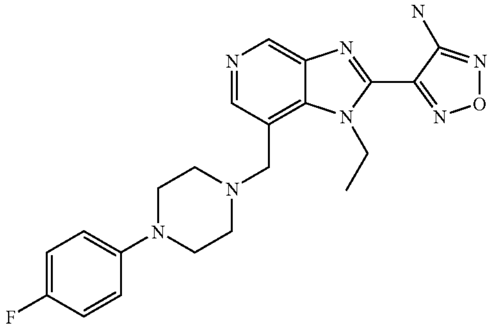

The product of Example 191 Step 1 (0.10 g, 0.38 mmole) in 1,2-dichloroethane (5 ml) was treated with 1-(4-fluorophenyl)piperazine (0.10 g, 0.58 mmole) and stirred at ambient temperature for 15 minutes. Sodium triacetoxyborohydride (0.16 g, 0.76 mmole) was added and the reaction mixture stirred at ambient temperature for 18 hours. The mixture was diluted with dichloromethane, washed (×2) with saturated sodium hydrogen carbonate solution followed by saturated brine, dried over magnesium sulphate and concentrated in vacuo. The residue was purified by column chromatography on silica gel eluting with ethyl acetate to afford the title compound; MS (ES+) m/e 357 $[M+H]^+$. The following examples were prepared from the product of Example 191 Step 1 using the method described in Example 200.

| | Example | Amine | Characterisation |
|---|---|---|---|
| 201 | 4-{1-Ethyl-7-[(3-pyrrolidin-1-yl-propylamino)-methyl]-1H-imidazo[4,5-c]pyridin-2-yl}-furazan-3-ylamine | 1-(3-aminopropyl)pyrrolidine | MS(ES+) m/e 371 $[M + H]^+$ |
| 202 | [2-(4-Amino-furazan-3-yl)-1-ethyl-1H-midazo[4,5-c]pyridin-7-ylmethyl]-methyl-(1-methyl-piperidin-4-yl)-amine | 1-Methyl-4-(methylamino)-piperidine | MS(ES+) m/e 371 $[M + H]^+$ |
| 203 | 4-[1-Ethyl-7-((S)-2-pyrrolidin-1-ylmethyl-pyrrolidin-1-ylmethyl)-1H-imidazo[4,5-c]pyridin-2-yl]- furazan-3-ylamine | (S)-(+)-1-(2-pyrrolidinyl-methyl)pyrrolidine | MS(ES+) m/e 397 $[M + H]^+$ |
| 204 | 2-{4-[2-(4-Amino-furazan-3-yl)-1-ethyl-1H-imidazo[4,5-c]pyridin-7-ylmethyl]-piperazin-1-yl}-1-pyrrolidin-1-yl-ethanone | 1-(Pyrrolidinocarbonyl-methyl)piperazine | MS(ES+) m/e 440 $[M + H]^+$ |

-continued

| | Example | Amine | Characterisation |
|---|---|---|---|
| 205 | 4-{1-Ethyl-7-[(2-pyrrolidin-1-yl-ethylamino)-methyl]-1H--imidazo[4,5-c]pyridin-2-yl}-furazan-3-ylamine | 1-(2-Aminoethyl)-pyrrolidine | MS(ES+) m/e 357 $[M + H]^+$ |
| 206 | 4-[1-Ethyl-7-(4-methyl-piperazin-1-ylmethyl)-1H-imidazo[4,5-c] pyridin-2-yl]-furazan-3-ylamine | N-Methyl-piperazine | MS(ES+) m/e 343 $[M + H]^+$ |
| 207 | 4-[1-Ethyl-7-((R)-2-pyrrolidin-1-ylmethyl-pyrrolidin-1-ylmethyl)-1H-imidazo[4,5-c] pyridin-2-yl]- furazan-3-ylamine | (S)-(+)-1-(2-pyrrolidinylmethyl)pyrrolidine (de Costa et al, J. Med. Chem., 1992; 35; 23, 4334-4343) | MS(ES+) m/e 397 $[M + H]^+$ |
| 208 | 4-[7-((S)-3-Dimethylamino-pyrrolidin-1-ylmethyl)-1-ethyl-1H-imidazo[4,5-c]pyridin-2-yl]-furazan-3-ylamine | Dimethyl-(S)-pyrrolidin-3-yl-amine (Cesare, P. et al, J. Med. Chem., 1992; 35; 22, 4205-4213) | MS(ES+) m/e 357 $[M + H]^+$ |
| 209 | [2-(4-Amino-furazan-3-yl)-1-ethyl-1H-imidazo[4,5-c]pyridin-7-ylmethyl]-(1-methyl-piperidin-4-yl)-amine | 1-Methyl-piperidin-4-ylamine (Brookes et al, J. Chem. Soc., 1957; 3165-3171) | MS(ES+) m/e 357 $[M + H]^+$ |
| 210 | 4-[1-Ethyl-7-((S)-2-morpholin-4-ylmethyl-pyrrolidin-1-ylmethyl)-1H-imidazo[4,5-c] pyridin-2-yl]-furazan-3-ylamine | 4-(S)-1-Pyrrolidin-2-ylmethyl-morpholine (Asami, M. et al, Bull. Chem. Soc. Jpn, 1990; 63, 3, 721-727) | MS(ES+) m/e 413 $[M + H]^+$ |
| 211 | 4-{1-Ethyl-7-[(3-piperidin-1-yl-propylamino)-methyl]-1H-imidazo[4,5-c] pyridin-2-yl}-furazan-3-ylamine | 3-Piperidin-1-yl-propylamine (Lehman, Chem. Ber., 1894; 27, 2176) | MS(ES+) m/e 385 $[M + H]^+$ |
| 212 | 4-{1-Ethyl-7-[(3-morpholin-4-yl-propylamino)-methyl]-1H-imidazo[4,5-c] pyridin-2-yl}-furazan-3-ylamine | 3-Morpholin-4-yl-propylamine (Utermohlen et al, J. Amer. Chem. Soc., 1941; 63, 156-158) | MS(ES+) m/e 387 $[M + H]^+$ |
| 213 | 4-(1-Ethyl-7-{[3-(4-methyl-piperazin-1-yl)-propylamino]-methyl}-1H-imidazo[4,5-c] pyridin-2-yl)-furazan-3-ylamine | 3-(4-Methyl-piperazin-1-yl)-propylamine (Short, J. H., et al, J. Med. Chem., 1963; 6, 275-283) | MS(ES+) m/e 400 $[M + H]^+$ |
| 214 | 4-[1-Ethyl-7-((S)-2-piperidin-1-ylmethyl-pyrrolidin-1-ylmethyl)-1H-imidazo[4,5-c] pyridin-2-yl]-furazan-3-ylamine | 1-(S)-1-Pyrrolidin-2-ylmethyl-piperidine (Asami, M., Bull. Chem. Soc. Jpn., 1990, 63(3), 721-7) | MS(ES+) m/e 411 $[M + H]^+$ |
| 215 | 4-[7-((3R,5S)-3,5-Dimethylpiperazin-1-ylmethyl)-1-ethyl-1H-imidazo[4,5-c]pyridin-2-yl)furazan-3-ylamine | cis-2,6-Dimethylpiperazine | MS(ES+) m/e 357 $[M + H]^+$ |
| 216 | 4-[1-Ethyl-7-(4-pyrrolidin-1-ylpiperidin-1-ylmethyl)-1H-imidazo[4,5-c]pyridin-2-yl)furazan-3-ylamine | 4-(1-Pyrrolidinyl)piperidine | MS(ES+) m/e 397 $[M + H]^+$ |
| 217 | 1-{4-[2-(4-Amino-furazan-3-yl)-1-ethyl-1H-imidazo[4,5-c]pyridin-7-ylmethyl]-piperazin-1-yl}-ethanone | 1-acetylpiperazine | MS(ES+) m/e 371 $[M + H]^+$ |
| 218 | 4-[7-((R)-3-Dimethylamino-pyrrolidin-1-ylmethyl)-1-ethyl-1H-imidazo[4,5-c]pyridin-2-yl]-furazan-3-ylamine | Dimethyl-(R)-pyrrolidin-3-yl-amine | MS(ES+) m/e 357 [M + H]+ |
| 219 | [2-(4-Amino-furazan-3-yl)-1-ethyl-1H-imidazo[4,5-c]pyridin-7-ylmethyl]-(1-isopropyl-piperidin-4-yl)-amine | 1-Isopropyl-4-amino-piperidine | MS(ES+) m/e 385 $[M + H]^+$ |
| 220 | {(S)-1-[2-(4-Amino-furazan-3-yl)-1-ethyl-1H-imidazo[4,5-c]pyridin-7-ylmethyl]-pyrrolidin-2-yl}-methanol | (S)-1-Pyrrolidin-2-yl-methanol | MS(ES+) m/e 344 $[M + H]^+$ |

-continued

| | Example | Amine | Characterisation |
|---|---|---|---|
| 221 | 3-{[2-(4-Amino-furazan-3-yl)-1-ethyl-1H-imidazo[4,5-c]pyridin-7-ylmethyl]-amino}-propan-1-ol | 3-Amino-propan-1-ol | MS(ES+) m/e 318 $[M + H]^+$ |

The following examples were prepared from the product of Example 191 Step 1 using the method described in Example 200 followed by the method described in Example 191 Step 3.

| | Example | Amine | Characterisation |
|---|---|---|---|
| 222 | 4-[1-Ethyl-7-(pyrrolidin-3-ylaminomethyl)-1H-imidazo[4,5-c]pyridin-2-yl]-furazan-3-ylamine | 3-Amino-pyrrolidine-1-carboxylic acid tert-butyl ester (Falgueyret, J. P. et al, J. Med. Chem., 2001; 44, 1, 94-104) | MS(ES+) m/e 329 $[M + H]^+$ |
| 223 | 4-(1-Ethyl-7-{[((S)-1-pyrrolidin-2-ylmethyl)-amino]-methyl}-1H-imidazo[4,5-c]pyridin-2-yl)-furazan-3-ylamine | (S)-2-Aminomethyl-pyrrolidine-1-carboxylic acid tert-butyl ester (Slaitas, A. et al, Nucleosides Nucleotides, 2001; 20, 4-7, 1377-1380) | MS(ES+) m/e 343 $[M + H]^+$ |
| 224 | 4-(7-{[(4-Aminomethyl-cyclohexylmethyl)-amino]-methyl}-1-ethyl-1H-imidazo[4,5-c] pyridin-2-yl)-furazan-3-ylamine | (4-Aminomethyl-cyclohexylmethyl)-carbamic acid tert-butyl ester (Lum, R. T., WO 9532945) | MS(ES+) m/e 385 $[M + H]^+$ |
| 225 | 4-{1-Ethyl-7-[(2-piperazin-1-yl-ethylamino)-methyl]-1H-imidazo[4,5-c] pyridin-2-yl}-furazan-3-ylamine | 4-(2-Amino-ethyl)-piperazine-1-carboxylic acid tert-butyl ester (Krapcho, A. et al, J. Med. Chem., 1998; 41, 27, 5429-5444) | MS(ES+) m/e 372 $[M + H]^+$ |
| 226 | 4-[7-((R)-3-Aminopyrrolidin-1-ylmethyl)-1-ethyl-1H-imidazo[4,5-c]pyridin-2-yl)furazan-3-ylamine | (3R)-(+)-(3-tert-butoxycarbonyl-amino)pyrrolidine | MS(ES+) m/e 329 $[M + H]^+$ |
| 227 | 4-[7-((S)-3-Aminopyrrolidin-1-ylmethyl)-1-ethyl-1H-imidazo[4,5-c]pyridin-2-yl)furazan-3-ylamine | (3S)-(−)-(3-tert-butoxycarbonylamino)pyrrolidine | MS(ES+) m/e 329 $[M + H]^+$ |
| 228 | 4-(1-Ethyl-7-{[(pyrrolidin-2-ylmethyl)amino]methyl}-1H-imidazo[4,5-c]pyridin-2-yl)furazan-3-ylamine | 2-(Aminomethyl)-1-N-tert-butoxycarbonylpyrrolidine | MS(ES+) m/e 343 $[M + H]^+$ |
| 229 | [2-(4-Aminofurazan-3-yl)-1-ethyl-1H-imidazo[4,5-c] ]pyridin-7-ylmethyl]methylpiperidin-4-yl-amine | 1-tert-Butoxycarbonyl-4-methylaminopiperidine | MS(ES+) m/e 357 $[M + H]^+$ |
| 230 | {1-[2-(4-Aminofurazan-3-yl)-1-ethyl-1H-imidazo[4,5-c] pyridin-7-ylmethyl]piperidin-4-yl}methylamine | 4-[N-(tert-butoxycarbonyl)-methylamino]piperidine (Russell et al, J. Med. Chem. 1999; 42; 24, 4981-5001) | MS(ES+) m/e 357 $[M + H]^+$ |
| 231 | 4-(7-[1,4]Diazepan-1-ylmethyl-1-ethyl-1H-imidazo[4,5-c]pyridin-2-yl)-furazan-3-ylamine | tert-butyl 1-homopiperazine carboxylate | MS(ES+) m/e 343 $[M + H]^+$ |
| 232 | 4-(1-Ethyl-7-{[(piperidin-4-ylmethyl)-amino]-methyl}-1H-imidazo[4,5-c]pyridin-2-yl)furazan-3-yl amine | 4-(aminomethyl)-1-boc-piperidine | MS(ES+) m/e 357 $[M + H]^+$ |
| 233 | N-[2-(4-aminofurazan-3-yl)-1-ethyl-1H-imidazo[4,5-c]pyridin-7-methyl]-trans-cyclohexane-1,4-diamine | trans-(4-Amino-cyclohexyl)-carbamic acid tert-butyl ester (Bioorganic & Medicinal Chemistry (2000), 8(6), 1451) | MS(ES+) m/e 357 $[M + H]^+$ |
| 234 | {1-[2-(4-Amino-furazan-3-yl)-1-ethyl-1H-imidazo[4,5-c] pyridin-7-ylmethyl]-piperidin-4-yl}-methyl-amine | N-Methyl-piperidin-4-yl-carbamic acid tert-butyl ester | MS(ES+) m/e 357 $[M + H]^+$ |

-continued

| | Example | Amine | Characterisation |
|---|---|---|---|
| 235 | 4-{1-Ethyl-7-[(2-piperazin-1-yl-ethylamino)-methyl]-1H-imidazo[4,5-c]pyridin-2-yl}-furazan-3-ylamine | 4-(2-Amino-ethyl)-piperazine-1-carboxylic acid tert-butyl ester (Krapcho et al, J. Med. Chem., 1998; 41; 27, 5429-5444) | MS(ES+) m/e 372 $[M+H]^+$ |

EXAMPLE 236

{1-[2-(4-Amino-furazan-3-yl)-1-ethyl-1H-imidazo[4,5-c]pyridin-7-ylmethyl]-piperidin-4-yl}-cyclopropyl-amine

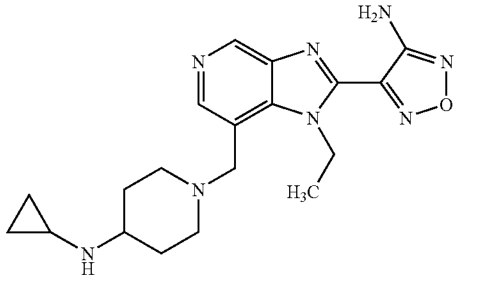

Step 1: 4-[7-(1,4-Dioxa-8-aza-spiro[4.5]dec-8-ylmethyl)-1-ethyl-1H-imidazo[4,5-c]pyridin-2-yl]-furazan-3-ylamine The title compound was prepared from the product of Example 191, Step 1 and 4-piperidone-ethylene-ketal using the method of Example 200. MS (ES+) m/e 386 $[M+H]^+$.

Step 2:1-[2-(4-Amino-furazan-3-yl)-1-ethyl-1H-imidazo[4,5-c]pyridin-7-ylmethyl]-piperidin-4-one The product from Step 1 (0.245 g, 0.64 mmole) in 1,4-dioxane (20 ml) and aqueous hydrochloric acid (5M, 10 ml) was heated under reflux for 18 hours. The mixture was allowed to cool to ambient temperature, neutralised by addition of aqueous sodium hydroxide solution (5M) and extracted into dichloromethane.

The combined organic extracts were dried under magnesium sulfate and concentrated in vacuo. The residue was purified by column chromatography on silica gel eluting with ethyl acetate to afford the title compound (0.054 g); MS (ES+) m/e 341 $[M+H]^+$.

Step 3: {1-[2-(4-Amino-furazan-3-yl)-1-ethyl-1H-imidazo[4,5-c]pyridin-7-ylmethyl]-piperidin-4-yl}-cyclopropyl-amine The title compound was prepared from the product of Step 2 and cyclopropylamine using the method of Example 200. MS (ES+) m/e 383 $[M+H]^+$.

EXAMPLE 237

[2-(4-Amino-furazan-3-yl)-1-ethyl-1-H-imidazo[4,5-c]pyridin-7-ylmethyl]-(8-methyl-8-aza-bicyclo[3.2.1]oct-3-yl)-amine dihydrochloride

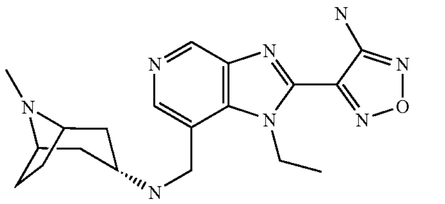

The product of Example 191 Step 1 (150 mg, 0.58 mmole) in 5% acetic acid and dichloromethane (5 ml) was treated with 8-Methyl-8-aza-bicyclo[3.2.1]oct-3-ylamine (179 mg, 1.2 mmole) and stirred at ambient temperature for 20 minutes. Sodium borohydride (13 mg, 0.34 mmol) was added and the reaction mixture stirred at ambient temperature for 20 hours. The product was diluted with dichloromethane, washed water followed by saturated brine, dried over sodium sulphate and concentrated in vacuo. The residue was purified by column chromatography on silica gel eluting with 20% ammonia in methanol/dichloromethane. to afford the title compound as a free base; (34 mg, 15%) MS (ES+) m/e 396 $[M+H]^+$. A solution of the resulting free base (34 mg, 0.08 mmol) in anhydrous methanol (1 ml) was treated with 1M hydrochloric acid in ether and stirred for 30 minutes. The resulting white precipitate was filtered and dried in vacuo to afford the title compound as a colourless hydrochloride salt; (34 mg, 92%) MS (ES+) m/e 396 $[M+H]^+$.

EXAMPLE 238

4-{1-Ethyl-7-[(3-piperazin-1-yl-propylamino)-methyl]-1H-imidazo[4,5-c]pyridin-2-yl}-furazan-3-ylamine

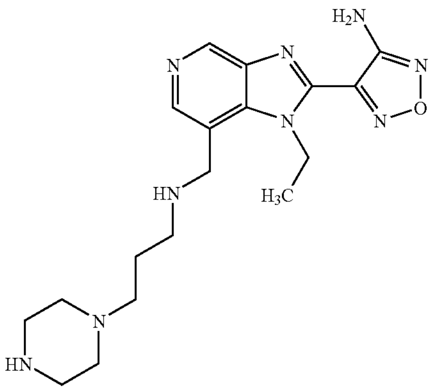

Step 1: (3-Oxo-propyl)-carbamic acid tert-butyl ester

A solution of oxalyl chloride (0.27 ml, 3.15 mmole) in dry dichloromethane (8 ml) was cooled to −78° C. Dimethyl sulfoxide (0.45 ml, 6.29 mmole) in dichloromethane (1 ml) was added dropwise maintaining the reaction temperature at −40° C. The reaction mixture was stirred for 5 minutes and a solution of (3-hydroxy-propyl)-carbamic acid tert-butyl ester (0.50 g, 2.86 mmole) in dichloromethane (3 ml) was added dropwise. After stirring for 15 minutes, triethylamine (1.99 ml, 14.3 mmole) was added and the mixture allowed to warm to ambient temperature. The reaction was quenched by adding water (10 ml), extracted with dichloromethane and the organic extracts were washed with aqueous hydrochloric acid solution (2M), saturated sodium bicarbonate solution and water. The organic layer was dried under magnesium sulfate and the solvent removed in vacuo to afford the title compound (0.45 g). $^1H$ NMR (CDCl3) δ 9.81 (1H, s), 3.45-3.40 (2H, t, J=5 Hz), 2.72-2.69 (2H, t, J=5 Hz), 1.43 (9H, s).

Step 2: 4-(3-tert-Butoxycarbonylamino-propyl)-piperazine-1-carboxylic Acid 9H-fluoren-9-ylmethyl ester Piperazine-1-carboxylic acid 9H-fluoren-9-ylmethyl ester hydrochloride (0.67 g, 1.93 mmole) was dissolved in methanol (5 ml), treated with diisopropylamine (0.34 m], 1.93 mmole) and allowed to stir at room temperature for 5 minutes. The product from Step 1 (0.50 g, 2.89 mmole) and sodium cyanoborohydride (133 mg, 2.12 mmole) were added and the mixture stirred under argon for 18 hours. The solvent was removed in vacuo and the residue was dissolved in dichloromethane, washed with saturated sodium bicarbonate solution, dried over magnesium sulfate and concentrated in vacuo. The residue was purified by column chromatography eluting with ethyl acetate/hexane (1:1) to afford the title compound (0.71 g). $^{1}$H NMR (CDC13) δ 7.78-7.75 (2H, d), 7.59-7.56 (2H, d), 7.41-7.31 (4H, m), 4.52-4.43 (2H, d), 4.27-4.20 (1H, t), 3.51-3.42 (4H, br m), 3.25-3.15 (2H, m), 2.45-2.35 (6H, m), 1.72-1.60 (2H, m), 1.45 (9H, s).

Step 3: 4-(3-Amino-propyl)-piperazine-1-carboxylic Acid 9H-fluoren-9-ylmethyl ester The title compound was obtained from the product of step 2 by the general method of Example 21. $^{1}$H NMR (CDC13) δ 7.78-7.75 (2H, d), 7.60-7.55 (2H, d), 7.40-7.31 (4H, m), 4.48-4.44 (2H, d), 4.26-4.20 (1H, t), 3.50-3.41 (4H, br m), 3.01-2.94 (2H, m), 2.58-2.50 (2H, m), 2.45-2.40 (4H, br m), 1.80-1.75 (2H, m).

Step 4: 4-(3-([2-(4-Amino-furazan-3-yl)-1-ethyl-1H-imidazo[4,5-c]pyridin-7-ylmethyl]-amino}-propyl)-piperazine-1-carboxylic acid 9H-fluoren-9-ylmethyl Ester The title compound was prepared from the product of Example 191 Step 1 and the product from Step 3 using the method of Example 200. MS (ES+) m/e 608 [M+H]$^{+}$.

Step 5: 4-{-Ethyl-7-[(3-piperazin-1 yl-propylamino)-methyl]-1H-imidazo[4,5-c]pyridin-2-yl)-furazan-3-ylamine The product from step 4 (0.17 g, 0.28 mmole) was dissolved in dichloromethane (3 ml) and treated with piperidine (0.3 ml, 2.8 mmole). The mixture was stirred at room temperature under argon for 4 hours. The solvent was removed in vacuo and the residue purified by column chromatography on silica gel eluting with ammonia/methanol/dichloromethane (1:9:90) to afford the title compound (0.063 g). MS (ES+) m/e 386 [M+H]$^{+}$.

EXAMPLE 239

4-[1-Ethyl-7-((R)-2-morpholin-4-ylmethyl-pyrrolidin-1-ylmethyl)-1H-imidazo[4,5-c]pyridin-2-yl]-furazan-3-ylamine

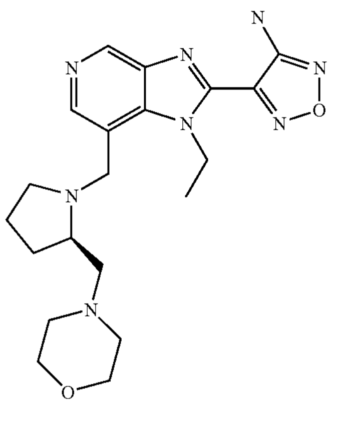

Step 1: (R)-2-Morpholin-4-ylmethyl-pyrrolidine-1-carboxylic acid tert-butyl ester The title compound was prepared from N-(t-butoxycarbonyl)D-prolinal and morpholine according to the general method of Example 200; MS (ES+), m/e 271 [M+H]$^{+}$.

Step 2: 4-(R)-1-Pyrrolidin-2-ylmethyl-morpholine

The title compound was prepared from the product of step 1 accoring to the general method of Example 191 Step 3; MS (ES+), m/e 171 [M+H]$^{+}$.

Step 3: 4-[1-Ethyl-7-((R)-2-morpholin-4-ylmethyl-pyrrolidin-1-ylmethyl)-1H-imidazo[4,5-c]pyridin-2-yl]-furazan-3-ylamine The title compound was prepared from the product of Step 2 and the product of Example 191 Step 1 using the procedures detailed in example 200; MS (ES+), m/e 413 [M+H]$^{+}$.

EXAMPLE 240

4-[1-Ethyl-7-((R)-2-piperidin-1-ylmethyl-pyrrolidin-1-ylmethyl)-1H-imidazo[4,5-c]pyridin-2-yl]-furazan-3-ylamine

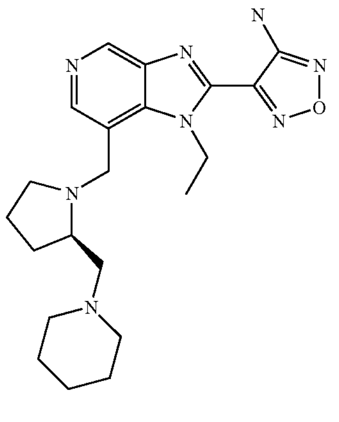

Step 1: (R)-2-Piperidin-1-ylmethyl-pyrrolidine-1-carboxylic acid tert-butyl ester The title compound was prepared from N-(t-butoxycarbonyl)D-prolinal and piperidine using the procedure detailed in example 200; MS (ES+), m/e 269 [M+H]$^{+}$.

Step 2: 1-(R)-1-Pyrrolidin-2-ylmethyl-piperidine

The title compound was prepared from the product of step 1 using the procedure detailed in Example 191 step 3; $^{1}$H NMR (CDC13) 3.24 (1H, m), 2.96 (1H, m), 2.82 (1H, m), 2.45 (2H, m), 2.33-2.24 (4H, m), 1.95 (2H, br s), 1.85 (1H, m), 1.73 (2H, m), 1.57 (3H, m), 1.41 (2H, m), 1.31 (1H, m).

Step 3: 4-[1-Ethyl-7-((R)-2-piperidin-1-ylmethyl-pyrrolidin-1-ylmethyl)-1H-imidazo[4,5-c]pyridin-2-yl]-furazan-3-ylamine The title compound was prepared from the product of Step 2 and the product of Example 191 Step 1, using the general procedure of Example 200; MS (ES+), m/e 411 [M+H]$^{+}$.

EXAMPLE 241

4-[1-Ethyl-7-((R)-2-piperazin-1-ylmethyl-cyclopentylmethyl)-1H-imidazo[4,5-c]pyridin-2-yl]-furazan-3-ylamine

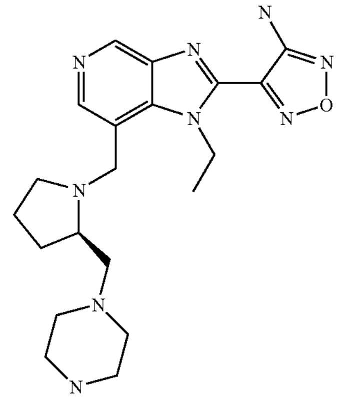

Step 1: 4-(R)-1-Pyrrolidin-2-ylmethyl-piperazine-1-carboxylic acid 9H-fluoren-9-ylmethyl ester trifluoroacetate To a solution of piperazine carboxylic acid 9-fluorenylmethyl ester hydrochloride (690 mg, 2 mmol), in dichloromethane was added diisopropylethylamine (258 mg, 2 mmol) followed by N(t-butoxycarbonyl)D-prolinal (400 mg, 2 mmol) and the resulting solution was stirred for 10 minutes, and treated with sodium triacetoxyborohydride (850 mg, 4 mmol) and stirred for 4 hours at room temperature. The reaction was diluted with water and extracted with dichloromethane at pH 7. The combined organic phase was dried over anhydrous sodium sulfate. The dichloromethane solution was then treated with trifluoroacetic acid (5 ml) and stirred for 16 hours at room temperature. The solvent was evaporated in vacuo to afford the title compound; MS (ES+), m/e 392 $[M+H]^+$.

Step 2: 4-[1-Ethyl-7-((R)-2-piperazin-1-ylmethyl-cyclopentylmethyl)-1H-imidazo[4,5-c]pyridin-2-yl]-furazan-3-ylamine The product of example 191 step 1 (100 mg, 0.387 mmol) was dissolved in 1,2-dichloroethane (2.5 ml) and added to a stirred solution of the product of Step 1 (480 mg, 0.774 mmol) and diisopropyl ethylamine (100 mg, 0.774 mmol) in 1,2-dichloroethane (2.5 ml). After stirring for 5 minutes the reaction was treated with sodium triacetoxyborohydride (164 mg, 0.774 mmol) and the reaction was stirred for 16 hours at room temperature. The reaction was then treated with piperidine (5 ml) and stirred for 5 hours at room temperature. The solvent was then evaporated in vacuo and the residue diluted with dichloromethane, washed with saturated sodium bicarbonate solution, water, brine, dried over anhydrous sodium sulfate and evaporated iv vacuo. The residue was purified by automated reverse phase chromatography (Biotage flex, acetonitrile/water eluant) to afford the title compound (30 mg, 19%); MS (ES+), m/e 412 $[M+H]^+$.

The following compounds were prepared by the general method of Example 200 using ng materials indicated.

| | Example | Aldehyde from Example # | Amine | Characterisation |
|---|---|---|---|---|
| 242 | 4-[1-Ethyl-7-(4-phenylaminomethyl-phenyl)-1H-imidazo[4,5-c]pyridin-2-yl]-furazan-3-ylamine | 191 | Aniline | MS(ES+) m/e 412 $[M + H]^+$ |
| 243 | 4-[1-Ethyl-7-(4-fluoro-3-pyrrolidin-1-ylmethyl-phenyl)-1H-imidazo[4,5-c]pyridin-2-yl]-furazan-3-ylamine | 113 | Pyrrolidine | MS (ES+) m/e 408 $[M + H]^+$ |
| 244 | 4-[1-Ethyl-7-(3-fluoro-4-pyrrolidin-1-ylmethyl-phenyl)-1H-imidazo[4,5-c]pyridin-2-yl]-furazan-3-ylamine | 119 | Pyrrolidine | MS (ES+) m/e 408 $[M + H]^+$ |
| 245 | 4-[1-Ethyl-7-(4-ethylaminomethyl-3-fluoro-phenyl)-1H-imidazo[4,5-c]pyridin-2-yl]-furazan-3-ylamine | 119 | Ethylamine | MS (ES+) m/e 382 $[M + H]^+$ |

EXAMPLE 246

(2-Furazan-3-yl-3-(2-methoxy-phenyl_-3-H-pyrolo (2,3-c)pyridin-4-ylmethyl)-piperidin-4-yl-amine

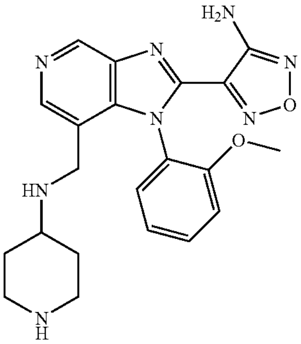

Step 1. (2-Bromo-6-nitro-pyridyl)-(2-methoxy-phenyl)-amine

The title compound was prepared from the product of Example 177, Step 2 and 1-amino-2-methoxybenzene by the general method of Example 25 Step 1. MS (ES+) m/e 324 $[M+H]^+$.

Step 2. 5-Bromo-$N^4$-(2-methoxy-phenyl)-pyridine-3,4-diamine

A solution of the product of Step 1 (1 g, 3.08 mmol) in ethanol (11 ml)/water (2.5 ml)/conc.HCl (1 ml) was stirred at 0° C. and iron filings (1 g, 18.5 mmol) were added protionwise. The mixture was warmed to room temperature and stirred for 18 hours. The mixture was poured onto ice water (100 ml) and basified using 1M sodium carbonate solution. The resulting mixture was filtered through kieselgel and the pad was washed copiously with ethanol. The organic phase was removed in vacuo to leave an orange emulsion, this was extracted into ethyl acetate, washed with water (×3), dried using magnesium sulphate and evaporated in vacuo. Purification of the residue by silica gel chromatography eluting with 2% methanol in dicholomethane afforded the title compound (500 mg, 45%). MS (ES+) m/e 293 $[M+H]^+$.

Step 3. 4-(7-bromo-1 (2-methoxy-phenyl)-1H-imidazo(4,5-c)pyridin-2-yl)-furazan-3-ylamine The title compound was obtained from the product of Step 2 by the general method of Example 1 Steps 3 and 4; MS (ES+) m/e 387 $[M+H]^+$.

Step 4. 2-(4-Amino-furazan-3-yl)-1-(2-methoxy-phenyl)-1H-imidazo[4,5c)pyridine-7-carbaldehyde The title compound was prepared from the product of Step 3 by the general method of Example 191 Step 1; MS (ES+) m/e 337 $[M+H]^+$.

Step 5. 4-((2-(4-Amino-furazan-3-yl)-3-(2-methoxy-phenyl)-3H-pyrrolo(2,3-c)pyridin-4-ylmethyl)-amino)-piperidine-1-carboxylic acid tert butyl ester The title compound was obtained from the product of Step and 4-aminopiperidine-1-carboxylic acid tert butyl ester by the general method of Example 200; MS (ES+) m/e 520 $[M+H]^+$.

Step 6. (2-Furazan-3-yl-3-(2-methoxy-phenyl-3-H-pyrrolo (2,3-c)pyridin-4-ylmethyl)-piperidin yl-amine The product of step 5 was treated according to the general method of Example 191 Step 3.

A solution of the resulting free base (12 mg, 0.03 mmol) in anhydrous methanol (0.5 ml) was treated with 1M hyrdrochloric acid in ether and stirred for 30 minutes. The resulting white precipitate was filtered and dried in vacuo to afford the title compound as a colourless solid (12 mg, 63%); MS (ES+) m/e 420 $[M+H]^+$.

EXAMPLE 247

(3-Cyclopropyl-2-furazan-3-yl-3H-pyrrolo(2,3-c) pyridin-4-ylmethyl)-piperidin-4-yl-amine dihydrochloride

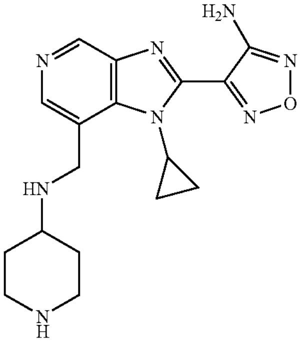

The title compound was prepared from the product of Example 177 Step 3 using the methods of Example 246 Steps 2-6; MS (AP+) m/e 354 $[M+H]^+$.

The following example was prepared by the general method described in Example 247.

| Example | | Amine (C-7) | Characterisation |
|---|---|---|---|
| 248 | 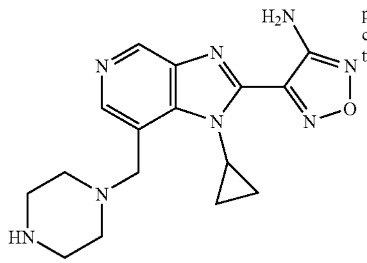 4-(1-Cyclopropyl-7-piperazin-1-ylmethyl-1H-imidazo[4,5-c]pyridin-2-yl)-furazan-3-ylamine | piperazine-1-carboxylic acid tert-butyl ester | MS(AP+) m/e 340 $[M+H]^+$ |

EXAMPLE 249

[2-(4-Amino-furazan-3-yl)-1-methyl-1H-imidazo[4,5-c]pyridin-7-ylmethyl]-piperidin-4-yl-amine

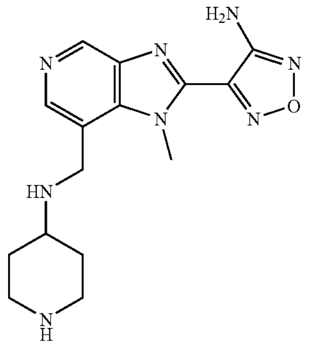

Step 1: N-(2-Bromo-6-nitro-pyridyl)-methylamine

The title compound was prepared from 3-bromo-4-chloro-5-nitropyridine and methylamine by the general method of Example 246 Step 1. MS (ES+) m/e 329 [M+H]$^+$.

Step 2: [2-(4-Amino-furazan-3-yl)-1-methyl-1H-imidazo[4,5-c]pyridin-7-ylmethyl]-piperidin-4-yl-amine The title compound was prepared from the product of Step 1 using the methods of Example 246 Steps 2-6; MS (ES+) m/e 328 [M+H]$^+$.

EXAMPLE 250

1-[2-(4-Amino-furazan-3-yl)-1-ethyl-1H-imidazo[4,5-c]pyridin-7-yl]-1-piperazin-1-yl-methanone dihydrochloride

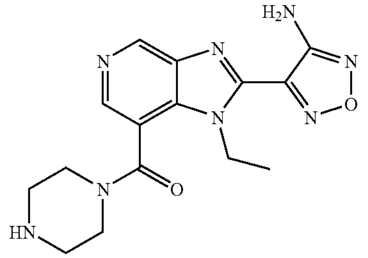

Step 1. 2-(4-Amino-furazan-3-yl)-1-ethyl-1H-imidazo[4,5-c]pyridine-7-carboxylic acid A solution of the product from Example 100 (5 g, 18.25 mmol) in tetrahydrofuran (200 ml) at −78° C. was treated with a 2M solution lithium diisopropylamide (LDA, 18 ml, 36.5 mmol) in hexanes under argon. After 5 minutes the solution was treated with a 1.6M solution of n-butyl lithium (34 ml, 54.7 mmol) in hexanes at −78° C. The mixture was stirred for 10 mins, then carbon dioxide gas was bubbled through the solution for 10 mins. The resulting pale yellow suspension was allowed to warm to room temperature over 2 h, water (10 ml) in tetrahydrofuran (30 ml) was cautiously added dropwise and the mixture concentrated in vacuo. The residual solid was washed with ether (2×100 ml) then dissolved in methanol (100 ml) containing glacial acetic acid. The solvent was evaporated and the residue triturated under ether (50 ml) and filtered to give the title compound as a buff coloured solid (3.28, 74%); MS (ES+) m/e 275 [M+H]$^+$.

Step 2. 4-{1-[2-(4-Amino-furazan-3-ul)-1-ethyl-1H-imidazo[4,5-c]pyridin-7-yl]-methanoyl}-piperazine-1-carboxylic acid, tert-butyl ester.

1,1'-Carbonyldiimdazole (177 mg) was added to a solution of the product from Step 1 (0.1 g, 0.36 mmol) in dry DMF (5 ml) at room temperature under argon. The mixture was stirred for 18 h, then tert-butyl-1-piperazine carboxylate added. The mixture was stirred at room temperature for 16 h, then partitioned between water (15 ml) and ethyl acetate (3×15 ml). The combined organic extracts were washed with brine (2×20 ml), dried over anhydrous sodium sulfate, filtered and evaporated. The residue was purified by silica gel chromatography eluting with dichloromethane/ethanol/ammonia 300:8:1, to afford the title compound, (0.064 g, 40%); MS (ES+) m/e 443 [M+H]$^+$.

Step 3. 1-[2-(4-Amino-furazan-3-yl)-1-ethyl-1H-imidazo[4,5-c]pyridin-7-yl]-1-piperazin-1-yl-methanone, dihydrochloride Ethereal hydrogen chloride (1.0M; 1 ml) was added to a solution of the product from Step 2 (0.064 g, 0.15 mmol) in methanol (1 ml) at room temperature under argon. The mixture was stirred for 16 h, the solvent was evaporated and the residue triturated under ether to give the title compound as a colourless solid (0.047, 79%); MS (ES+) m/e 343 [M+H]$^+$.

EXAMPLE 251

[2-(4-{1-[2-(4-Amino-furazan-3-yl)-1-ethyl-1H-imidazo[4,5-c]pyridin-7-yl]-methanoyl}-piperizin-1-yl)-ethyl]-carbamic acid tert-butyl ester

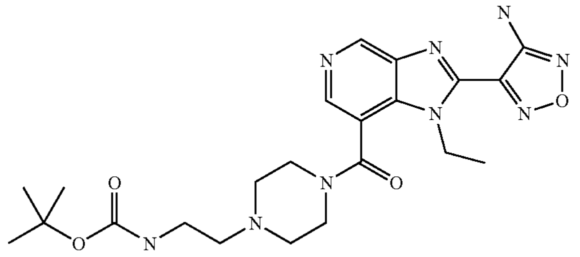

A mixture of the free base from Example 250, Step 3 (prepared by eluting a sample of the dihydrochloride salt through an SCX cartridge using ammonia (10%) in ethanol) and tert-butyl N-(2-oxoethyl)carbamate (0.065 g, 0.41 mmol) in 1,2-dichloroethane (5 ml) was stirred at room temperature for 20 mins. This was then treated according to the method of Example 200 to afford the title compound; MS (ES+) m/e 486 [M+H]$^+$.

EXAMPLE 252

[1-[4-(2-Amino-ethyl)-piperizin-1-yl)-1-[2-(4-amino-furazan-3-yl)-1-ethyl-1H-imidazo[4,5-c]pyridin-7-yl]-methanone. Dihydrochloride

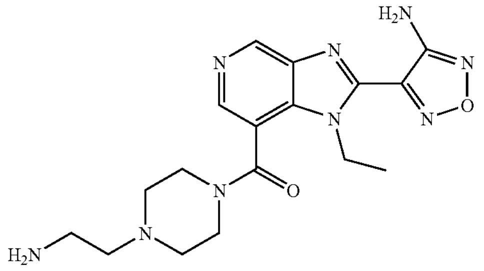

Ethereal hydrogen chloride (1.0M; 1 ml) was added to a solution of the product from example 251 (0.042 g, 0.086 mmol) in methanol (2 ml) and the solution stirred at room temperature for 16 h. The solvent was evaporated and the residual solid triturated under ether (10 ml) and filtered to give the title compound as a colourless solid (0.039 g, 99%); MS (ES+) m/e 386 [M+H]$^+$.

EXAMPLE 253

1-(4-[{-[2-(4-Amino-furazan-3-yl)-1-ethyl-1H-imidazo[4,5-c] pyridin-7-yl]-methanoyl}-piperazin-1-yl)-2-methylamino-ethanone

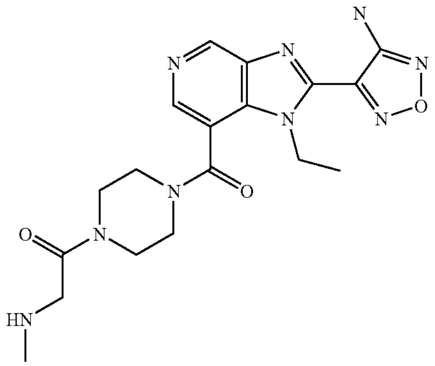

Step 1. [2-(4-{1-[2-(4-Amino-furazan-3-yl)-1-ethyl-1H-imidazo [4,5-c]pyridin-7-yl]-methanoyl}-piperazin-1]-yl)-2-oxo-ethyl]-methyl-carbamic acid tert-butyl ester N-cyclohexylcarbodiimide, N-methyl polystyrene HL (1.69 mmol/g 515 mg, 0.88 mmol) in dichloromethane (2 ml) was treated with Boc-Sarcosine (83 mg, 0.44 mmol), followed by HOBT (59 mg, 0.44 mmol). The mixture was stirred for 10 minutes, then treated with the title compound from Example 250 (75 mg, 0.22 mmol) in triethylamine (92 ul, 0.66 mmol) and dichloromethane (1 ml). The reaction mixture was stirred for 2 hours, then passed down an SCX cartridge eluting methanol the 10% ammonia methanol to afford the title compound (105 mg, 70%) MS (ES+) m/e 513 $[M+H]^+$.

Step 2. 1-(4-[1-[2-(4-Amino-furazan-3-yl)-1-ethyl-1H-imidazo-[4,5-c]pyridin-7-yl]-methanoyl}-piperazin-1-yl)-2-methylamino-ethanone The product of step 1 (105 mg, 0.2 mmol) was dissolved in DCM (2 ml) and hydrochloric acid in ether (1M, 10 equiv.) was added. The mixture was stirred for 16 hours and the resulting white precipitate was filtered and dried in vacuo to afford the title compound as a colourless solid (44 mg, 52%); MS (ES+) m/e 413 $[M+H]^+$.

The following examples were prepared from the product of Example 250. Using the two-step method described in Example 253 Steps 1 and 2.

| | Example | Acid | Characterisation |
|---|---|---|---|
| 254 | 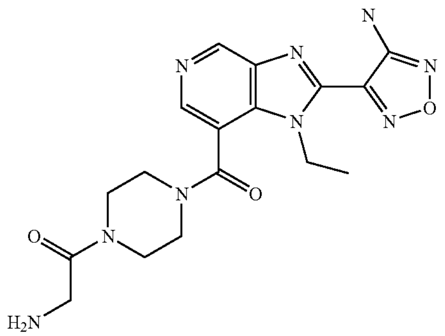 | Boc-Glycine | MS(ES+) m/e 399 $[M+H]^+$ |
| 255 | 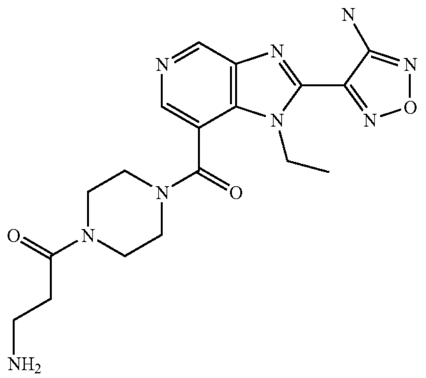 | Boc-Beta-L-alanine | MS(ES+) m/e 413 $[M+H]^+$ |

-continued

| | Example | Acid | Characterisation |
|---|---|---|---|
| 256 | 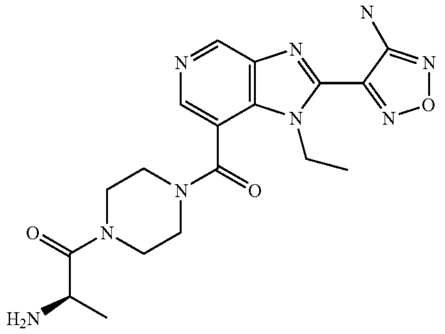 | Boc-L-alanine | MS(ES+) m/e 413 $[M+H]^+$ |
| 257 | 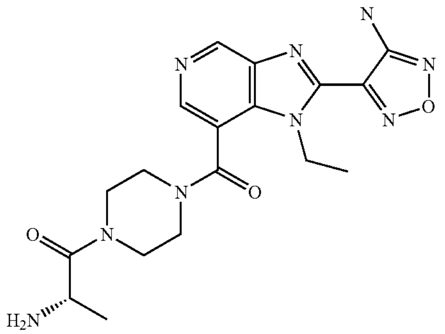 | Boc-D-alanine | MS(ES+) m/e 413 $[M+H]^+$ |
| 258 | 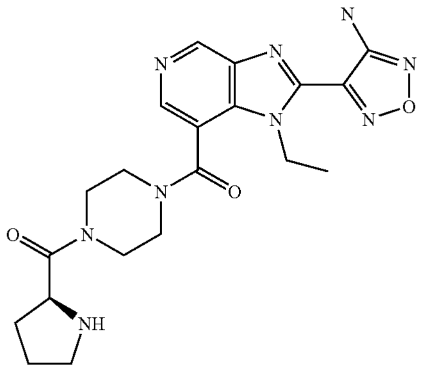 | Boc-L-proline | MS(ES+) m/e 439 $[M+H]^+$ |

The following examples were prepared from the product of Example 250 Step 1 using the two-step method described in example 250 Steps 2 and 3

| | Example | Amine | Characterisation |
|---|---|---|---|
| 259 | 2-(4-Amino-furazan-3-yl)-1-ethyl-1H-imidazo[4,5-c]pyridine-7-carboxylic acid (piperidin-4-yl methyl)-amide dihydrochloride | 4-Aminomethyl piperidin-1-carboxylic acid tert-butyl ester | MS(ES+) m/e 371 $[M + H]^+$ |
| 260 | (+/−) 2-(4-Amino-furazan-3-yl)-1-ethyl-1H-imidazo[4,5-c]pyridine-7-carboxylic acid (piperidin-3-ylamide dihydrochloride | (+/−)-3-Amino piperidine-1-carboxylic acid tert-butyl ester | MS(ES+) m/e 357 $[M + H]^+$ |
| 261 | 2-(4-Amino-furazan-3-yl)-1-ethyl-1H-imidazo[4,5-c]pyridine-7-carboxylic acid | 4-Amino-piperidine-1-carboxylic acid tert-butyl ester | MS(ES+) m/e 357 $[M + H]^+$ |

-continued

| | Example | Amine | Characterisation |
|---|---|---|---|
| | piperidin-4-ylamide dihydrochloride | | |
| 262 | 2-(4-Amino-furazan-3-yl)-1-ethyl-1H-imidazo[4,5-c]pyridine-7-carboxylic acid (3-methylamino-propyl)-amide dihydrochloride | (3-Amino-propyl)-methyl-carbamic acid tert-butyl ester | MS(ES+) m/e 345 $[M + H]^+$ |
| 263 | 2-(4-Amino-furazan-3-yl)-1-ethyl-1H-imidazo[4,5-c]pyridine-7-carboxylic acid (4-amino-butyl)-amide dihydrochloride | (4-Amino-butyl)-carbamic acid tert butyl ester | MS(ES+) m/e 345 $[M + H]^+$ |
| 264 | 2-(4-Amino-furazan-3-yl)-1-ethyl-1H-imidazo[4,5-c]pyridine-7-carboxylic acid (6-amino-hexyl)-amide dihydrochloride | (6-Amino-hexyl)-carbamic acid tert butyl ester | MS(ES+) m/e 373 $[M + H]^+$ |
| 265 | (+/−)-2-(4-Amino-furazan-3-yl)-1-ethyl-1H-imidazo[4,5-c]pyridine-7-carboxylic acid (piperidin-2-yl methyl)-amide dihydrochloride | 2-Aminomethyl-piperidine-1-carboxylic acid tert-butyl ester | MS(ES+) m/e 471 $[M + H]^+$ |
| 266 | 1-[2-(4-Amino-furazan-3-yl)-1-ethyl-1H-imidazo[4,5-c]pyridine-7-yl]-1-((R)-3-amino-pyrrolidin-1-yl)-methanone dihydrochloride | (R)-Pyrrolidin-3-yl-carbamic acid tert-butyl ester | MS(ES+) m/e 343 [M + H]* [alpha]D(27.6)C = -3.34 (c = 2.75%, DMF) |
| 267 | 1-[2-(4-Amino-furazan-3-yl)-1-ethyl-1H-imidazo[4,5-c]pyridine-7-yl]-1-((S)-3-amino-pyrrolidin-1-yl)-methanone dihydrochloride | (S)-Pyrrolidin-3-yl-carbamic acid tert-butyl ester | MS(ES+) m/e 343 $[M + H]^+$ [alpha]D(27.2)C = +1.31 (c = 3.75%, DMF) |
| 268 | 2-(4-Amino-furazan-3-yl)-1-ethyl-1H-imidazo[4,5-c]pyridine-7-carboxylic acid (R)-pyrrolidin-3-ylamide dihydrochloride | (R)-3-Amino-pyrrolidine-1-carboxylic acid tert-butyl ester | MS(ES+) m/e 343 $[M + H]^+$ |
| 269 | 2-(4-Amino-furazan-3-yl)-1-ethyl-1H-imidazo[4,5-c]pyridine-7-carboxylic acid (S)-pyrrolidin-3-ylamide dihydrochloride | (S)-3-Amino-pyrrolidine-1-carboxylic acid tert-butyl ester | MS(ES+) m/e 343 $[M + H]^+$ |
| 270 | 2-(4-Amino-furazan-3-yl)-1-ethyl-1H-imidazo[4,5-c]pyridine-7-carboxylic acid (morpholin-2-ylmethyl)-amide dihydrochloride | 2-Aminomethyl-morpholine-4-carboxylic acid tert-butyl ester | MS(ES+) m/e 373 $[M + H]^+$ |

EXAMPLE 271

2-(4-Amino-furazan-3-yl)-1-ethyl-1H-imidazo[4,5-c]pyridine-7-carboxylic acid[1-(2-amino-ethanoyl)-piperidine-4-yl]-amide dihyrochloride

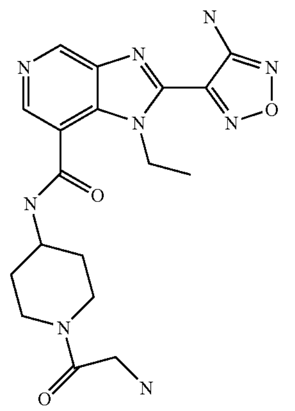

Step 1. {2-(4-Amino-furazan-3-yl)-1-ethyl-1H-imidazo[4,5-c]pyridine-7-yl]-methanoyl}-amino)-piperidin-1-yl]-2-oxo-ethyl}-carbamic acid tert-butyl ester A mixture of N-cyclohexylcarbodiimide, N-methyl polystyrene HL (1.69 mmol/g; 300 mg, 0.507 mmol) and tert-butoxycarbonylamino-acetic acid (82 mg, 0.466 mmol) in dry dichloromethane (3 ml) was stirred for 10 mins at room temperature under argon. 1-hydroxybenzotriazole hydrate (HOBT; 71 mg 0.466 mmol) was added and the mixture stirred for a further 10 mins. A solution of the product from example 261 (0.1 g, 0.233 mmol) and triethylamine (0.1 ml, 0.507 mmol) in dry DMF (3 ml) was added and the mixture stirred for 16 h. The mixture was then applied to a SCX ion exchange column, eluted with methanol and then a mixture of methanol/0.880 ammonia (9:1). The basic fractions were then evaporated and the residual solid triturated under ether and filtered to afford the title compound, (0.067 g, 56%); MS (ES+) m/e 514 $[M+H]^+$.

Step 2 . 2-(4-Amino-furazan-3-yl)-1-ethyl-11H-imidazo[4,5-c]pyridine-7-carboxylic acid[1-(2-amino-ethanoyl)-piperidine-4-yl]-amide dihyrochloride Ethereal hydrogen chloride (1.0M; 2 ml) was added to a solution of the product from Step 1 (0.067 g, 0.13 mmol) in methanol (3 ml) at room temperature under argon. The mixture was stirred for 16 h, the solvent was evaporated and the residue triturated under ether to give the title compound as a colourless solid (0.058, 79%); MS (ES+) m/e 414 $[M+H]^+$.

The following examples were prepared from the product of Example 261 using the two-step method described in Example 271 Step 1

| | Example | Acid | Characterisation |
|---|---|---|---|
| 272 | 2-(4-Amino-furazan-3-yl)-1-ethyl-1H-imidazo[4,5-c]pyridine-7-carboxylic acid [1-(3-amino-propanoyl)-piperidin-4-yl]-amide dihydrochloride | 3-Amino-propionic acid | MS(ES+) m/e 428 $[M + H]^+$ |
| 273 | 2-(4-Amino-furazan-3-yl)-1-ethyl-1H-imidazo[4,5-c]pyridine-7-carboxylic acid [1-((s)-1-pyrrolidin-2-yl-methanoyl)-piperidin-4-yl]-amide dihydrochloride | (S)-Pyrrolidine-2-carboxylic acid | MS(ES+) m/e 454 $[M + H]^+$ |

The following examples were prepared from the product of Example 250 Step 1 using the method described in example 250 Step 2

| | Example | Amine | Characterisation |
|---|---|---|---|
| 274 | 1-[2-(4-Amino-furazan-3-yl)-1-ethyl-1H-imidazo[4,5-c]pyridin-7-yl]-1-pyrrolidin-1-yl-methanone | pyrrolidine | MS(ES+) m/e 328 $[M + H]^+$ |

EXAMPLE 275

1-[2-(4-Amino-furazan-3-yl)-1-ethyl-1H-imidazo[4,5-c]pyridin-7-yl]-1-(S)-2-pyrrolidin-1-ylmethyl-pyrrolidin-1-yl)-methanone dihydrochloride

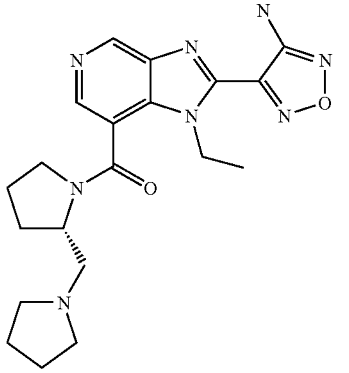

Step 1 1-[2-(4-Amino-furazan-3-yl)-1-ethyl-1H-imidazo[4,5-c]pyridin-7-yl]-1-imidazol-1-yl-methanone 1,1'-Carbonyldiimdazole (0.89 g) was added to a solution of the product from Example 250 Step 1 (0.5 g, 1.82 mmol) in dry DMF (10 ml) at room temperature under argon. The mixture was stirred for 18 h resulting in the precipitation of a colourless solid. Ether (10 ml) was added and the solid filtered to give the title compound, (0.5 g, 85%); MS (ES+) m/e 325 $[M+H]^+$.

Step 2 1-[2-(4-Amino-furazan-3-yl)-1-ethyl-1H-imidazo[4,5-c]pyridin-7-yl]-1-((S)-2-pyrrolidin-1-ylmethyl-pyrrolidin-1-yl)-methanone A mixture of (S)(+)-1-(2-pyrrolidinylmethyl)pyrrolidine (0.142 g; 0.93 mmol) and the product from Step 1 (0.1 g; 0.31 mmol) in DMF (2 ml) was warmed at 60° C. for 18 h. The cooled mixture was partitioned between water (10 ml) and ethyl acetate (3×10 ml). The combined organic extracts were washed with brine (2×20 ml), dried over anhydrous sodium sulphate, filtered and evaporated to give a colourless gum. The crude material was purified by preparative HPLC using Dynamax C18 column, 8 micron particle size; 250 mm×41.4 mm i.d.; 10-90% acetonitrile/water (0.1% TFA); 70 ml/min; UV detection at 254 nm) to afford the title compound, (0.055 g, 28%); MS (ES+) m/e 411 $[M+H]^+$.

EXAMPLE 276

2-(4-Amino-furazan-3-yl)-1-ethyl-1H-imidazo[4,5-c]pyridine-7-carboxylic acid (R)-pyrrolidin-3-yl amide

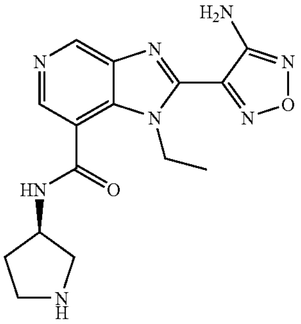

The product of Example 275 Step 1 (150 mg) and (R>3-amino-1-pyrrolidine-1-carboxylic acid tert-butyl ester (172 mg) were reacted according to the general method of Example 275, Step 2 followed by the general method described in example 250 step 3 to give the title compound; MS (ES+) m/e 443 $[M+H]^+$.

The following example was prepared by the general method described in Example 276

| | Example | Amine | Characterisation |
|---|---|---|---|
| 277 | 2-(4-Amino-furazan-3-yl)-1-ethyl-1H-imidazo[4,5-c]pyridine-7-carboxylic acid (R)-pyrrolidin-3-yl amide | (R)-3-amino-1-pyrrolidine-1-carboxylic acid tert-butyl ester | MS (ES+) m/e 367 $[M + H]^+$ |

EXAMPLE 278

2-(4-Amino-furazan-3-yl)-1-ethyl-1H-imidazol-4,5-c]pyridine-7-carboxylic acid (2-piperizin-1-yl-ethyl)-amide dihydrochloride

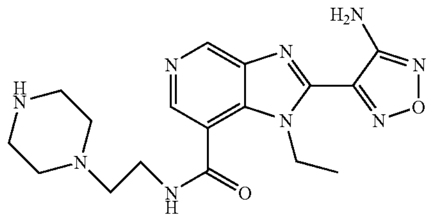

Step 1. 4-[2-({1-[2-(4-Amino-furazan-3-yl)-1-ethyl-1H-imidazo[4,5-c]pyridine-7-yl]-methanoyl}-amino)-ethyl]-piperizin-1-carboxylic acid benzyl ester The product of Example 250 Step 1 and 4-(2-amino-ethyl)-piperizine-1-carboxylic acid benzyl ester were reacted according to the general method of Example 250, Step 2 to give the title compound; MS (ES+) m/e 520 $[M+H]^+$.

Step 2-(4-Amino-furazan-3-yl)-1-ethyl-1H-imidazo[4,5-c] pyridine-7-carboxylic acid (2-piperizin-1-yl-ethyl)-amide dihydrochloride Hydrogen bromide (30% in acetic acid; 0.5 ml) was added to a solution of the product from Step 1 (0.085 g, 0.165 mmol) in dry dichloromethane (5 ml) at room temperature under argon. The mixture was stirred for 10 mins. resulting in the precipitation of a colourless solid which was filtered off, partitioned between sodium carbonate solution (2N, 5 ml) and ethyl acetate (2×10 ml). The combined organic extracts were dried (Na2SO4), evaporated, dissolved in methanol (2 ml) and ethereal HCl (1.0M; 0.5 ml) added. The solvent was then evaporated and the residue triturated with ether (2 ml) and filtered to give the title compound (16 mg, 21%); MS (ES+) m/e 386 $[M+H]^+$.

EXAMPLE 279

[4-(7-Bromo-1-ethyl-1H-imidazo[4,5-c]pyridin-2-yl)-furazan-3-yl]-carbamic acid tert-butyl ester

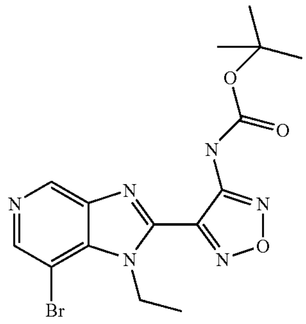

A solution of the product from Example 100 (1.0 g, 3.23 mmol) in dichloroethane (5 mL) and pyridine (10 mL) was treated with DMAP (0.435 g, 3.56 mmol) and $BoC_2O$ (1.06 g, 4.85 mmol). The solution was heated to 70° C. and was stirred overnight. The reaction is not complete, so more DMAP (0.197 g, 1.62 mmol) and $Boc_2O$ (0.353 g, 1.62 mmol) were added, and the reaction mixture was stirred overnight. The reaction mixture was then cooled, and concentrated in-vacuo. The black residue was dissolved up in $H_2O$ and EtOAc, and the product was extracted into the organic layer. The layers were separated, and the organic layer was dried over $Na_2SO_4$, filtered, and concentrated to give the pure product as a tan solid (1.25 g, 95%); MS (ES+) m/e 410 $[M+H]^+$.

EXAMPLE 280

4-[7-((S)-3-Amino-pyrrolidine-1-sulfonyl)-1-ethyl-1H-imidazo[4,5-c]pyridin-2-yl]-furazan-3-ylamine

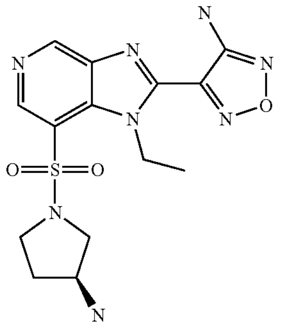

Step 1. {4-[7-((S)-3-tert-Butoxycarbonylamino-pyrrolidine-1-sulfonyl)-1-ethyl-1H-imidazo[4,5-c]pyridin-2-yl]-furazan-3-yl)-carbamic acid tert-butyl ester A solution of the product from Example 279 (0.150 g, 0.367 mmol) in tetrahydrofuran (2 ml) at ambient temperature was treated with NaH (60%) under Argon. After 10 minutes, the mixture was cooled to −78° C., and was treated with n-butyllithium. After 10 minutes, the mixture was treated with a $SO_2$ solution (2 mL), formed from bubbling $SO_2$ gas into THF (2 mL). After 10 minutes of stirring, the mixture was treated with $SO_2Cl_2$, and was allowed to warm to ambient temperature. The reaction mixture was then concentrtated, in-vacuo, to dryness. The solid was dissolved in dichloromethane (2.5 mL) and pyridine (2.5 mL) under Argon, and was treated with the amine (0.085 g, 0.46 mmol), and was stirred at ambient temperature overnight. The completed reaction was concentrated down to afford the title compound; MS (ES+) m/e 580 $[M+H]^+$.

Step 2. 4-[7-((S)-3-Amino-pyrrolidine-1-sulfonyl)-1-ethyl-1H-imidazo[4,5-c]pyridin-2-yl]-furazan-3-ylamine The title compound was prepared by dissolving the product, from Step 1, in a minimal amount of MeOH, and adding 1 mL of a 1M solution of HCl in $Et_2O$. The mixture was stirred for 6 hours, then concentrated in-vacuo to dryness, taken up in DMSO, and purified via reverse-phase HPLC to give the title compound (0.0443 g, 32%); MS (ES+) m/e 379 $[M+H]^+$.

The following examples were prepared from the product of Example 279 using the method described in Example 280.

| | Example | Amine | Characterisation |
|---|---|---|---|
| 281 | 2-(4-Amino-furazan-3-yl)-1-ethyl-1H-imidazo[4,5-c]pyridine-7-sulfonic acid methylamide | Methylamine | MS (ES+) m/e 324 $[M + H]^+$ |
| 282 | 2-(4-Amino-furazan-3-yl)-1-ethyl-1H-imidazo[4,5-c]pyridine-7-sulfonic acid dimethylamide | Dimethylamine | MS (ES+) m/e 338 $[M + H]^+$ |

EXAMPLE 283

2-(4-Amino-furazan-3-yl)-1-ethyl-1H-imidazo[4,5-c]pyridin-7-ol

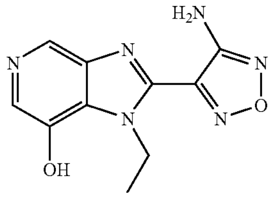

A solution of the product from Example 100 (2.6 g, 8.41 mmol) in tetrahydrofuran (180 ml) at −78° C. was treated with a 2.5M solution of n-butyllithium (8.41 ml, 21.03 mmol) in hexanes. After the addition was complete the mixture was treated with trimethylborate (2.62 g, 25.23 mmol) and allowed to reach room temperature. After 1.5 hours at room temperature the reaction was carefully quenched with 3M aq. NaOH (12.5 ml) followed by a 30% aqueous hydrogen peroxide solution (4.3 ml). After 45 minutes the reaction was acidified with 2M hydrochloric acid and then applied to a SCX ion exchange column and eluted with methanol and then a mixture of methanol/0.880 ammonia (9:1). The basic fractions were then reduced and the solid residue was triturated with dichloromethane and filtered to afford the title compound, (1.2 g, 58%); MS (ES+) m/e 247 $[M+H]^+$.

EXAMPLE 284

4-[1-Ethyl-7-(piperidin-4-ylmethoxy)-1H-imidazo[4,5-c]pyridin-2-yl]-furazan-3-ylamine

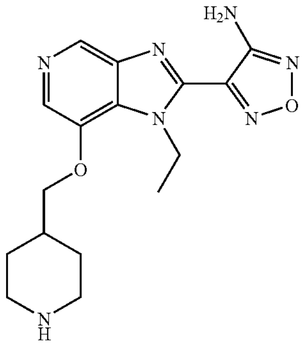

Step 1. 4-[2-(4-Amino-furazan-3-yl)-1-ethyl-1H-imidazo[4,5-c]pyridin-7-yloxymethyl]-piperidine-1-carboxylic acid tert-butyl ester A mixture of the product from Example 283 (0.1 g, 0.406 mmol) and $K_2CO_3$ (0.112 g, 0.812 mmol) in acetone (3 ml) at −78° C. was treated with 4-iodomethylpiperidine-1-carboxylic acid tert-butyl ester (Villalobos, A; et al, *J. Med. Chem.,* 1994, 37(17), 2721) (0.145 g, 0.447 mmol) and heated at reflux for 18 hours. A further portion of 4-iodomethylpiperidine-1-carboxylic acid tert-butyl ester (0.145 g, 0.447 mmol) was then added and the heating continued for a further 6 hours. The reaction was then cooled, poured into water, extracted with dichloromethane, dried with $NaSO_4$ and reduced. The residue was chromatographed on silica gel eluting with ethyl acetate to afford the title compound, (0.071 g, 39%); MS (ES+) m/e 444 $[M+H]^+$.

Step 2. 4-[1-Ethyl-7-(piperidin-4-ylmethoxy)-1H-imidazo[4,5-c]pyridin-2-yl]-furazan-3-ylamine The product from Step 1 (0.071 g, 0.16 mmol) was stirred in trifluoroacetic acid (0.5 ml) and dichloromethane (1 ml) at room temperature for 1 hour and the solution was then co-evaporated three times with dichloromethane. The residue was purified by silica gel chromatography eluting with 0.880 ammonia:methanol:dichloromethane (1:9:90), to afford the title compound, (0.046 g, 83%); MS (ES+) m/e 334 $[M+H]^+$.

EXAMPLE 285

4-[1-Ethyl-7-(piperidin-4-yloxy)-1H-imidazo[4,5-c]pyridin-2-yl]-furazan-3-ylamine

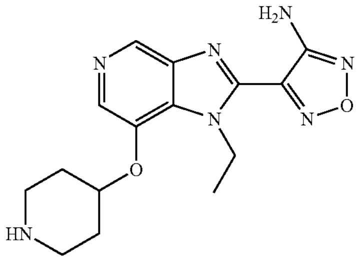

Step 1: 4-[2-(4-Amino-furazan-3-yl)-1-ethyl-1H-imidazo[4,5-c]pyridin-7-yloxy]-piperidine-1-carboxylic acid tert-butyl ester A mixture of the product from Example 283 (0.1 g, 0.406 mmol), 4-hydroxy-piperidine-1-carboxylic acid tert-butyl ester (0.074 g, 0.369 mmol) and tributylphosphine (0.074 g, 0.369 mmol) in tetrahydrofuran (5 ml) was treated with 1,1'-(Azodicarbonyl)-dipiperidine (0.093 g, 0.369 mmol) and heated at reflux for 18 hours. The reaction was then cooled to RT and then applied to a SCX ion exchange column and eluted with methanol and then a mixture of methanol/0.880 ammonia (9:1). The basic fractions were then reduced and the solid residue chromatographed on silica gel eluting with ethyl acetate to afford the title compound, (0.03 g, 17%); MS (ES+) m/e 430 $[M+H]^+$.

Step 2: 4-[1-Ethyl-7-(piperidin-4-yloxy)-1H-imidazo[4,5-c]pyridin-2-yl]-furazan-3-ylamine The product from Step 1 (0.03 g, 0.07 mmol) was treated according to the method of Example 284 Step 2 to afford the title compound, (0.02 g, 87%); MS (ES+) m/e 330 $[M+H]^+$.

EXAMPLE 286

4-{1-ethyl-7-[(E)-2-(4-methoxyphenyl)-vinyl]-1H-imidazo[4,5-c]pyridin-2-yl}furazan-3-ylamine

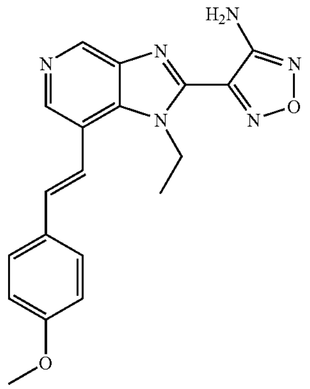

The product of example 100 (309 mg, 1 mmol), 4-methoxystyrene (167 uL, 1.25 mmol), palladium(II) acetate (12 mg, 0.05 mmol), o-tolyltriphenylphosphine (30 mg, 0.10 mmol) and triethylamine (349 uL, 2.5 mmol) were heated at 130° C. for 4 hours. The solution was partitioned between ethyl acetate and water, extracting with ethylacetate (×3). Combined extracts were washed with water (×3), brine, dried over anhydrous magnesium sulfate and concentrated to a crude solid, 450 mg, then purified by column chromatography eluting with 1:9:90.880 ammonia:ethanol:dichloromethane affording the title product, 176 mg (49%); MS (ES+) m/e 363 $[M+H]^+$.

EXAMPLE 287

4-[1-Ethyl-7-(2-piperidin-4-yl-ethyl)1H-imidazo[4,5-c]pyridin-2-yl]-furazan-3-ylamine

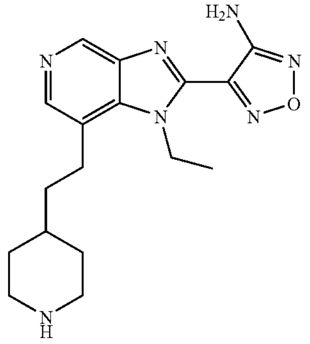

A solution of 4-vinyl-piperidine-1-carboxylic acid tert-butyl ester (WO 9620192) (1.2 mM: 252 mg) in dry tetrahydrofuran (4 ml) was treated with a 0.5M solution of 9-borabicyclo[3.3.1]-nonane in tetrahydrofuran (1.2 mM; 2.4 ml) and stirred at room temperature for 6 hours under argon. The mixture was treated with the product of Example 100 (1.0 mM; 309 mg), 1,1'-bis(diphenylphosphino)ferrocene dichloro palladium(II) complex with dichloromethane (25 mg) and a 3M aqueous solution of sodium hydroxide (1 ml). The resulting mixture was heated at reflux under argon for 18 hours and purified on a 5 g SCX ion exchange cartridge. After removal of the solvent in vacuo the resulting yellow gum was treated with trifluoroacetic acid at room temperature for 2 hours and the solution passed through a 5 g SCX ion exchange cartridge. The solvent was removed in vacuo and the residue purified on a 5 g silica solid phase extraction cartridge eluting with 1-5-94 ammonia-methanol-dichloromethane to give the title compound as a white solid (23 mg). MS (ES+) m/e 342 $[M+H]^+$.

EXAMPLE 288

4-(1-Ethyl-5-oxy-1H-imidazo[4,5-c]pyridin-2-yl)furazan-3-ylamine

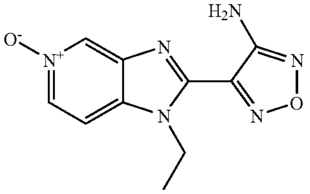

A solution of the product of Example 1 (200 mg, 0.869 mmol) in acetic acid (2 ml) was treated with hydrogen peroxide (30%, 0.108 mg, 0.957 mmol) and the mixture heated 90° C. for 5 hours. After cooling to room temperature the mixture was poured into sodium carbonate solution and extracted with dichloromethane (×4). The organic phase was dried, the solvent was evaporated in vacuo and the residue purified by silica gel chromatography eluting with 15% methanol in dichloromethane, to afford the title compound (130 mg, 53%); MS (ES+) m/e 247 $[M+H]^+$.

EXAMPLE 289

4-(4-Chloro-1-ethyl-1H-imidazol-[4,5-c]pyridin-2-yl)furazan-3-ylamine

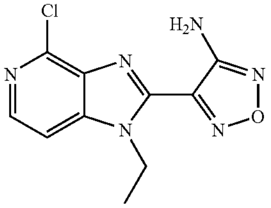

A solution of the product of Example 288 (80 mg, 0.325 mmol) in phosphorus oxychloride (4 ml) was heated at 120° C. for 6 hours. After cooling to room temperature the mixture was concentrated in vacuo and the residue partitioned between dichloromethane and saturated sodium hydrogen carbonate solution. The organic phase was dried and the solvent was evaporated in vacuo to afford the title compound (81 mg, 100%) which was used directly in the next reaction; MS (ES+) m/e 265/267 $[M+H]^+$.

EXAMPLE 290

4-(1-Ethyl-4-phenyl-1H-imidazo[4,5-c]pyridin-2-yl) furazan-3-ylamine

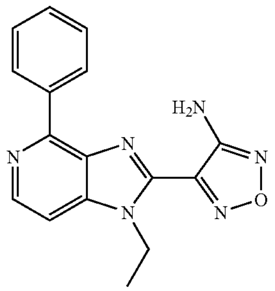

The title compound was prepared from the product of Example 289 and phenylboronic acid by the general method described in Example 49. MS (ES+) m/e 307 $[M+H]^+$.

EXAMPLE 291

4-(1-Ethyl-4-methyl-1H-imidazo[4,5-c]pyridin-2-yl)-furazan-3-ylamine

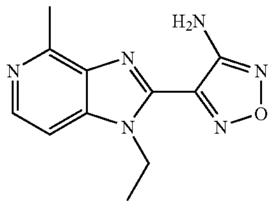

A solution of the product of Example 289 (0.1 g, 0.377 mmol) in 1,4-dioxan (8 ml) was treated with a 2M solution of trimethylaluminium (0.378 ml, 0.755 mmol) in toluene and bis(triphenylphosphine)palladium(II) dichloride (0.026 g, 0.0377 mmol). The mixture was heated at reflux for 4 hours and then cooled to room temperature, quenched carefully with water, poured into dichloromethane and washed with saturated sodium bicarbonate solution. The organic layer was then dried, reduced and the residue chromatographed on silica gel eluting with a mixture of dichloromethane and methanol (9.5/0.5) to afford the title compound, (0.022 g, 13%); MS (ES+) m/e 245 $[M+H]^+$.

EXAMPLE 292

4-(7-Bromo-1-ethyl-4-methyl-1H-imidazo[4,5-c] pyridin-2-yl)-furazan-3-ylamine

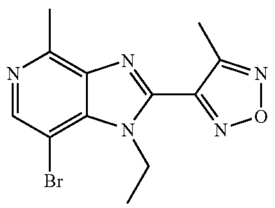

The title compound was prepared from 2-methyl-3-nitropyridin-4-ol (*J. Med. Chem.* 1989, 32, 2474-2485), using the procedures detailed in example 100 step 1, and example 36 steps 1, 2 and 3; MS (ES+), m/e 323/325 $[M+H]^+$.

EXAMPLE 293

[2-(4-Amino-furazan-3-yl)-7-bromo-1-ethyl-1H-imidazo[4,5-c]pyridin-4-yl]-methanol

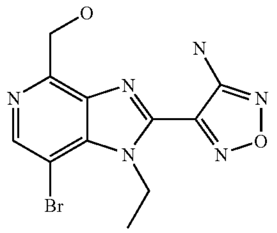

Step 1: 4-(7-Bromo-1-ethyl-4-methyl-5-oxy-1H-imidazo[4,5-c]pyridin-2-yl)-furazan-3-ylamine The title compound was prepared from the product of Example 292 using the procedure detailed in example 155; MS (ES+), m/e 339/341 $[M+H]^+$.

Step 2: Acetic Acid 2-(4-amino-furazan-3-yl)-7-bromo-1-ethyl-1H-imidazo[4,5-c]pyridin-4-ylmethyl ester The product of step 1 (565 mg, 1.66 mmol) was added to preheated acetic anhydride (5 ml, 53 mmol) at 110° C. and stirred for 1 hour. The reaction was then cooled to RT and applied to a Mega Bond Elute SCX ion exchange column and eluted with methanol and then a mixture of methanol/0.880 ammonia (9:1). The basic fractions were reduced and the solid residue chromatographed on silica gel eluting with a mixture of dichloromethane/diethyl ether (9:1) to afford the title compound (300 mg, 43%); MS (ES+), m/e 423/425 $[M+H]^+$.

Step 3: [2-(4-Amino-furazan-3-yl)-7-bromo-1-ethyl-1H-Imidazo[4,5-c]pyridin-4-yl]-methanol To a suspension of the product of step 2 (312 mg, 0.74 mmol) in methanol (10 ml) was added a 2M aqueous solution of sodium hydroxide (1.1 ml, 2.21 mmol) and the reaction heated at reflux for 1 hour. The reaction was then diluted with water (20 ml) and aged at room temperature for 2 hours. The resulting precipitate was collected, washed with water and dried in vacuo at 45° C. for 16 hours to afford the title compound (220 mg, 88%); MS (ES+), m/e 339/341 $[M+H]^+$.

EXAMPLE 294

4-(1-Ethyl-4-pyrazol-1-yl-1H-imidazo[4,5-c]pyridin-2-yl)-furazan-3-ylamine

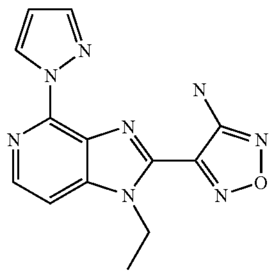

To a solution of pyrazole (472 mg, 6.96 mmol) in dimethylformamide (4 ml) at 0° C. was added portionwise sodium hydride (60% dispersion in mineral oil, 167 mg, 6.96 mmol). The reaction was then treated with a solution of the product of example 289 (200 mg, 0.87 mmol) in dimethylformamide (2 ml) and heated at 60° C. for 3 days. The reaction was cooled and diluted with ethyl acetate (25 ml), then washed sequentially with saturated sodium bicarbonate solution, water, brine, dried over anhydrous sodium sulfate and evaporated in vacuo. The residue was purified using silica gel chromatography eluting with a mixture of 0.880 ammonia:methanol:dichloromethane (5:95) to afford the title product (30 mg, 12%). MS (ES+) m/e 297 $[M+H]^+$.

EXAMPLE 295

4-(1-Cyclopropyl-6-methoxy-1H-imidazo[4,5-c]pyridin-2-yl)-furazan-3-ylamine

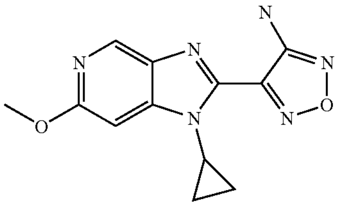

Step 1. 4-Methoxy-5-nitro-1H-pyridin-2-one

To a stirred solution of potassium tert-butoxide (2.8 g, 25 mmol) in liquid ammonia (30 ml) at −30° C. was added dropwise a solution of 4-methoxy-3-nitropyridine (1.54 g, 10 mmol), tert-butyl hydroperoxide (5M in decane, 2.2 ml, 11 mmol) in tetrahydrofuran (10 ml) over 20 minutes. After stirring at −30° C. for 30 minutes saturated ammonium chloride solution (ca 5 ml) was cautiously added and the mixture allowed to warm to room temperature. The ammonia was evaporated and the residue diluted with water (50 ml). The resulting solid was collected, washed with water and dried to give the title compound (1.24 g, 73%). MH (ES+) m/e 171 $[M+H]^+$.

Step 2. 2-Chloro-4-methoxy-5-nitropyridine

A stirred solution of phosphorous oxychloride (8 ml) and N,N-diethylaniline (1.9 ml, 12 mmol) at 0° C. was treated with the product of Step 1 (1.7 g, 10 mmol). The mixture was heated at reflux for 3 hours and then cooled to room temperature. The mixture was evaporated in vacuo and the residue co-evaporated with toluene. The residue was added to ice-water and the solution extracted with ethyl acetate. The organic phase was dried and evaporated in vacuo to give the title compound (1.78 g, 94%). $^1H$ NMR ($CDCl_3$) 8.82 (1H, s), 7.05 (1H, s), 4.06 (3H, s).

Step 3. 2,4-Dimethoxy-5-nitropyridine

A solution of the product of Step 2 (950 mg, 5 mmol), sodium methoxide (695 mg, 12.5 mmol) in methanol (10 ml) was heated at reflux for 2 hours. After cooling the solvent was removed in vacuo and the residue partitioned between ethyl acetate and water. The organic phase was washed with water and brine, dried and evaporated in vacuo to give the title compound (900 mg, 98%). MS (ES+) m/e 185 $[M+H]^+$.

Step 4. 4-(1-Cyclopropyl-6-methoxy-1H-imidazo[4,5-c]pyridin-2-yl)-furazan-3-ylamine The title compound was prepared from the product of Step 3 using the methods described in Example 2 Step 1, followed by Example 1 Steps 2-4; MS (AP+) m/e 273 $[M+H]^+$.

EXAMPLE 296

4-(1-Ethyl-6-methoxy-1H-imidazo[4,5-c]pyridin-2-yl)-furazan-3-ylamine

The title compound was prepared from the product of Example 295, Step 3 and ethylamine using the methods described in Example 2, Step 1 followed by Example 1, Steps 2-4; MS (ES+) m/e=261 $[M+H]^+$.

EXAMPLE 297

4-(1-Cyclopropyl-6-phenoxy-1H-imidazo[4,5-c]pyridin-2-yl)-furazan-3-ylamine

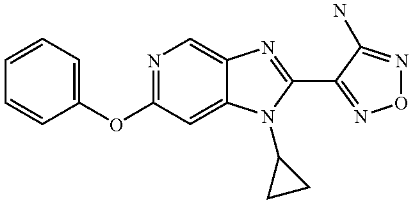

Step 1. 4-Methoxy-5-nitro-2-phenoxypyridine

A solution of phenol (226 mg, 2.4 mmol) in N,N-dimethylformamide (5 ml) was treated with sodium hydride (144 mg, 60% dispersion in oil, 2.4 mmol). After stirring at room temperatures for 10 minutes the suspension was added to a solution of the product of Example 295 Step 2 (377 mg, 2 mmol) in N,N-dimethylformamide (2 ml). After 2 hours saturated ammonium chloride solution was added and the solution was extracted with ethyl acetate. The organic phase was washed with water and brine, dried and concentrated in vacuo to give the title compound which was used directly in subsequent steps. MS (AP+) m/e 247 $[M+H]^+$.

Step 2. 4-(1-Cyclopropyl-6-phenoxy-1H-imidazo[4,5-c]pyridin-2-yl)furazan-3-ylamine The title compound was prepared from the product of Step 1 using the methods described in Example 2 Step 1, followed by Example 1 Steps 24; MS (AP+) m/e 335 $[M+H]^+$.

EXAMPLE 298

4-(1-Ethyl-6-phenoxy-1H-imidazo[4,5-c]pyridin-2-yl)furazan-3-ylamine

Step 1. 2-Chloro-4-(ethylamino)-5-nitropyridine

A solution of 4-(ethylamino)-2-methoxy-5-nitropyridine (5.0 g, 25.3 mmol) in $POCl_3$ (25 mL) was heated to 100° C. in a sealed tube for 1 week. The reaction mixture was cooled and concentrated and the residue was taken up in EtOAc/$H_2O$ and carefully quenched with sat. $K_2CO_3$. The aqueous layer was extracted with EtOAc, washed with $H_2O$, dried ($MgSO_4$) and concentrated to give an orange oil which solidified on standing which was used without further purification. MS (ES+) m/e 202 $[M+H]^+$.

Step 2. 4-(Ethylamino)-5-nitro-2-phenoxypyridine

A solution of sodium phenoxide (prepared from phenol and NaH) (6 mmol) in THF (3 mL) was added to a solution of the product from Step 1 (600 mg, 3.0 mmol) in THF (2 mL) and the resulting solution was heated to reflux overnight. The solution was cooled, poured into $H_2O$ and extracted with EtOAc. The organic layers were washed with $H_2O$ and brine, dried, filtered and concentrated to give a residue which was purified by column chromatography (5-80% EtOAc in hex) to give the title compound which was used directly in the next step. MS (ES+) m/e 260. $[M+H]^+$.

Step 3. 4-(1-Ethyl-6-phenoxy-1H-imidazo[4,5-c]pyridin-2-yl)furazan-3-ylamine

The title compound was prepared from the product of Step 2 using the methods described in Example 1 Steps 2-4; MS (ES+) m/e 323 $[M+H]^+$.

The following compounds were prepared from the product of Example 298, Step 1, by the method of Example 298 Steps 2-3.

| | Example | Phenol | Characterisation |
|---|---|---|---|
| 299 | 4-(1-Ethyl-6-(4-fluorophenoxy)-1H-imidazo[4,5-c]pyridin-2-yl)furazan-3-ylamine | 4-fluorophenol | MS (ES+) m/e 341 $[M + H]^+$ |
| 300 | N-(3-{[2-(4-furzan-3-yl)-1-ethyl-1H-imidazo[4,5-c]pyridin-6-yl]oxy}phenyl)acetamide hydrochloride | 3-acetamidophenol | MS (ES+) m/e 380 $[M + H]^+$ |
| 301 | N-(4-{[2-(4-furazan-3-yl)-1-ethyl-1H-imidazo[4,5-c]pyridin-6-yl]oxy}phenyl)acetamide hydrochloride | 4-acetamidophenol | MS (ES+) m/e 380 $[M + H]^+$ |

EXAMPLE 302

2-(4-amino-furazan-3-yl)-1-ethyl-N-phenyl-1H-imidazo[4,5-c]pyridin-6-amine

Step 1. 4-(Ethylamino)-5-nitro-2-(phenylamino)pyridine

Anline (1.4 mL, 15 mmol) was added to the product from Example 298, Step 1 (600 mg, 3.0 mmol) in THF (5 mL) and heated to reflux overnight. The solution was cooled, poured into $H_2O$ and extracted with EtOAc. The organic layers were washed with $H_2O$ and brine, dried, filter and concentrated to give a residue which was purified by column chromatography (20-100% EtOAc in hex) to give the title compound which was used directly in the next step. MS (ES+) m/e 259. $[M+H]^+$.

Step 2. 2-(4-Amino-furazan-3-yl)-1-ethyl-N-phenyl-1H-imidazo[4,5-c]pyridin-6-amine The title compound was prepared from the product of Step 1 using the methods described in Example 1 Steps 24; MS (ES+) m/e 322 $[M+H]^+$.

EXAMPLE 303

4-(1-Ethyl-6-methylsulfanyl-1H-imidazo[4,5-c]pyridin-2-yl)-furazan-3-ylamine

Step 1. Ethyl-(2-methylsulfanyl-5-nitro-pyridin-4-yl)-amine

Sodium methyl thiolate (308 mg, 4.4 mmol) was added to a solution of the product from Example 298, Step 1 (800 mg, 4.0 mmol) in DMF (20 mL). After 5 min the reaction mixture was poured into $H_2O$ and extracted with EtOAc. The organic layers were washed with $H_2O$ and brine, dried, filtered and concentrated to give an oil which solidified on standing and was used without further purification. MS (ES+) m/e 214. $[M+H]^+$.

Step 2. N-4-ethyl-6-methylsulfanyl-pyridine-3,4-diamine

The title compound was prepared from the product of Step 1 using the method of Example 177 Step 4. MS (ES+) m/e 184. $[M+H]^+$.

Step 3. 4-(1-Ethyl-6-methylsulfanyl-1H-imidazo[4,5-c]pyridin-2-yl)-furazan-3-ylamine The title compound was prepared from the product of Step 2 using the method of Example 1, Steps 3-4. MS (ES+) m/e 277. $[M+H]^+$.

EXAMPLE 304

4-[1-[4-(2-Dimethylamino-ethoxy)-phenyl]-6-(4-fluorophenoxy)-1H-imidazo[4,5-c]pyridin-2-yl]-furazan-3-ylamine Step 1. (2-Chloro-5-nitro-pyridin-4-yl)-(4-methoxyphenyl)-amine Anisole (908 mg, 7.4 mmol) was added to a solution of 2,4-dichloro-5-nitropyridine (1.30 g, 6.7 mmol) and triethylamine (1.02 mL, 7.4 mmol) in THF (5 mL). The mixture was allowed to stir at rt for 1 h, then was poured into $H_2O$ and extracted with EtOAc. The organic layers were washed with $H_2O$ and brine, dried, filtered and concentrated to a residue which was purified by column chromatography (5-50% EtOAc in hex) to give the title compound as an orange solid, 1.46 g (78%). MS (ES+) m/e 280 $[M+H]^+$.

Step 2. 4-[1-[4-(2-Dimethylamino-ethoxy)-phenyl]-6-(4-fluorophenoxy)-1H-imidazo[4,5-c]pyridin-2-yl]-furazan-3-ylamine The title compound was prepared starting from the product of Step 1 by the method of Example 299, followed by the method of Example 38, followed by the method of Example 41. MS (ES+) m/e 476. $[M+H]^+$.

EXAMPLE 305

4-(1-Cyclopropyl-6-methyl-1H-imidazo[4,5-c]pyridin-2-yl)-furazan-3-ylamine

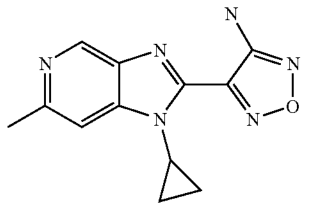

The title compound was prepared from 2,4-dichloro-6-methyl-3-nitropyridine (R. J. Chorvat et al., *J. Med. Chem.*, 1999, 42, 833-848) using the methods in Example 2 Step 1, followed by Example 1 Steps 24; MS (ES+) m/e 257 $[M+H]^+$.

EXAMPLE 306

4-(1-Cyclopropyl-6-methyl-5-oxy-1H-imidazo[4,5-c]pyridin-2-yl)-furazan-3-ylamine

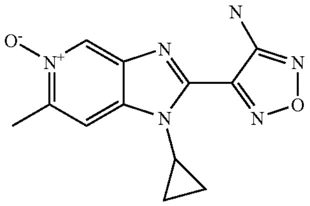

A solution of the product of Example 305 (256 mg, 1 mmol) and meta-chloroperbenzoic acid (50%, 414 mg, 1.2 mmol) in dichloromethane (10 ml) was stirred at room temperature for 1 hour. The solution was diluted with dichloromethane and the organic solution washed with aqueous sodium thiosulphate, saturated sodium bicarbonate solution, water and brine, dried and concentrated in vacuo to give the title compound (242 mg, 89%). MS (ES+) m/e 273 $[M+H]^+$.

EXAMPLE 307

4-(9-Cyclopropyl-2-methylsulfanyl-9H-purin-8-yl)-furazan-3-ylamine

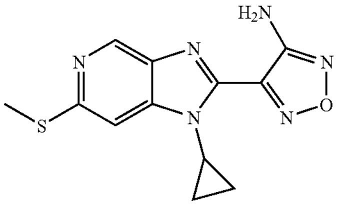

Step 1. (6-Chloro-2-methylsulfanyl-5-nitro-pyrimidine-4-yl)-cyclopropyl-amine 4,6-Dichloro-5-methylsulfanyl-5-nitro-pyrimidine (PCT Int. Appl. (2003), WO 0302544 (14.1 g, 59 mmol), and triethylamine (8.2 ml, 59 mmol) were dissolved in ethanol (400 ml) containing tetrahydrofuran (50 ml) at −60° C. Cycloproplyamine (4.06 ml, 59 mmol) was added dropwise maintaining an internal temperature of −60° C. and stirred slowly to room temperature over 3 hours. The solution was concentrated in vacuo and the residue slurried in diethyl ether. Solid triethylamine hydrochloride was filtered, washed with diethyl ether and the filtrate concentrated in vacuo to afford a crude solid. The solid was purified by column chromatography eluting with a gradient of 40% dichloromethane in hexane to dichloromethane, to afford the title compound (17.89 g, 97%); MS (ES+) m/e 260/262 $[M+H]^+$.

Step 2. 6-chloro-N4-cyclopropyl-2-methansulfanyl-pyrimidine-4,5-diamine

The product of step 1 (5.21 g, 20 mmol) was dissolved in ethanol (150 ml) containing tetrahydrofuran (150 ml) and hydrogenated at 1 atmosphere for 5 hours at room temperature over 10% palladium on charcaol. The catalyst was filtered and the filtrate concentrated in vacuo to afford the title product (4.02 g 87%) that was used in the next step without further purification; MS (ES+) m/e 231/233 $[M+H]^+$.

Step 3. (6-Chloro-9-cyclopropyl-2-methylsulfanyl)-9H-purin-8-yl)-acetonitrile

The title product was obtained from product of step 2 using an analogous procedure to that used in example 1 step 3; MS (ES+) m/e 279/281 $[M+H]^+$.

Step 4. (9-Cyclopropyl-2-methylsulfanyl-9H-purin-8-yl)-acetonitrile

The product of step 3 (81 mg, 0.3 mmol) and zinc powder (300 mg, 4.6 mmol) were heated at reflux in 3N ammonium chloride solution (10 ml) and toluene (5 ml) for 48 hours. The crude mixture was filtered through celite and the filtrate extracted with ethyl acetate (×3). The combined extracts were washed with water (×3), brine, dried over anhydrous magnesium sulfate and concentrated in vacuo to afford a crude solid. The solid was purified by column chromatography eluting with a gradient of hexane to ethyl acetate to afford the title compound (50 mg, 68%); $^1$H NMR ($CDCl_3$) 8.87 (1H s), 4.15 (2H, s), 3.29 (1H, m), 2.65 (3H, s), 1.34 (4H, m).

Step 5. 4-(9-Cyclopropyl-2-methylsulfanyl-9H-purin-8-yl)-furazan-3-ylamine

The title compound was prepared from the product of step 4 using an analogous procedure to that used in example 1 step 4; MS (ES+) m/e 290 $[M+H]^+$.

EXAMPLE 308

3-(1-Ethyl-1H-imidazo[4,5-c]pyridin-2-yl)-pyrazin-2-ylamine

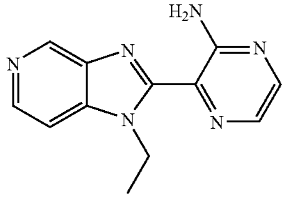

To polyphosphoric acid, preheated to 130° C., was added in one portion an intimate mixture of the product of Example 1 Step 2 (206 mg, 1.5 mmol) and 3-aminopyrazine-2-carboxylic acid (230 mg, 1.65 mmol). The temperature was increased to 195° C. for 1 hour and then cooled back to 130° C. for a further 1 hour. The viscous oil was poured on to ice containing saturated sodium carbonate solution and diethyl ether (5 ml) and the aqueous solution was extracted with chloroform (×5). The combined organic extracts were washed with brine, dried over anhydrous magnesium sulfate and concentrated in vacuo. The crude solid was purified by silica gel chromatography eluting with a gradient of dichloromethane to 0.880 ammonia:ethanol:dichloromethane (1:9:40), to afford the title compound, (20 mg, 6%); MS (ES+) m/e 241 $[M+H]^+$.

EXAMPLE 309

4-(1-Ethyl-1H-imidazo[4,5-c]pyridin-2-yl)-1H-pyrazol-3-ylamine

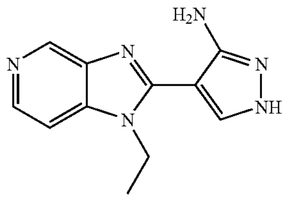

Step 1. Dimethylamino-(1-ethyl-1H-imidazo[4,5-c]pyridin-2-yl)-acrylonitrile

The product of Example 1 Step 3 (334 mg, 1.8 mmol) and N,N-dimethylformamide dimethylacetal (214 mg, 1.8 mmol) in orthoxylene (4 ml) was heated under reflux for 45 min. After cooling, the solution was concentrated and the residue co-evaporated with toluene (x3) to afford the title compound which was used directly in the next step; MS (ES+) m/e 242 $(M+H)^+$.

Step 2. 4-(1-Ethyl-1H-imidazo[4,5-c]pyridin-2-yl)-1H-pyrazol-3-ylamine

The product of Step 2 (217 mg, 0.9 mmol) and hydrazine hydrate (90 mg, 1.8 mmol) in methanol (5 ml) was heated under reflux for 5 hours. After cooling, the reaction mixture was concentrated and the residue purified by silica gel chromatography eluting with 0.880 ammonia:ethanol:dichloromethane (1:9:90), to afford the title compound, (27 mg, 13%); MS (ES+) m/e 229 $[M+H]^+$.

EXAMPLE 310

2-(4-Amino-furazan-3-yl)-1-ethyl-1H-imidazo[4,5-c]pyridine-7-carbaldehyde

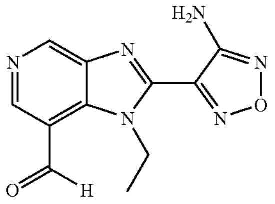

A solution of the product from Example 100 (0.1 g, 0.324 mmol) in tetrahydrofuran (4 ml) at −78° C. was treated with a i 0.6M solution of n-butyllithium (0.6 ml, 0.97 mmol) in hexanes. After 5 minutes the mixture was treated with dimethylformamide (0.3 ml) and allowed to reach room temperature. After 30 minutes at room temperature the reaction was carefully quenched with water and extracted into dichloromethane (x2). The organic layer was then washed with brine, dried ($Na_2SO_4$) and reduced in vacuo. The residue was purified by silica gel chromatography eluting with ethyl acetate, to afford the title compound, (0.0349, 41%); MS (ES+) m/e 259 $[M+H]^+$.

EXAMPLE 311

[2-(4-Amino-furazan-3-yl)-3-ethyl-3H-imidazo[4,5-c]pyridin-4-yl]-methanol

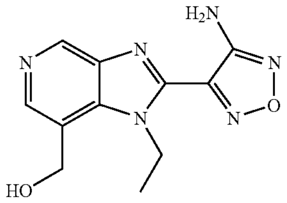

A solution of the product from Example 310 (0.150 g, 0.577 mmol) in methanol (10 ml) was treated with sodium borohydride (0.0249, 0.635 mmol) and stirred at room temperature for 1 hour. The mixture was then treated with a few drops of acetic acid and then applied directly to an SCX ion exchange cartridge and washed with methanol and then a mixture of 0.880 ammonia and methanol (1:9).

The basic fractions were combined and reduced to furnish the title compound without further purification; MS (ES+) m/e 263 $[M+H]^+$.

EXAMPLE 312

[2-(4-Amino-furazan-3-yl)-1-ethyl-1H-imidazo[4,5-c]pyridin-7-ylmethyl]-[1-(2-methoxy-ethyl)-piperidin-4-yl]-amine

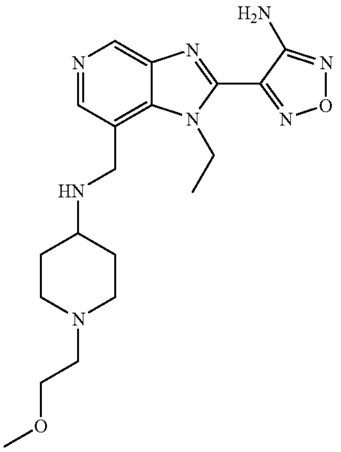

Step 1. 1-(2-methoxy-ethyl)-piperidin-4-yl]-carbamic acid tert-butyl ester

A mixture of piperidin-4-yl]-carbamic acid tert-butyl ester (500 mg, 2.5 mmol), potassium carbonate (621 mg, 4.5 mmol) and 1-bromo-2-methoxyethane (382 mg, 2.75 mmol) in ethanol 5 ml) was heated at reflux for 18 hours. After cooling to room temperature the mixture was filtered and the filtrate concentrated in vacuo. Purification of the residue by silica gel chromatography eluting dichloromethane/methanol/0.880 ammonia (100:10:1) gave the title compound (500 mg, 78%); MS (ES+) m/e 259 $[M+H]^+$.

Step 2. 1-(2-Methoxy-ethyl)-piperidin-4-ylamine

The title compound was prepared from the product of Step 1 using the method of Example 21; (165 mg, 54%); MS (ES+) m/e 159 $[M+H]^+$.

Step 3. [2-(4-Amino-furazan-3-yl)-1-ethyl-1H-imidazo[4,5-c]pyridin-7-ylmethyl]-[1-(2-methoxy-ethyl)-piperidin-4-yl]-amine The title compound was prepared from the product of Step 2 the product of Example 310 using the method of Example 149; MS (ES+) m/e 401 $[M+H]^+$.

EXAMPLE 313

4-(3-ethyl-3H-imidazo[4,5-c]pyridin-2-yl)-furazan-3-ylamine

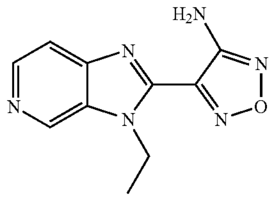

Step 1. Ethyl-(4-nitro-1-oxy-pyridin-3-yl)-amine

A solution of 3-bromo-4-nitropyrimidine-1-oxide (Daisley, R. W., Hanbali, J. R.; *Org. Prep. Proced. Int.*, 1983, 15(4), 280) (8.1 g, 37 mmol) in chloroform (250 ml) at 0° C. was treated with ethylamine (70% aqueous solution, 25 ml). After stirring at room temperature for 3 hours additional ethylamine solution (25 ml) was added and stirring continued for a further 3 hours. The solution was concentrated in vacuo and the residue was purified by silica gel chromatography, eluting with a gradient of 10% ethylacetate/hexane to ethylacetate to afford the title compound, (3.68 g, 54%); $^{1}H$ NMR ($CDCl_3$) 8.02 (1H, d, J=7.6 Hz), 7.92 (1H, d, J=1.6 Hz), 7.81 (1H, br s), 7.46 (1H, dd, J=7.6, 1.6 Hz), 3.32 (2H, m), 1.40 (3H, t, J=7.2 Hz).

Step 2. N-3-ethyl-pyridine-3,4-diamine

The product of step 1 (3.68 g, 20 mmol) was dissolved in a 1:1 mixture of ethanol:tetrahydrofuran (300 ml) and hydrogenated at room temperature and atmospheric pressure using raney nickel (ca. 1 g) for 18 hours. The catalyst was removed by filtration on a filter aid pad and the filtrate concentrated in vacuo to afford the title compound which was used without further purification, (2.72 g, 99%); $^{1}H$ NMR (DMSO) 7.53 (2H, m), 6.43 (1H, d, J=4.8 Hz), 5.50 (2H, br s), 4.42 (1H, br s), 3.01 (2H, m), 1.21 (3H, t, J=7.2 Hz).

Step 3. 3-ethyl-3H-imidazo[4,5-c]pyridin-2-yl)-acetonitrile

The title compound was prepared from the product of step 2 using the analogous procedure to that used in example 1, step 3, (1.56 g, 11 mmol), affording (1.099, 49%); $^{1}H$ NMR ($CDCl_3$) 8.88 (1H d, J=0.8 Hz), 8.49 (1H, d, J=5.6 Hz), 7.68 (1H, dd, J 5.6, 0.8 Hz), 4.38 (2H, q, J 7.4 Hz), 4.13 (2H, s), 1.59 (3H, t, J=7.4 Hz).

Step 4. 4-(3-ethyl-3H-imidazo[4,5-c]pyridin-2-yl)-furazan-3-ylamine

The title compound was prepared from the product of step 2 using the analogous procedure to that used in example 1, step 4, (1.03 g, 5.5 mmol) affording (240 mg, 49%); MS (ES+) m/e 231 $[M+H]^+$.

EXAMPLE 314

4-(3-Ethyl-5-oxy-3H-imidazo[4,5-c]pyridin-2-yl)-furazan-3-ylamine

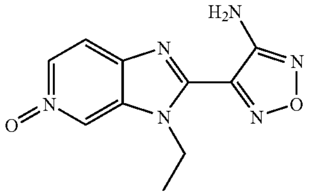

The product of Example 313, Step 4 (362 mg, 1.6 mmol) in acetic acid (2 ml) was treated with 30% wt aqueous solution of hydrogen peroxide (432 mg, 3.1 mmol) and the solution was heated at 80° C. for 18 hours. After cooling to room temperature the mixture was basified with solid sodium carbonate and extracted with chloroform (×5). The combined extracts were washed with brine, dried over anhydrous sodium sulfate and concentrated in vacuo. The residue was purified by column chromatography eluting with 0.880 ammonia:ethanol:dichloromethane (1:9:90) to afford the title product, (370 mg, 96%); MS (ES+) m/e 247 $[M+H]^+$.

EXAMPLE 315

4-(3-ethyl-4-methoxy-3H-imidazo[4,5-c]pyridin-2-yl)-furazan-3-ylamine

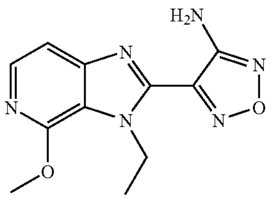

The product of Example 314 (370 mg, 1.5 mmol) in phosphorous oxychloride (5 ml). was heated at reflux for 4 hours. The solution was cooled and co-evaporated with toluene, the residue was basified with ice cold sodium carbonate and the aqueous solution extracted with ethyl acetate (×3). The combined extracts were washed with brine, dried over anhydrous sodium sulfate and concentrated in vacuo. The residue was suspended in a solution of 50% sodium hydroxide (5 ml), containing methanol (5 ml) and heated at 80° C. for 5 hours. The solution was concentrated in vacuo and the resulting wet solid that was extracted with ethyl acetate (×3). The combined extracts were washed with water (×2), brine, dried over anhydrous sodium sulfate and concentrated in vacuo. The residue was purified by column chromatography eluting with a gradient of dichloromethane to 0.880 ammonia:ethanol:dichlorormethane (1:9:90), to afford the title compound (30 mg, 8%); MS (ES+) m/e 445 $[M+H]^+$.

EXAMPLE 316

4-[1-(2-Methanesulfonyl-1,2,3,4-tetrahydro-isoquinolin-7-yl)-1H-imidazo[4,5-c]pyridin-2-yl]-furazan-3-ylamine

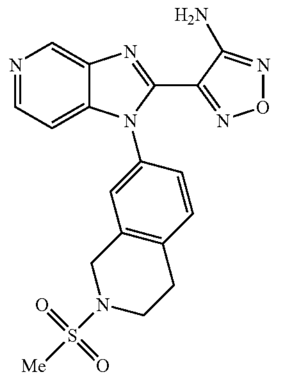

To a 0° C. solution containing 19 mg of example 97 (0.05 mmols) in 0.5 mL of dry DMF and 0.22 mL of triethylamine, was added 7 mg of methanesulfonyl chloride (0.06 mmols). The reaction mixture turned yellow. After stirring at 0° C. for 30 min., the reaction mixture was partitioned between 5 mL water and 10 mL of EtOAc. The organic layer was washed with water (2×5 mL), dried over $MgSO_4$, filtered, and concentrated in vacuo. The resulting residue was purified by Gilson reverse-phase HPLC to yield the title compound (3 mg, 14%). MS (ES+) m/e 412 $[M+H]^+$.

PHARMACY EXAMPLES

Tablets a)

| | |
|---|---|
| Compound of the invention | 50.0 mg |
| Lactose | 70.0 mg |
| Microcrystalline Cellulose | 70.0 mg |
| Cross-linked Polyvinylpyrrolidone | 8.0 mg |
| Magnesium Stearate | 2.0 mg |
| Compression weight | 200.0 mg |

The compound of the invention, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

b)

| | |
|---|---|
| Compound of the invention | 50.0 mg |
| Lactose | 120.0 mg |
| Pregelatinised Starch | 20.0 mg |
| Cross-linked Polyvinylpyrrolidone | 8.0 mg |
| Magnesium Stearate | 2.0 mg |
| Compression weight | 200.0 mg |

The compound of the invention, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

Capsules a)

| | |
|---|---|
| Compound of the invention | 50.0 mg |
| Lactose | 148.0 mg |
| Magnesium Stearate | 2.0 mg |
| Fill weight | 200.0 mg |

The compound of the invention and pregelatinised starch are screened through a 500 micron mesh sieve, blended together and lubricated with magnesium stearate, (meshed. through a 250 micron sieve). The blend is filled into hard gelatine capsules of a suitable size.

b)

| | |
|---|---|
| Compound of the invention | 50.0 mg |
| Lactose | 132.0 mg |
| Polyvinylpyrrolidone | 8.0 mg |
| Cross-linked Polyvinylpyrrolidone | 8.0 mg |
| Magnesium Stearate | 2.0 mg |
| Fill weight | 200.0 mg |

The compound of the invention and lactose are blended together and granulated with a solution of polyvinylpyrrolidone. The wet mass is dried and milled. The magnesium stearate and cross-linked polyvinylpyrrolidone are screened through a 250 micron sieve and blended with the granules. The resultant blend is filled into hard gelatine capsules of a suitable size.

Injection Formulation

| | % w/v |
|---|---|
| Compound of the invention | 0.10 |
| Water for injections B.P. to | 100.00 |

Sodium chloride may be added to adjust the tonicity of the solution and the pH may be adjusted to that of maximum stability and/or to facilitate solution of the compound of the invention using dilute acid or alkali or by the addition of suitable buffer salts. Solubilisers, such as cosolvents, may also be added to facilitate solution of the compound of the invention. Antioxidants and metal chelating salts may also be included. The solution is clarified, made up to final volume with water and the pH remeasured and adjusted if necessary, to provide 1 mg/ml of the compound of formula (I).

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

Further sterile formulations are prepared in a similar manner containing 0.05, 0.20 and 0.5% w/v of the compound of the invention, so as to provide respectively 0.5, 2 and 5 mg/ml of the compound of the invention.

Biological Activity

Rho-kinase Activity

Using the test procedure described in the specification the compounds of the examples where found to have a pIC50 in the range 9 to 5.2.

Msk-1 Activity

The compounds of the examples have a pIC50 value in the range of 9.28 to 5.15.

The compounds of the invention are essential non-toxic at therapeutically useful doses. Thus no adverse effects were observed when compounds of the invention have been administered to rats at a dose of 10 mg/kg.

The invention claimed is:

1. A compound of the general formula (I)

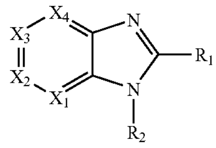

(I)

and physiologically acceptable salts and or N-oxides thereof wherein, $X^3$ is N, $X^4$ is $CR^6$, $X^1$ is $CR_3$, and $X^2$ is $CR^4$;

$R^1$ is a group C

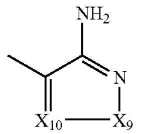

(c)

wherein $X_9$ is O and $X_{10}$ is N;

$R_2$ represents hydrogen, hydroxy, aryl, heteroaryl, $C_{3-7}$cycloalkyl, heterocyclyl, a group $YR_{12}$, $N{=}R_{13}$, $CONR_{14}R_{15}$, $COCH_2NR_{19}R_{20}$, $NR_{14}COR_{16}$, $SO_2NR_{14}R_{15}$ or $C_{1-6}$alkyl [optionally substituted by a group selected from optionally substituted phenyl, $C_{3-7}$cycloalkyl, heteroaryl, heterocyclyl, acylamino, $NH_2$, $R_{19}NH$, $R_{19}R_{20}N$, $SO_2NR_{14}R_{15}$, $CONR_{14}R_{15}$, $NR_{14}COR_{16}$, $OalkNR_{19}R_{20}$, $SalkNR_{19}R_{20}$or $NR_{17}SO_2R_{18}$ group];

$R_3$, $R_4$, and $R_6$, independently represent a group selected from hydrogen, halogen, hydroxy, $R_{19}O$, $R_{19}S(O)_n$, $NH_2$, $R_{19}NH$, $R_{19}R_{20}N$, nitro, formyl, C1-4alkanoyl, alkenyl (optionally substituted by optionally substituted phenyl, heterocyclyl, or heteoaryl), carboxy, optionally substituted phenyl, heteroaryl, cycloalkyl, cycloalkylalkyl, aryloxy, heteroaryloxy, heterocyclyl, $CONR_{14}R_{15}$, $NR_{14}COR_{16}$ $SO_2NR_{14}R_{15}$, $NR_{17}SO_2R_{18}$ or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$, acylamino, hydroxy, $CONR_{14}R_{16}$, $NR_{14}COR_{16}$, $SO_2NR_{14}R_{15}$, $NR_{17}SO_2R_{18}$, $OalkNR_{19}R_{20}$, or $SalkNR_{19}R_{20}$group];

$R_{19}$ and $R_{20}$ independently represent a group selected from $C_{1-6}$ alkyl, $C_{3-7}$cycloalkyl, $C_{3-7}$cycloalkylalkyl, aryl, aralkyl, heteroaryl, heteroarylalkyl, heterocyclyl or heterocyclylalkyl;

Y represents O, NH, $NR_{12}$ or $S(O)_n$;

$R_{12}$ represents aryl, heteroaryl, cycloalkyl, heterocyclyl or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$ , acylamino, hydroxy, $CONR_{14}R_{15}$, $NR_{14}COR_{16}$, $SO_2NR_{14}R_{15}$, $NR_{17}SO_2R_{18}OalkNR_{19}R_{20}$, or SalkNR19$R_{20}$ group];

$R_{13}$ represents an alkylidene group which may be substituted by an aryl, heteroaryl, heterocyclyl or cycloalkyl group or $R_{13}$ represents a cycloalkylidene or heterocycloalkylidene group;

$R_{14}$ and $R_{15}$ independently represent hydrogen, aryl, heteroaryl, cycloalkyl or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$ , or acylamino group] or $R_{14}$ and $R_{15}$ together with the nitrogen atom to which they are attached form a 4-7 heterocyclic ring which may be saturated or unsaturated and optionally contains another heteroatom selected from O, N or $S(O)_n$;

$R_{16}$ and $R_{18}$ independently represent, aryl, heteroaryl, heterocyclyl, cycloalkyl or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$ , or acylamino group] or the group $NR_{14}R_{15}$ wherein $R_{14}$ and $R_{15}$ have the meanings defined above;

$R_{17}$ represents hydrogen, aryl, heteroaryl, heterocyclyl, cycloalkyl or $C_{1-6}$alkyl [optionally substituted by a group selected from optionally substituted phenyl, $C_{3-7}$cycloalkyl, heteroaryl, heterocyclyl, $NH_2$, $R_{19}NH$, $R_{19}R_{20}N$ , or acylamino group];

Alk is a $C_{2-4}$ straight or branched alkylene chain n is zero, 1 or 2.

2. A compound as claimed in claim 1 wherein $R_2$ represents hydrogen, $C_{1-6}$alkyl, $C_{3-7}$cycloalkyl, $C_{3-7}$cycloalkylmethyl, phenyl or phenyl substituted by (amino, dialkylamino, dialkylaminoalkylamino, alkyl, alkanoyl, alkoxy, halo, hydroxy, aminoalkyl, hydroxalkoxy, aminoalkoxy, alkylaminoalkoxy, N-aralkyl-Nalkylaminoalkoxy, aminocarbonylalkoxy, alkylaminocarbonylalkoxy, dialkylaminocarbonylalkoxy, ureidoalkoxy, alkylureido, dialkylaminoacetamido, alkylthioalkoxy, phenylthioalkoxy, alklsulphinylalkoxy, phenylsulphinylalkoxy, alkylsulphonylalkoxy, phenylsulphonylalkoxy, cyanoalkoxy, acylaminoethoxy, alkylsuphonylaminoalkoxy, phenylsulphonylaminoalkoxy, alkoxycarbonylalkoxy, heterocyclylalkoxy, heterocyclyloxy, heterocyclyl), alkyl substituted by (hydroxy, amino, acylamino, $R_{19}NH$, $R_{19}R_{20}N$, a 4-7-membered heterocyclyl group), a 4-7 membered heterocyclyl group, a 5,6 fused bicyclic hetroaryl group, a 6,6 fused bicyclicheterocyclic group, a 6,5 fused heterocyclic group or a 6,7 fused heterocyclic group.

3. A compound as claimed in claim 1 wherein $R_2$ represents hydrogen, methyl, ethyl, isopropyl, sec butyl, 2-ethylbutyl, cyclopropyl, cyclobutyl, cyclopentyl, cyclohexyl, cycloheptyl, cyclopropylmethyl, cyclohexylmethyl, phenyl, phenyl substituted by [amino 4-dimethylamino, dimethylaminoethylamino, N-methyl dimethylaminoethylamino, N,N-bis(2-dimethylaminoethyl)amino), ethyl, acetyl, methoxy 3-methylbutoxy, chlorine, brominehydroxy, aminomethyl, 2-hydroxyethoxy, 3-hydroxypropoxy, 2-aminoethoxy, 2-methylaminoethoxy, 2-dimethylaminoethoxy, 2-diethylaminoethoxy, 2-diethylamino-1-methylethoxy, 2-disopropylamino-1-methylethoxy, N,N-benzyl N-methylaminoethoxy, aminocarbonylmethoxy, aminocarbonyl-2-methylethoxy, aminocarbonylethoxy, methylaminocarbonylmethoxy, dimethylaminocarboxymethoxy, ureidomethoxy, 3-methylureido, dimethylaminoacetamido, methylthiomethoxy, phenylthiomethoxy, methylsulphinylmethoxy, phenylsulphinylmethoxy, methylsulphonylmethoxy, phenylsulphonylmethoxy, cyanomethoxy, 2-cyanoethoxy, t-butoxycarbonylaminoethoxy, isoxazolylaminoethoxy, isonicotinylaminoethoxy, methylsulphonylaminoethoxy, phenylsulphonylaminoethoxy, 2-methoxycarbonyl 1-methylethoxy, morpholinoethoxy, piperidinoethoxy, 1-pyrroldino-2-ylmethoxy, 1-methyl-piperidino-4-yloxy or 3-pyrrolidinyl,] 2-hydroxy-1-methylethyl, 3-aminopropyl, 4-aminobutyl, 5-aminopentyl, 4-butyloxycarbonylamino-butyl, 2-dimethylamino-1-methylethyl, 4-diethylamino-1-methyl-butyl, 3-dimethylaminopropyl, 4-methylpiperazin-1-ethyl, 2-piperazin-yl-ethyl, piperidine 4-yl methyl, piperidine 3-yl methyl, piperidin-4-yl, piperidin-3-yl, pyrrolidin-3-yl, 5-indazolyl or 6-indazolyl, tetrahydroisoquinolin-5-yl, 2-methyl tetrahydroisoquinolin-7-yl, 2-methanesulphonyl-tetrahydroisoquinolin-7-yl, tetrahydroisoquinolin-7-yl, 3,4-dihydro-2H-isoquinolin-1-one-7-yl, 2,3-dihydro-1H-isoindol-5-yl, benzo{1,3]dioxol-5-yl or 2,3,4,5-tetrahydro-1H-benzo[c]azepin-8-yl.

4. A compound as claimed in claim 1 wherein $R_3$ represents hydrogen, halogen, hydroxy, carboxyl, phenyl or phenyl (substituted by one or two groups selected from alkoxy, hydroxy, hydroxymethyl, trifluoromethyl, trifluoromethoxy, amino, acetamido, aminoalkyl, alkyl, carboxyl carboxamido, N,N-dimethylcarboxamido, cyano, formyl, phenoxy, $CH_3S(O)n$ wherein n is zero, 1 or 2, $CH_3SO_2NH$, or halogen), or heterocyclyl, heteroaryl, 6,5-fused bicycloheterocyclyl, an optionally substituted phenyl substituted by the group $CH_2NR_{19}R_{20}$ wherein $R_{19}$ is alkyl, phenyl or a heterocyclic group and $R_{20}$ is hydrogen or methyl, or $NR_{19}R_{20}$ is a 4-7 heterocyclic group, alkyl substituted by (a 4-7 membered heterocyclyl group or a group $NR_{19}R_{20}$ (wherein $R_{19}$ is hydroxylalkyl, optionally substituted benzyl, $C_{3-7}$ cycloalkyl, a heterocyclic group, a 4-7 membered heterocyclalkyl or $C_{3-7}$ cycloalkylalkyl, $R_{20}$ is hydrogen, methyl or acetyl), 4-heterocyclyoxy, heterocyclylalkyloxy, vinyl (optionally substituted by optionally substituted phenyl), $CONR_{14}R_{15}$ wherein $R_{15}$ is hydrogen, $R_{14}$ is benzyl, phenethyl, aminoalkyl, 4-7 membered heterocyclyl or 4-7 membered heterocyclylalkyl, or $R_{14}$ and $R_{15}$ together with the nitrogen atom to which they are attached represent a 4-7 membered heterocyclyl group, a group $R_{19}S(O)n$ (wherein n is zero, 1 or 2 and $R_{19}$ is optionally substituted phenyl), or a group $R_{19}NH$ and $R_{19}$ is optionally substitued phenyl or heteroaryl.

5. A compound as claimed in claim 1 wherein $R_3$ represents hydrogen, bromine, hydroxy, carboxyl, phenyl or phenyl (substituted by one or two groups selected from methoxy, ethoxy, hydroxy, hydroxymethyl, trifluoromethyl, trifluoromethoxy, amino, acetamido, aminomethyl, aminoethyl, methyl, ethyl, carboxyl, carboxamido, N,N-dimethylcarboxamido, cyano, formyl, phenoxy, $CH_3S(O)n$ wherein n is zero, 1 or 2, $CH_3SO_2NH$, or fluorine), 5-methyl-1,2,4-oxadiazol-3-yl, 2-thienyl, 4-methylthienyl, 5-phenylthienyl, 5-formylthienyl, or 3-thienyl, 2-furanyl, pyridyl such as 3-pyridyl or 4-pyridyl, 3,5-dimethylisoxazol-4-yl, indolyl or 8-quinolinyl, benzothienyl, 5-benzo[1,3]dioxolyl, a phenyl or fluorophenyl substituted by the group $CH_2NR_{19}R_{20}$ (wherein $NR_{19}R_{20}$ represents ethylamino, dimethylamino, 4-morpholino, pyrrolidino, piperidino, piperidin-4-yl-amino or 1-t-butoxycarbonyl-piperdin-4-yl-amino), 3-hydroxypropylamino, 4-bromobenzylamino, 4-methoxybenzylamino, 4-piperidinylaminomethyl, N-4-piperidinyl-N-methylaminomethyl, 1-t-butyoxycarbonyl-piperidinyl-aminomethyl, 4-aminopiperidinomethyl, 1,4-diazepan-1-ylmethyl, piperazinomethyl, 4-methylpiperazinomethyl, 4-acetylpiperizin-1-ylmethyl, 4-ethylpiperazinomethyl, 4-morpholinomethyl, piperidinomethyl, 4-(methylamino)piperidinomethyl, 4-cyclopropylaminopiperidinomethyl, pyrrolidinomethyl, 3-dimethylaminopyrrolidinomethyl, 2-hydroxymethylpyrrolidinomethyl, 4-ethylpiperazino-methyl, 3-pyrrolidin-1-yl-propylaminomethyl, 4-(4-fluorophenyl)piperazinomethyl, 3-piperidinyl-1-yl-propylaminomethyl, 3-morpholin-4-yl-propylaminomethyl, 3-(4-methylpiperazin-yl propylaminomethyl, 1-methyl piperidin-4-yl-aminomethyl, 4-pyrrolidinocarbonylmethyl-piperazinomethyl, 2-pyrrolidin-1-ylmethylpyrrolidinomethyl, 2-pyrrolidin-1-yl-ethylaminomethyl, 3-dimethylaminopyrrolidinomethyl, 1-methyl-piperidin-4-ylaminomethyl, 1-isopropyl-piperidin-4-ylaminomethyl, 3-dimethylaminopyrrolidinomethyl, 2-(morpholin-yl-methyl)-pyrrolidinomethyl, 3-piperidin-1-yl-propylaminomethyl, 3-morpholin-4-yl-propylaminomethyl, 3-(4-methylpiperazin-1-ylpropylaminomethyl, piperidin-1-ylmethylpyrrolidinomethyl, 3,5-dimethylpiperazinomethyl, pyrrolidin-1-ylpiperidinomethyl, pyrrolidino-3-ylaminomethyl, pyrrolidin-2-ylmethylaminomethyl, 4-aminomethylcyclohexymethylaminonlethyl, 4-aminocyclohexylaminomethyl, 2-piperazin-1-ylethylamoinomethyl, 3-amino-pyrrolidinomethyl, pyrrolidino-2-ylmethylaminomethyl, piperidin-4-ylmethylaminomethyl, 4-aminomethylpiperdininomethyl, 4-(cyclopropylaminopiperidinomethyl, 3-(piperazino-1-yl) propylaminomethyl, 2-(morpholin-4-ylmethyl)pyrrolidinomethyl, 2-(piperidin-1-ylmethyl)pyrrolidinomethyl, 2-(piperazin-1-ylmethyl)pyrrolidinomethyl, piperidin-4-ylmethyl, N-piperidin-4-yl-acetamidomethyl, piperidin-4-yloxy, or piperidin-4-ylmethyloxy, 4-methyloxystyryl, $CONR_{14}R_{15}$ wherein $R_{15}$ is hydrogen, $R_{14}$ is benzyl, phenethyl, 3-aminopropyl, 4-aminobutyl, 6-aminohexyl, 3 or 4-piperidinyl 1-aminomethylcarbonyl-piperidin-4-yl, 3-pyrroldinyl, piperidin-2-ylmethyl or piperidin-4-ylmethyl, morpholin-2-ylmethyl or piperazinoethyl, or $R_{14}$ and $R_{15}$ together with the nitrogen atom to which they are attached represent piperazino, 1-methylpiperazino, 4-(2-aminoethyl)piperazino, 4-(t-butoxycarbonylaminoethyl)piperazino, 4-aminomethylcarbonylpiperazino, 4-aminoethylcarbonylpiperazino, 4-1-(aminoethylcarbonylpiperazino, 4-(1-methylaminoethylcarbonylpiperazino, 4-pyrrolidin-2-yl-carbonylpiperazino, pyrrolidino, 3-aminopyrrolidino, 2-methoxycarbonylpyrrolidino, morpholino, 2-(pyrrolidin-1-yl)methyl pyrrolidino, a group $R_{19}S(O)n$ wherein n is zero, and $R_{19}$ is phenyl optionally substituted by methoxy, a group $R_{19}NH$ wherein $R_{19}$ is phenyl, 4-morpholinophenyl or 3-aminopyridyl.

6. A compound as claimed in claim 1 wherein $R_4$ is hydrogen, methyl, methoxy, methylthio, phenylamino or phenoxy optionally substituted by fluorine or acetamido.

7. A compound as claimed in claim 1 wherein $R_6$ is hydrogen, chlorine, hydroxymethyl, methyl, methoxy, phenyl, 1-pyrrolidinyl or 1-pyrazolyl.

8. A pharmaceutical formulation comprising a compound according to claim 1 or a pharmaceutically acceptable salt and or an N oxide thereof together with one or more pharmaceutically acceptable excipients and/or carriers.

9. The method of inhibiting the kinase Msk-1 which comprises the administration of a compound according to claim 1 and/or a physiologically acceptable salt thereof.

10. The method of inhibiting Rho-kinase 1 which comprises the administration of a compound according to claim 1 and/or a physiologically acceptable salt thereof.

11. The method of inhibiting Rho-kinase 2 which comprises the administration of a compound according to claim 1 and/or a physiologically acceptable salt thereof.

* * * * *